United States Patent [19]
Bito et al.

[11] Patent Number: 5,906,625
[45] Date of Patent: May 25, 1999

[54] TISSUE-FIXING SURGICAL INSTRUMENT, TISSUE-FIXING DEVICE, AND METHOD OF FIXING TISSUE

[75] Inventors: Shiro Bito, Farmingdale, N.Y.; Isami Hirao, Tokyo, Japan; Kazuhiko Oozeki, Tokyo, Japan; Minoru Tsuruta, Tokyo, Japan; Akito Mukaizawa, Suita, Japan; Akio Nakada, Tokyo, Japan; Tsuyoshi Tsukagoshi, Tokyo, Japan; Toshihiko Suzuta, Tokyo, Japan; Shuichi Kimura, Tokyo, Japan; Seiji Kuramoto, Huntington Station, N.Y.; Naoki Uchiyama, Tokyo; Norikiyo Shibata, Yamato, both of Japan

[73] Assignee: Olympus Optical Co., Ltd., Tokyo, Japan

[21] Appl. No.: 08/808,456

[22] Filed: Feb. 28, 1997

Related U.S. Application Data

[63] Continuation-in-part of application No. 08/620,364, Mar. 22, 1996, Pat. No. 5,797,931, which is a continuation-in-part of application No. 08/384,210, Feb. 3, 1995, Pat. No. 5,658,300, which is a continuation of application No. 08/072,224, Jun. 3, 1993, abandoned.

[30] Foreign Application Priority Data

| Jun. 4, 1992 | [JP] | Japan | 4-144299 |
| Jun. 4, 1992 | [JP] | Japan | 4-144640 |
| Mar. 31, 1993 | [JP] | Japan | 5-094963 |
| May 18, 1995 | [JP] | Japan | 7-119712 |
| Sep. 18, 1995 | [JP] | Japan | 7-238667 |
| Jul. 29, 1996 | [JP] | Japan | 8-199188 |

[51] Int. Cl.⁶ .................................................. A61B 17/04
[52] U.S. Cl. ........................ 606/142; 606/139; 606/143
[58] Field of Search ................................. 606/1, 142, 143, 606/139; 600/437; 601/2

[56] References Cited

U.S. PATENT DOCUMENTS

| 3,053,124 | 9/1962 | Balamuth et al. | 228/56.2 |
| 3,513,848 | 5/1970 | Winston et al. | 606/228 |
| 4,487,205 | 12/1984 | Di Giovanni et al. | 606/157 |
| 4,498,476 | 2/1985 | Cerwin et al. | 606/157 |
| 4,805,618 | 2/1989 | Ueda et al. | 606/157 |
| 4,983,177 | 1/1991 | Wolf | 606/157 |
| 5,040,715 | 8/1991 | Green et al. | 227/176 |
| 5,084,057 | 1/1992 | Green et al. | 606/142 |
| 5,171,251 | 12/1992 | Bregen et al. | 606/151 |
| 5,171,252 | 12/1992 | Friedland | 606/157 |
| 5,201,900 | 4/1993 | Nardella | 606/157 |
| 5,207,691 | 5/1993 | Nardella | 606/142 |
| 5,336,230 | 8/1994 | Leichtling et al. | 606/148 |

*Primary Examiner*—Gary Jackson
*Attorney, Agent, or Firm*—Frishauf, Holtz, Goodman, Langer & Chick

[57] ABSTRACT

A surgical instrument for fastening together opposing portions of a body organ. The instrument comprises a first support for supporting the first opposing portion of the body organ, a second support opposing the first support, for supporting the second opposing portion of the body organ, and a displacement-preventing member connected to the first or second support for preventing the supports from displacing relative to each other. The member comprises a pin protruding from one of the supports and a hole formed in the other of the supports. The pin is made of thermoplastic resin. When heated, the pin is softened and deformed, whereby the first and second supports are secured to each other, fastening together the opposing portions of the body organ.

30 Claims, 59 Drawing Sheets

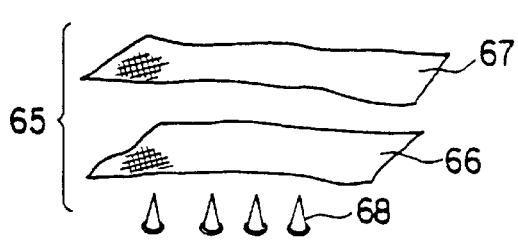
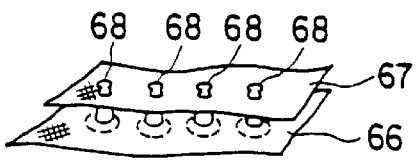
FIG. 18A   FIG. 18B
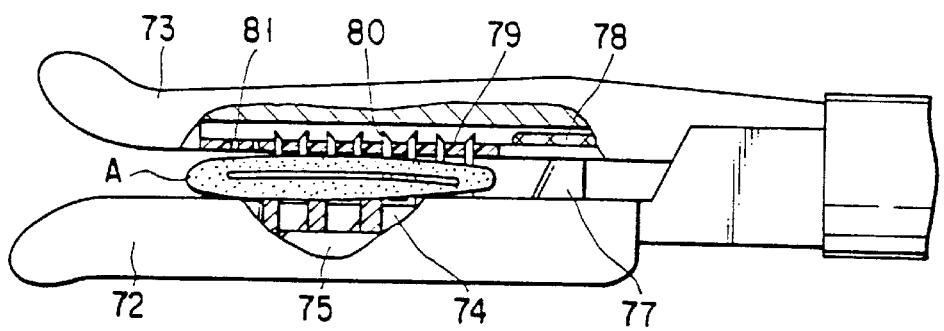
FIG. 19
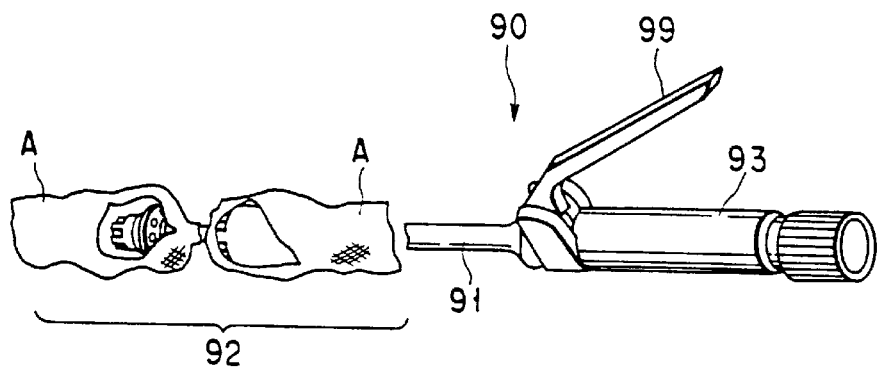
FIG. 20

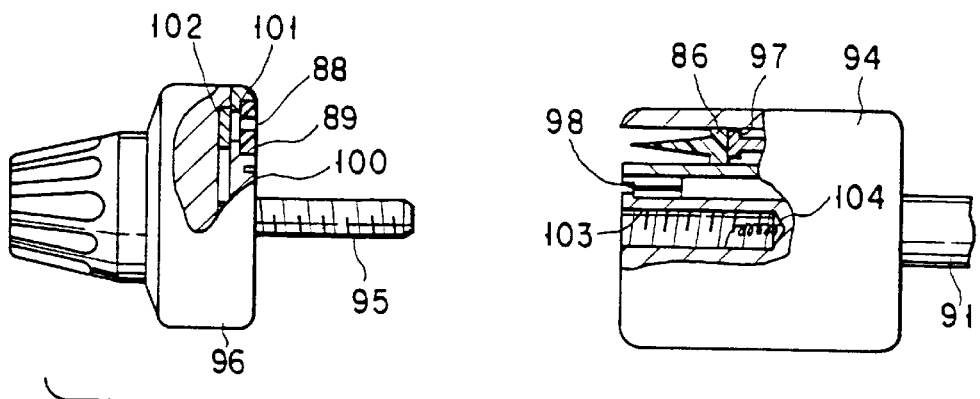
F I G. 21
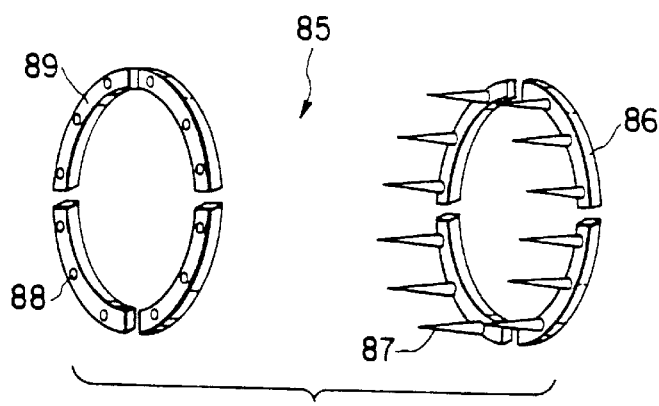
F I G. 22
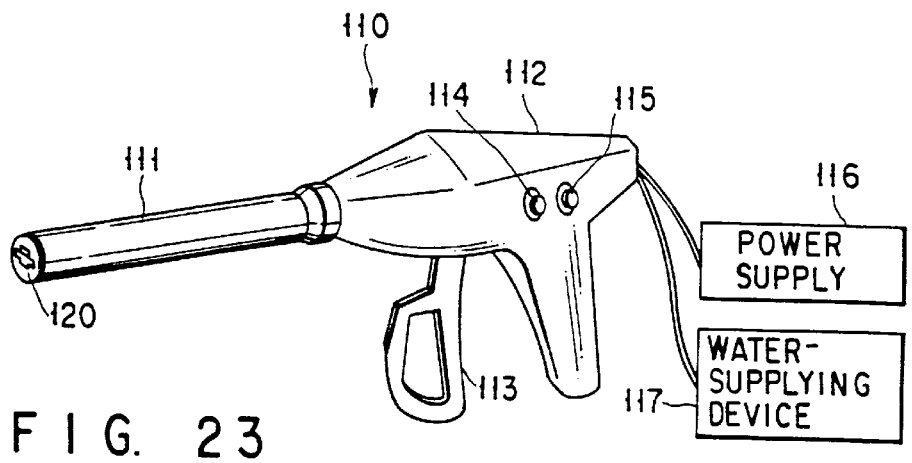
F I G. 23

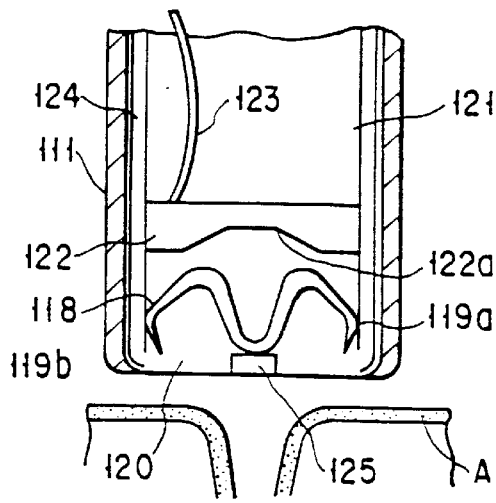 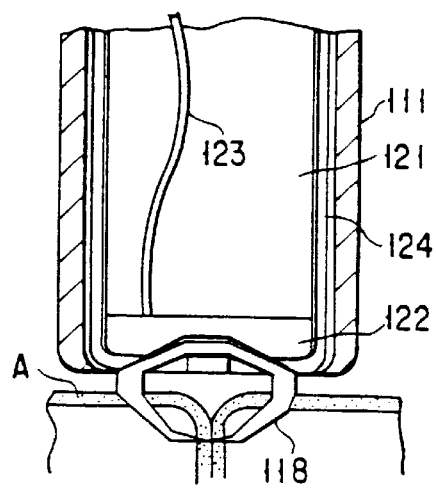
FIG. 24A  FIG. 24B
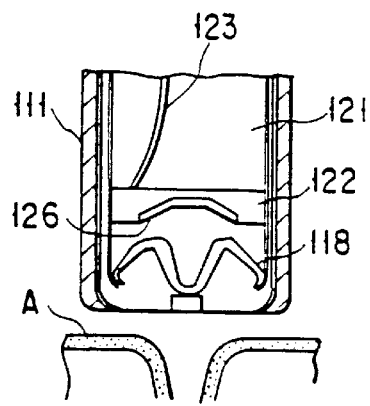 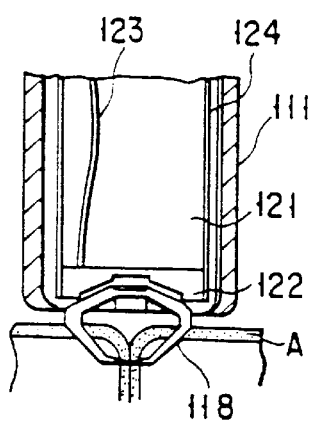 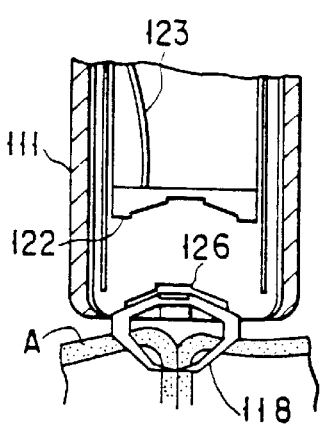
FIG. 25A  FIG. 25B  FIG. 25C
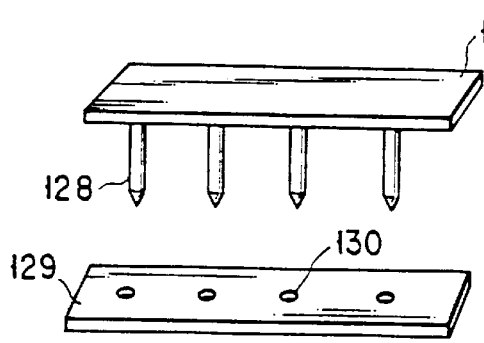
FIG. 26

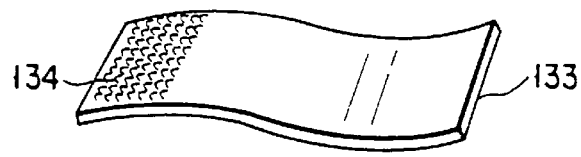
FIG. 30A
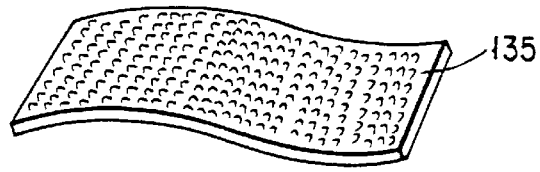
FIG. 30B
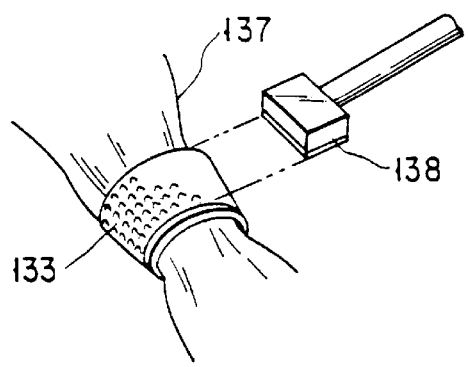
FIG. 31
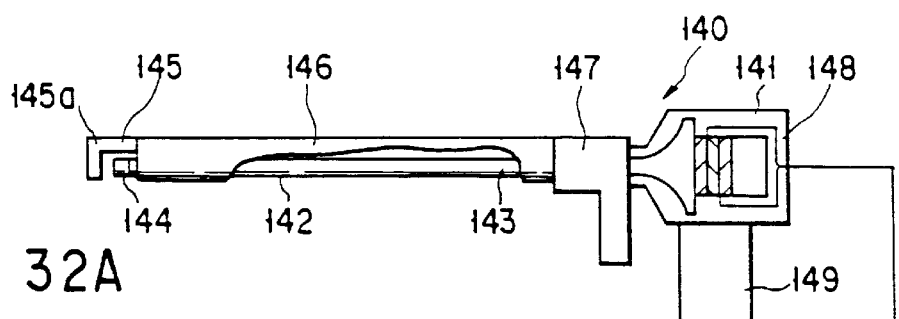
FIG. 32A
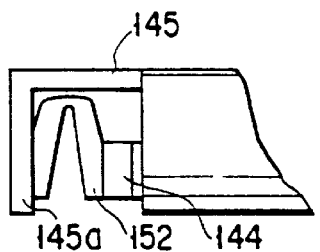
FIG. 32B
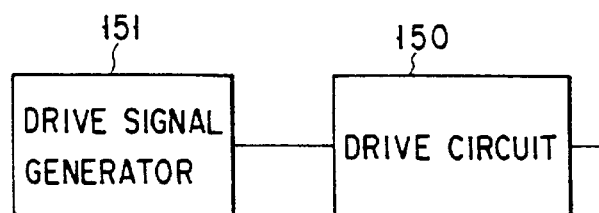

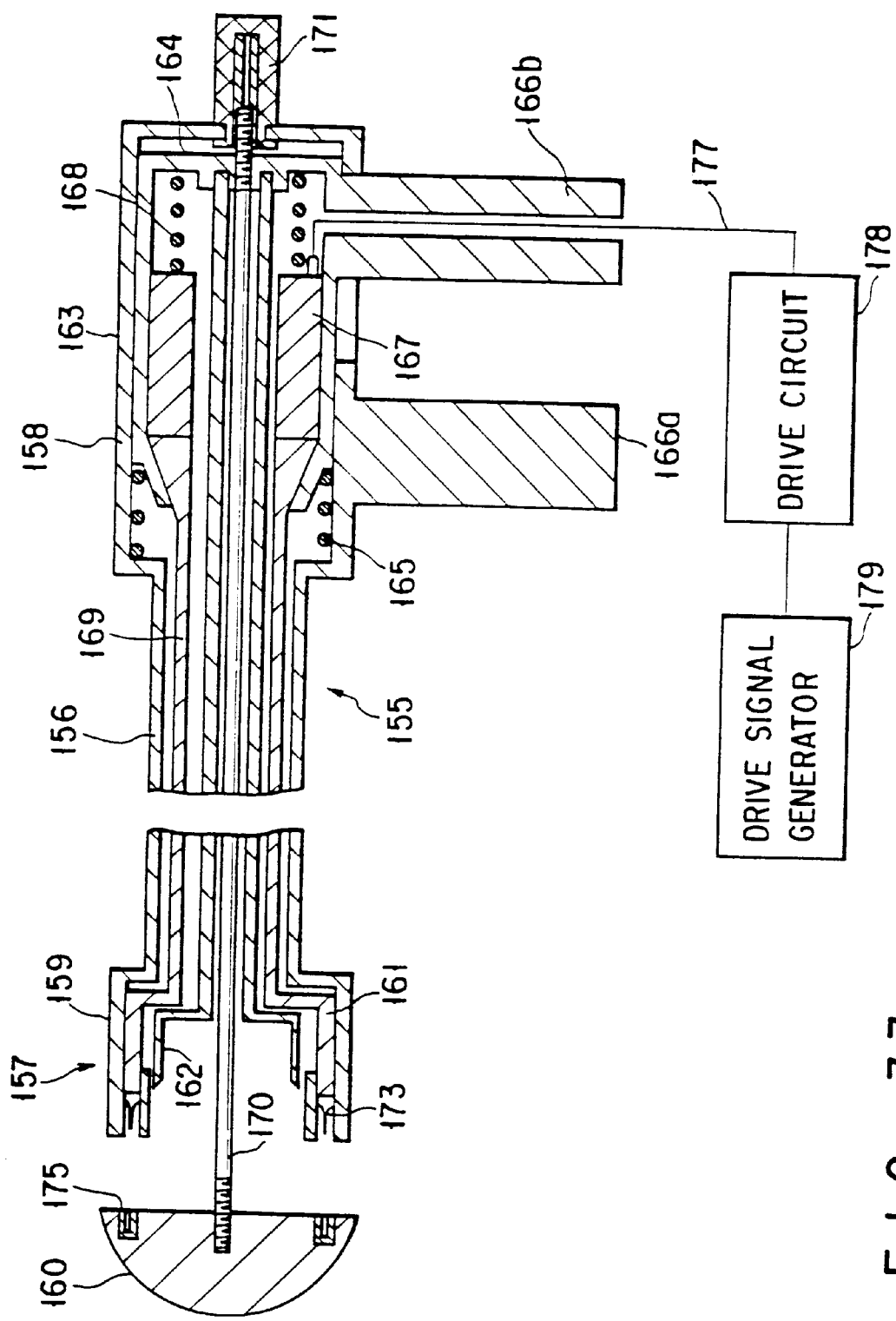
F I G. 33

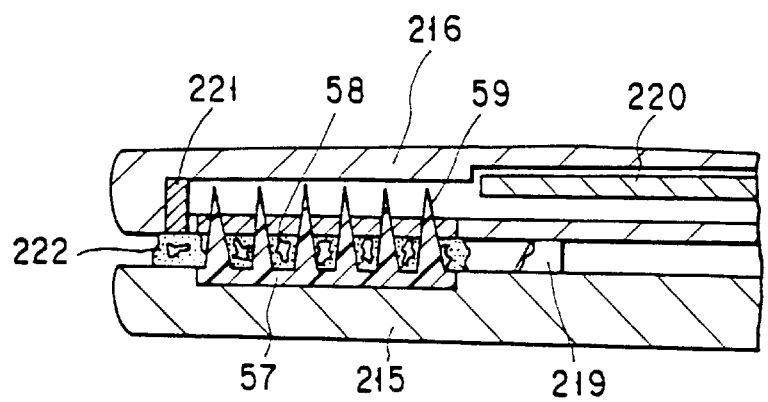
F I G. 46A
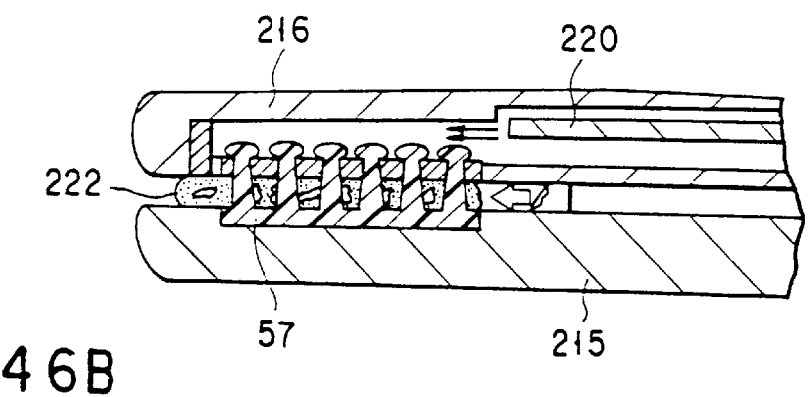
F I G. 46B
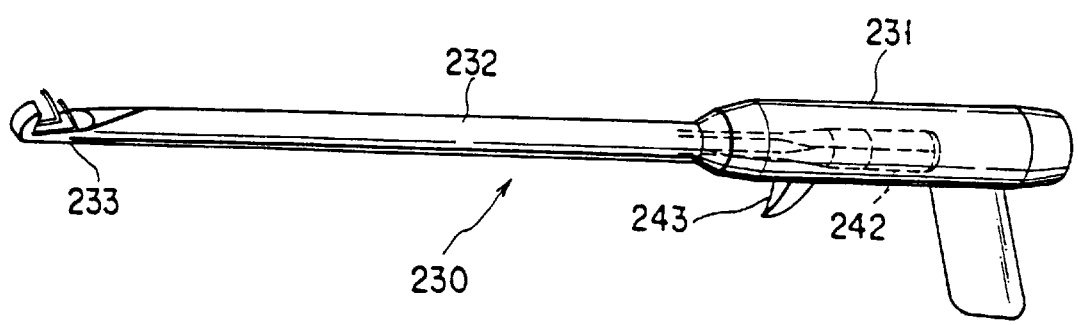
F I G. 47

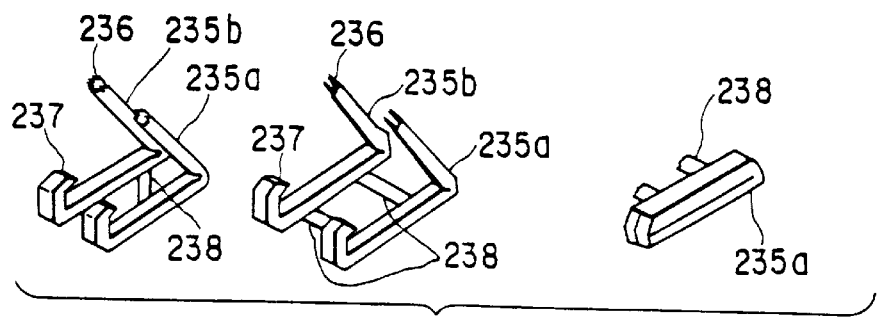
F I G. 52
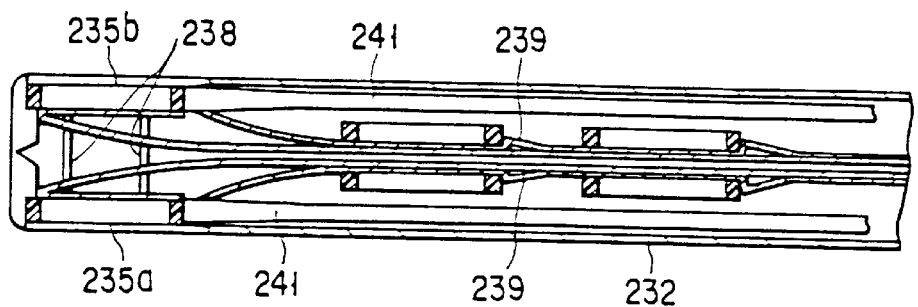
F I G. 53
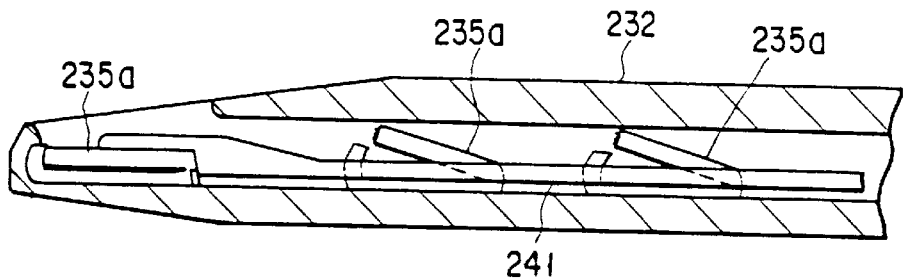
F I G. 54
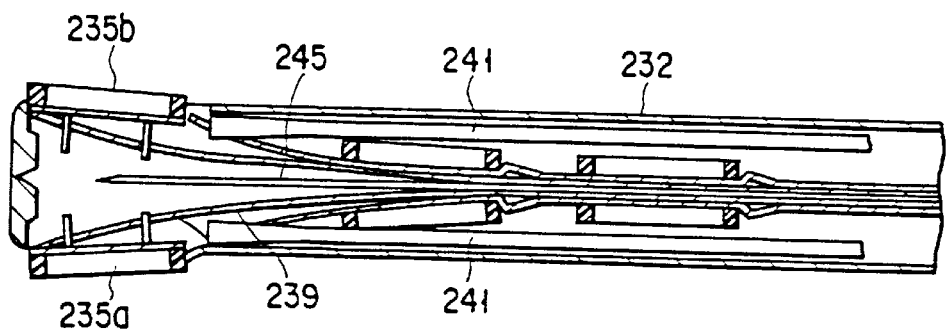
F I G. 55

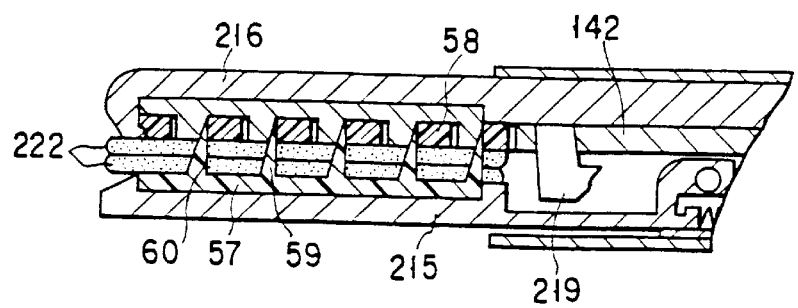
F I G. 58
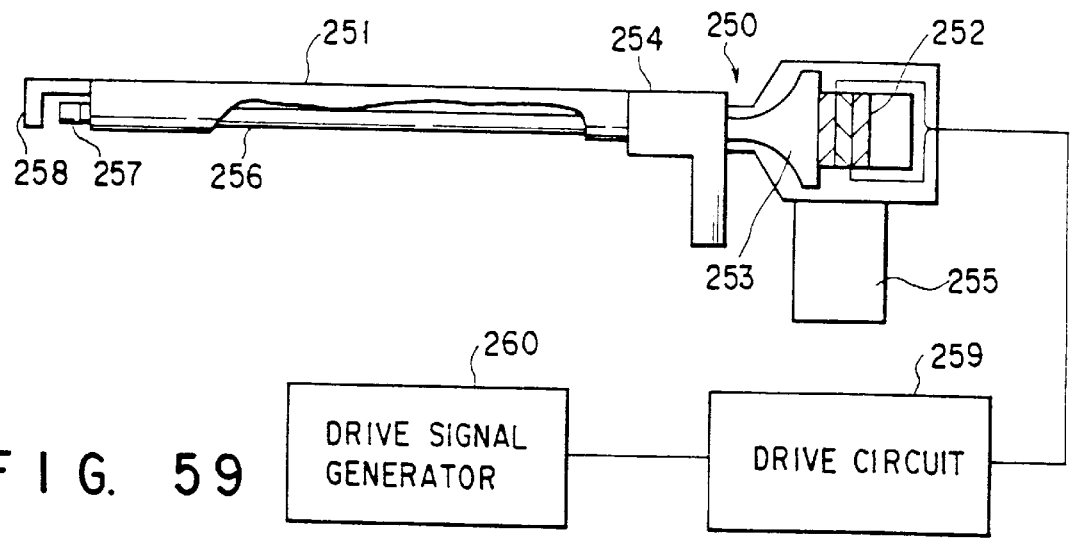
F I G. 59
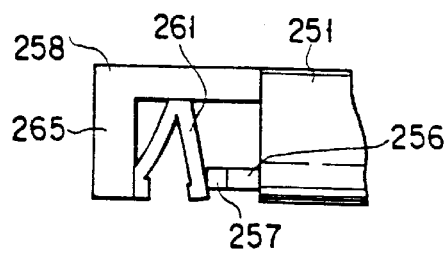
F I G. 60
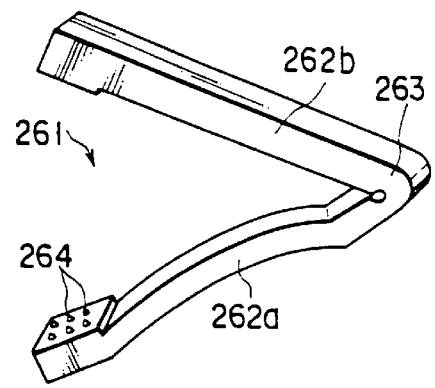
F I G. 61

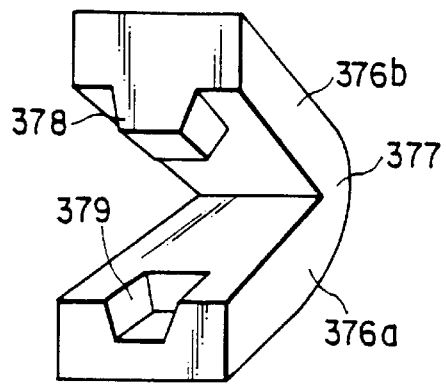
F I G. 90
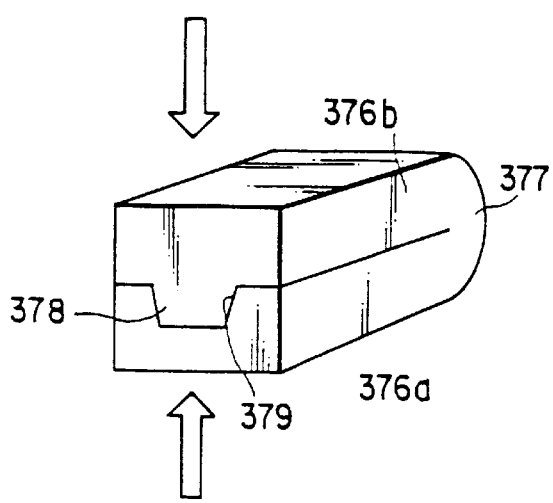
F I G. 91
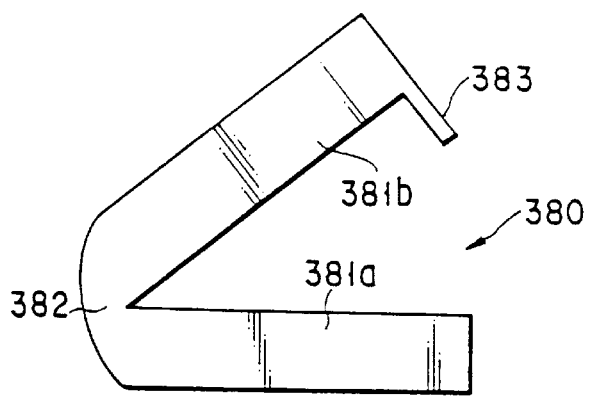
F I G. 92
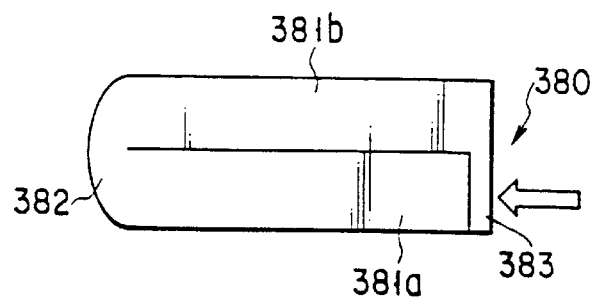
F I G. 93
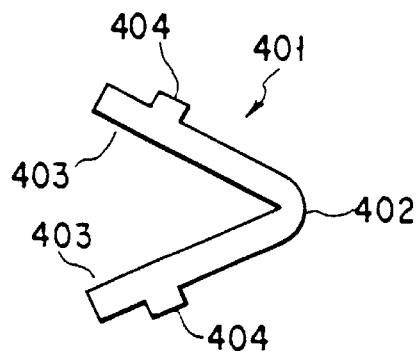
F I G. 94

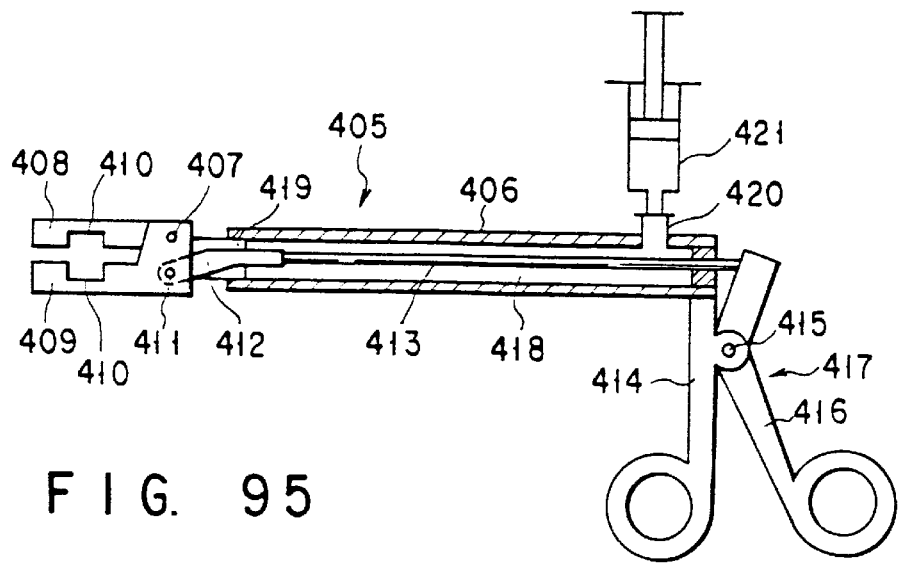
F I G. 95
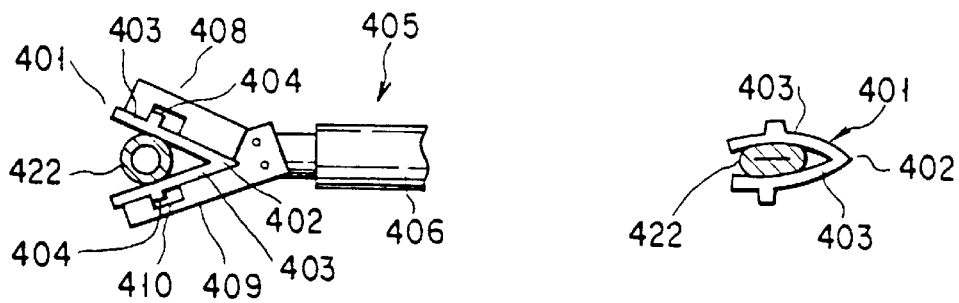
F I G. 96
F I G. 97
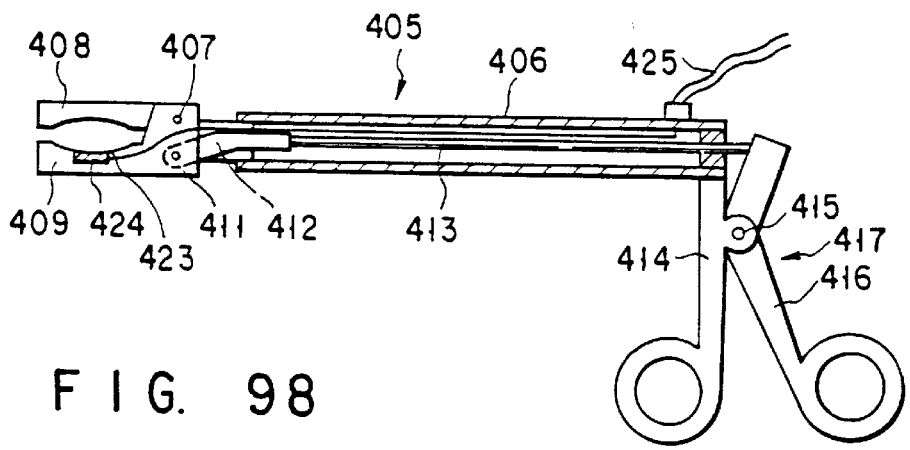
F I G. 98

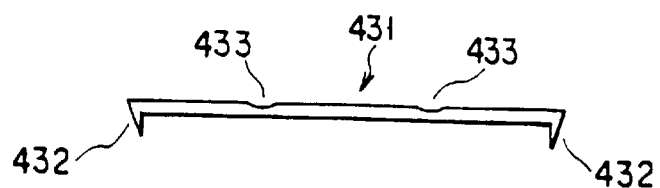
F I G. 99
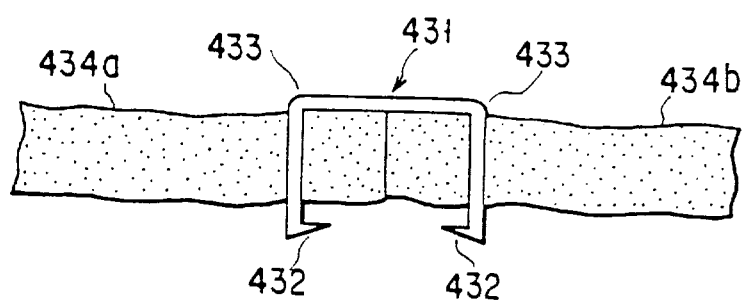
F I G. 100
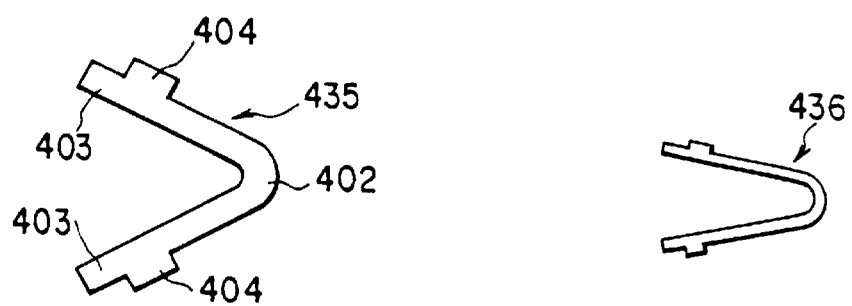
F I G. 101
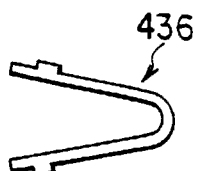
F I G. 102

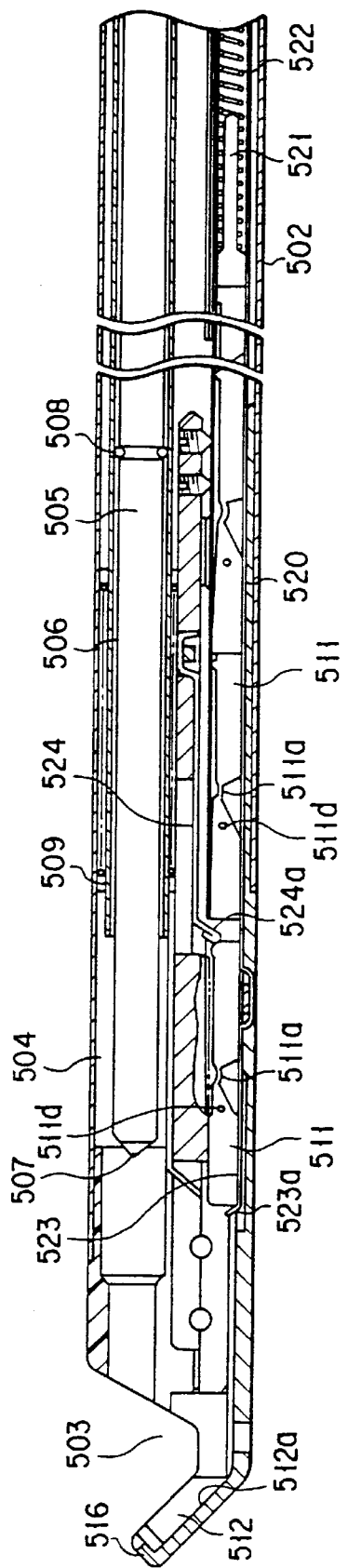
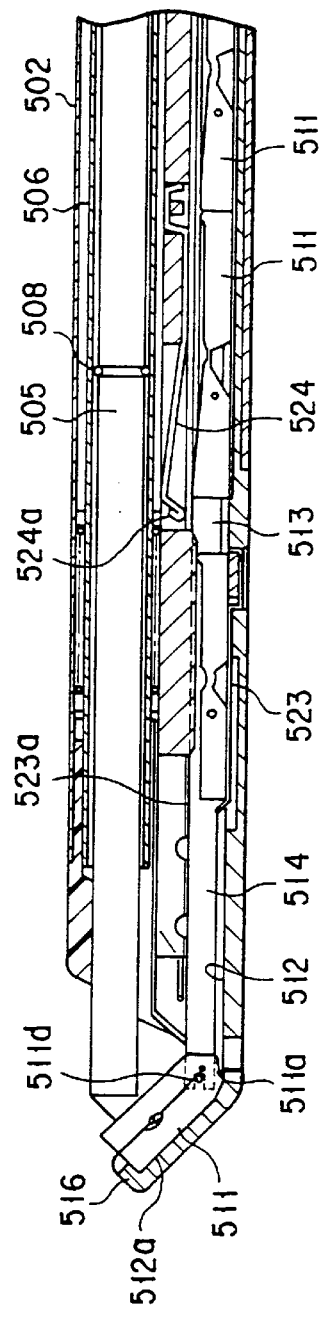
FIG. 104A
FIG. 104B

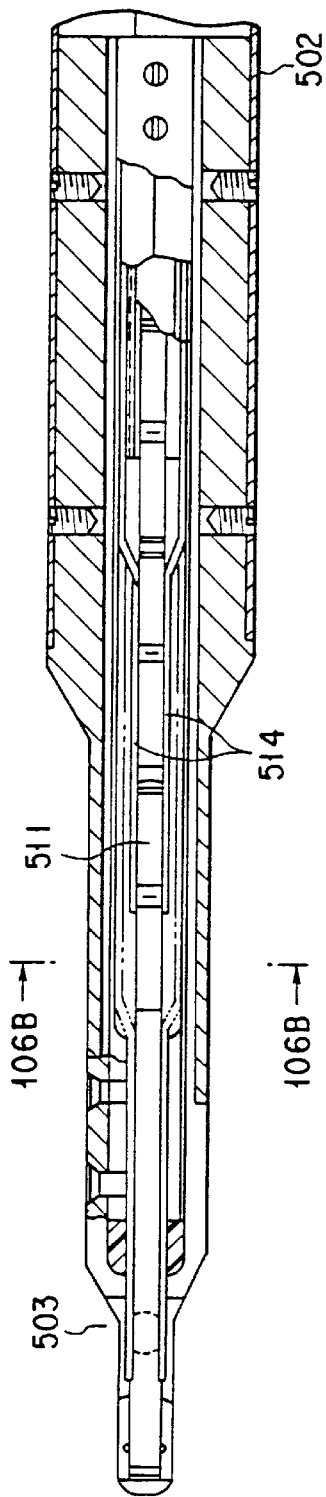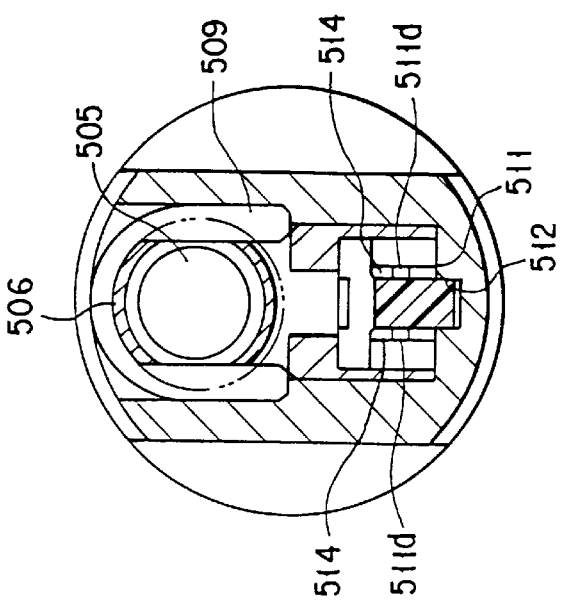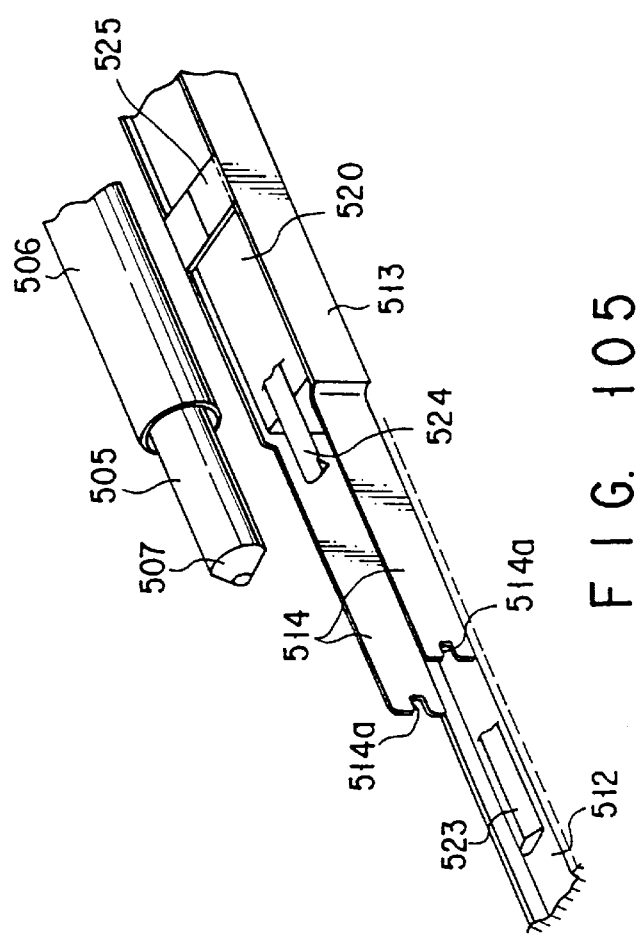

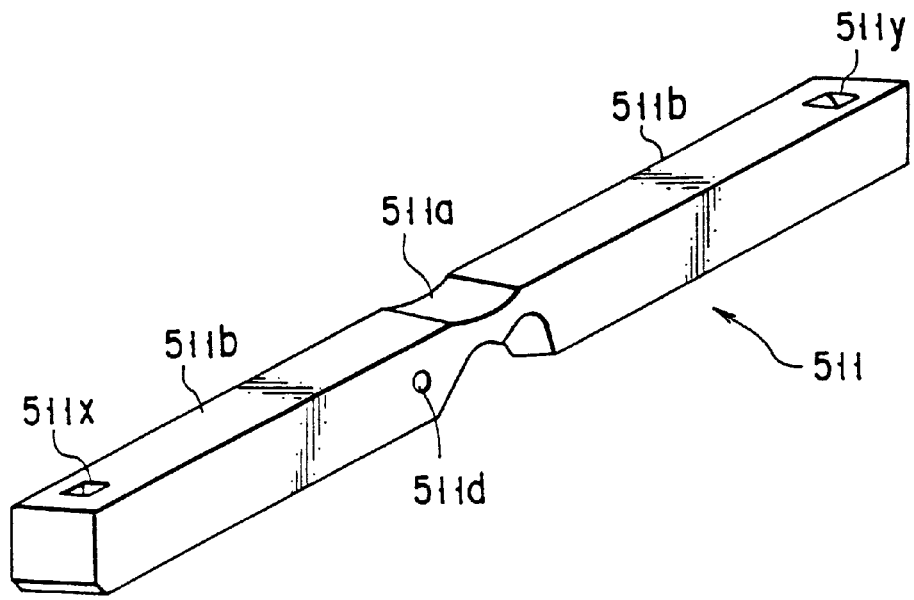
F I G. 110A
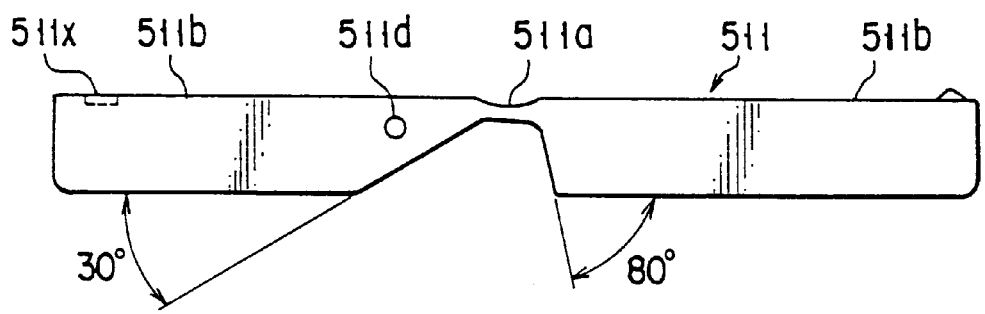
F I G. 110B

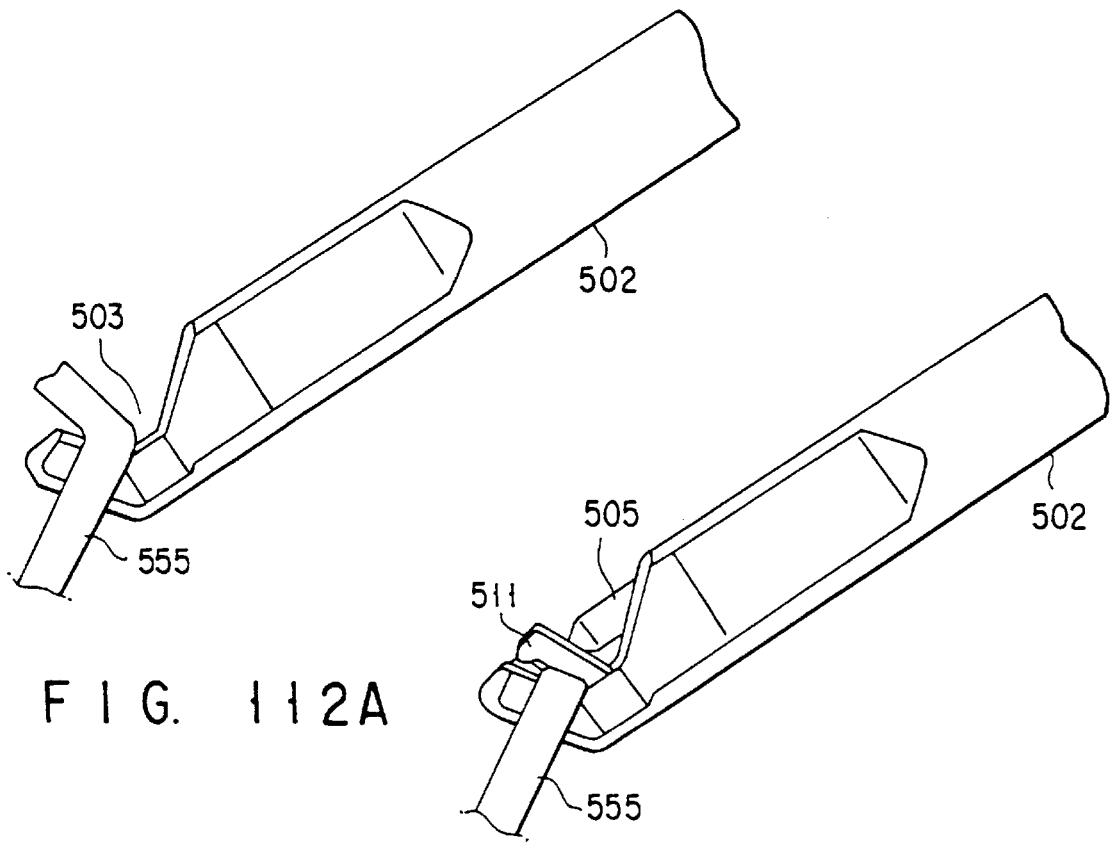
F I G. 112A
F I G. 112B
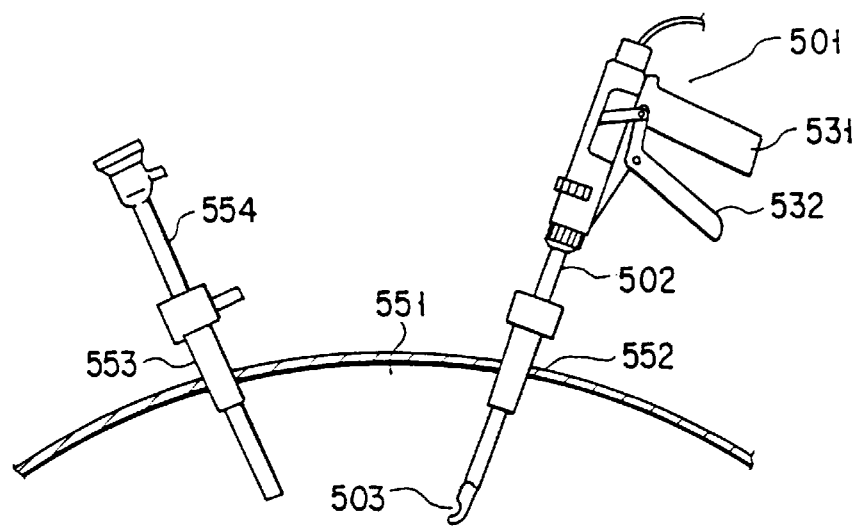
F I G. 113

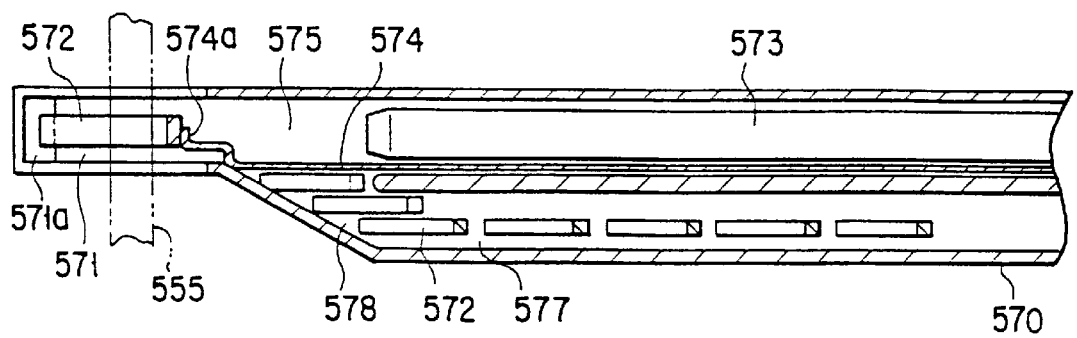
F I G. 120
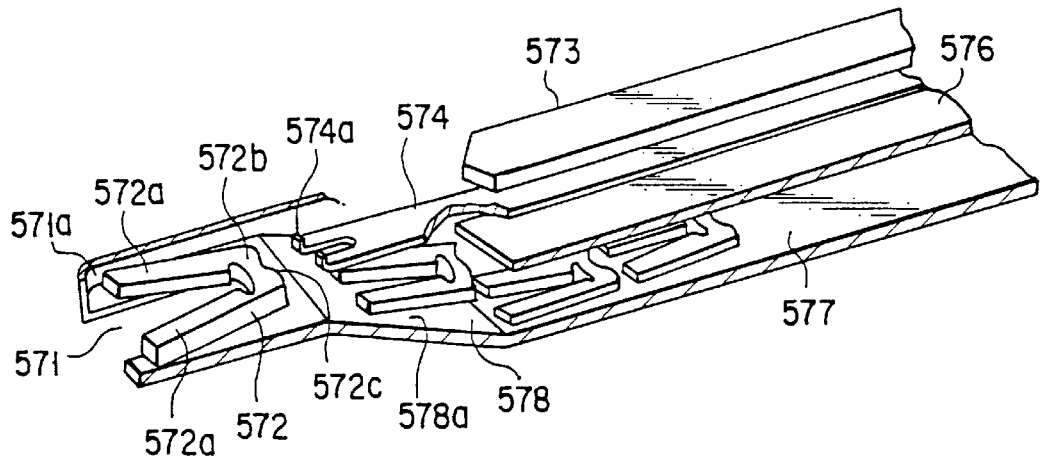
F I G. 121
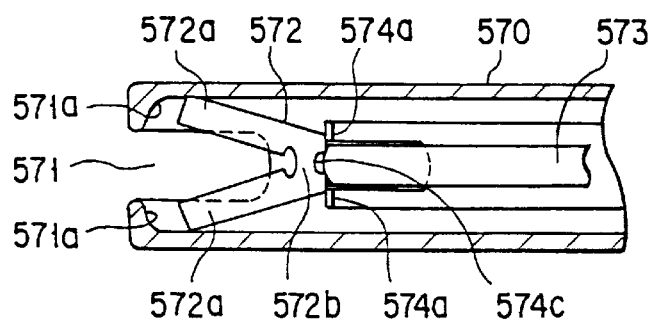
F I G. 122

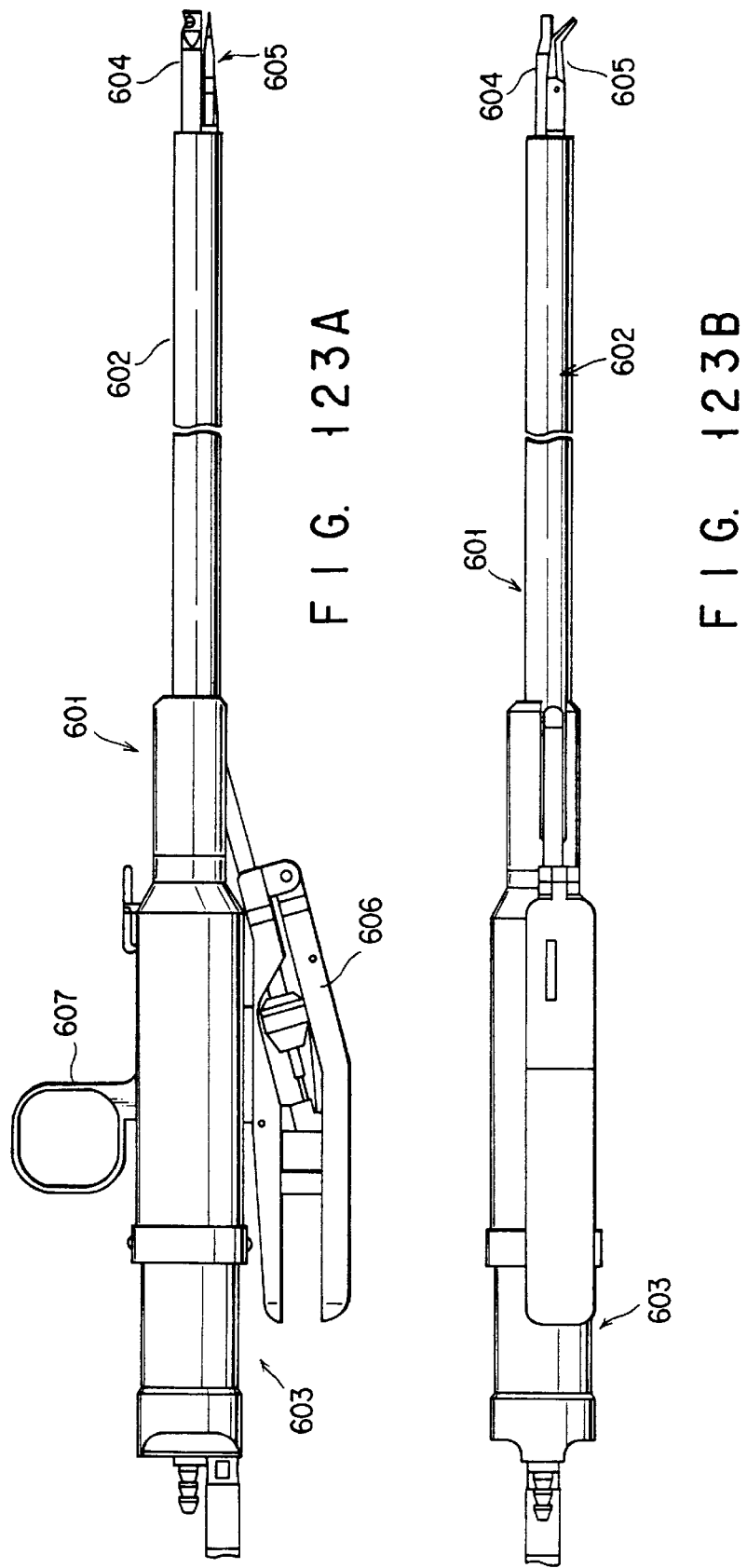

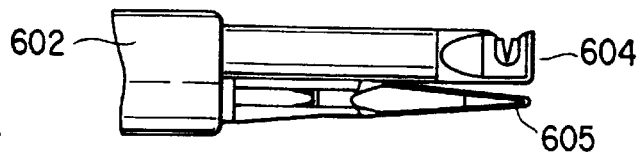
F I G. 124A
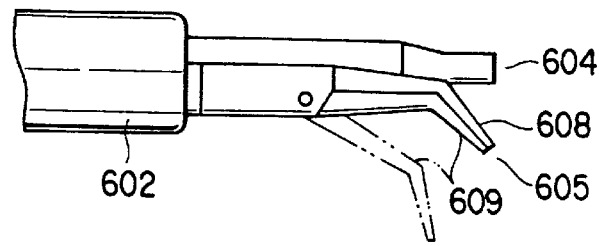
F I G. 124B
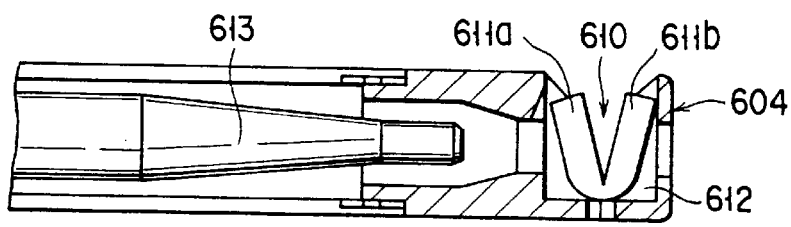
F I G. 125
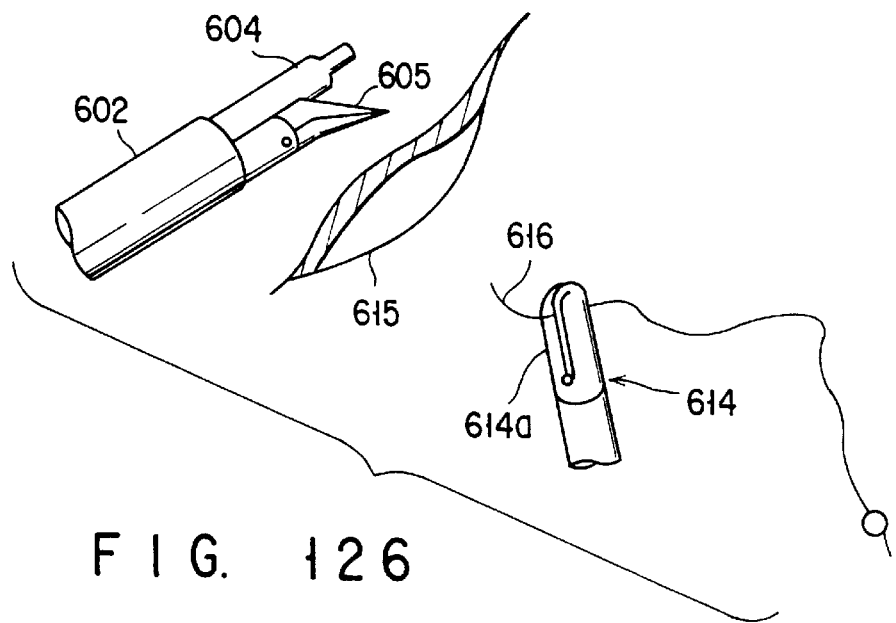
F I G. 126

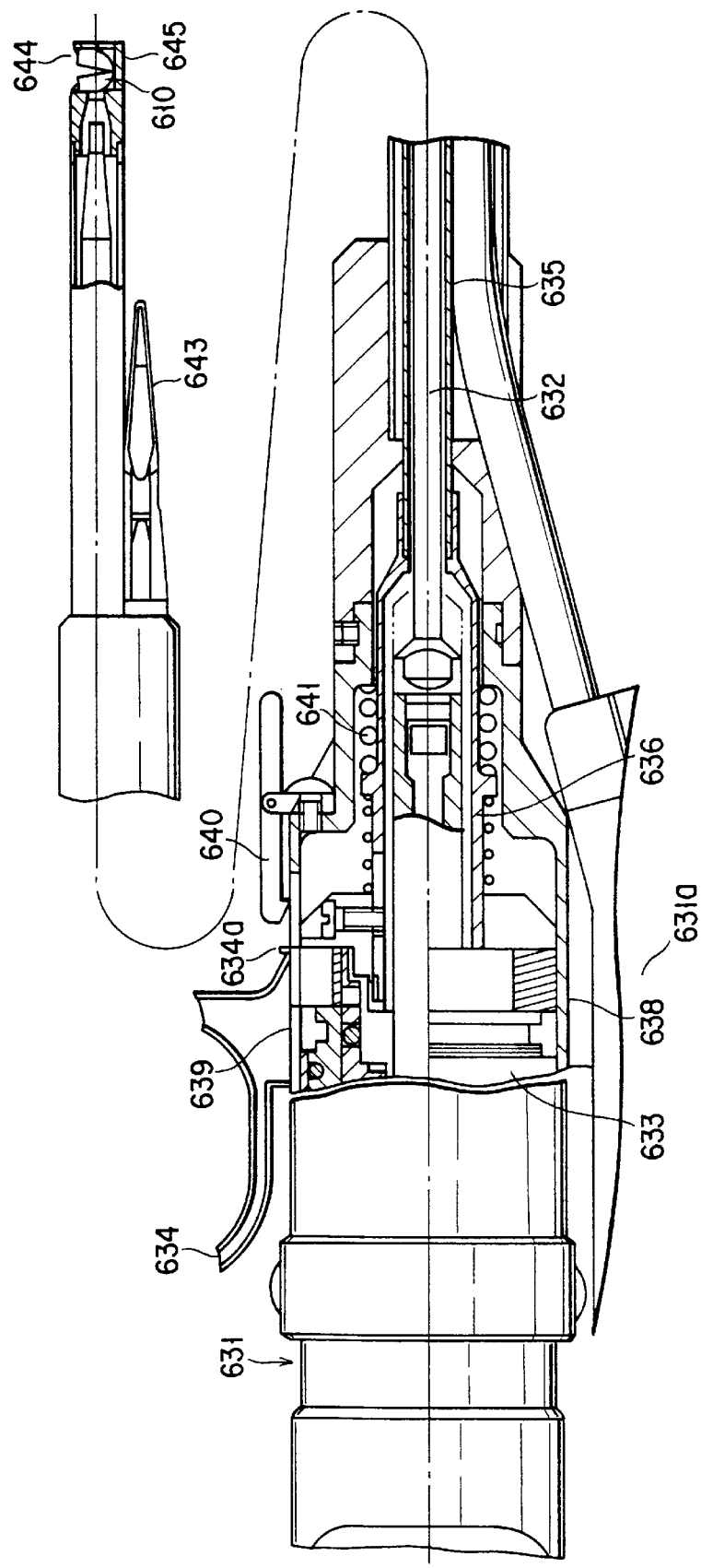
F I G. 137

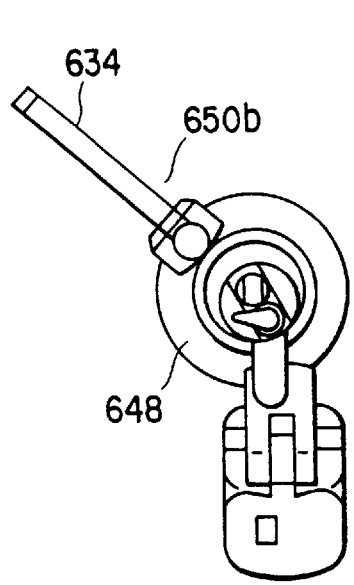
F I G. 141A
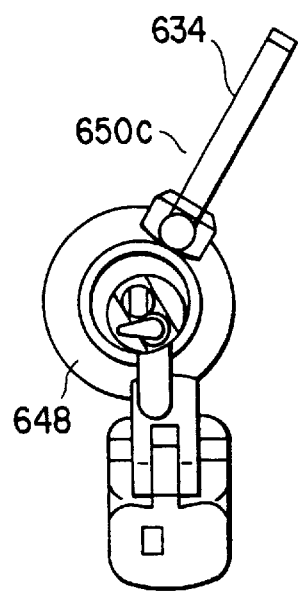
F I G. 141B
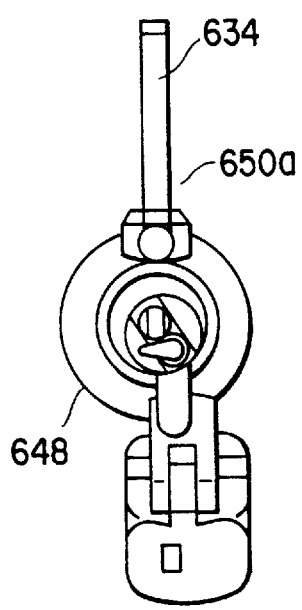
F I G. 141C
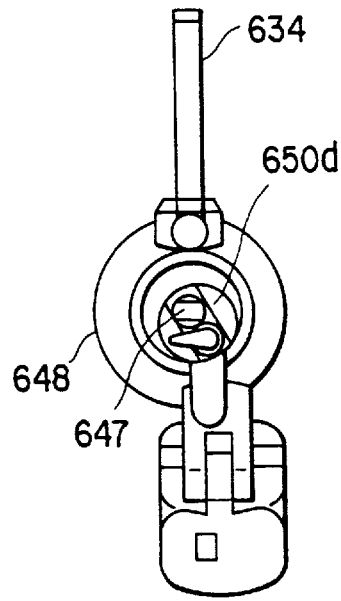
F I G. 141D

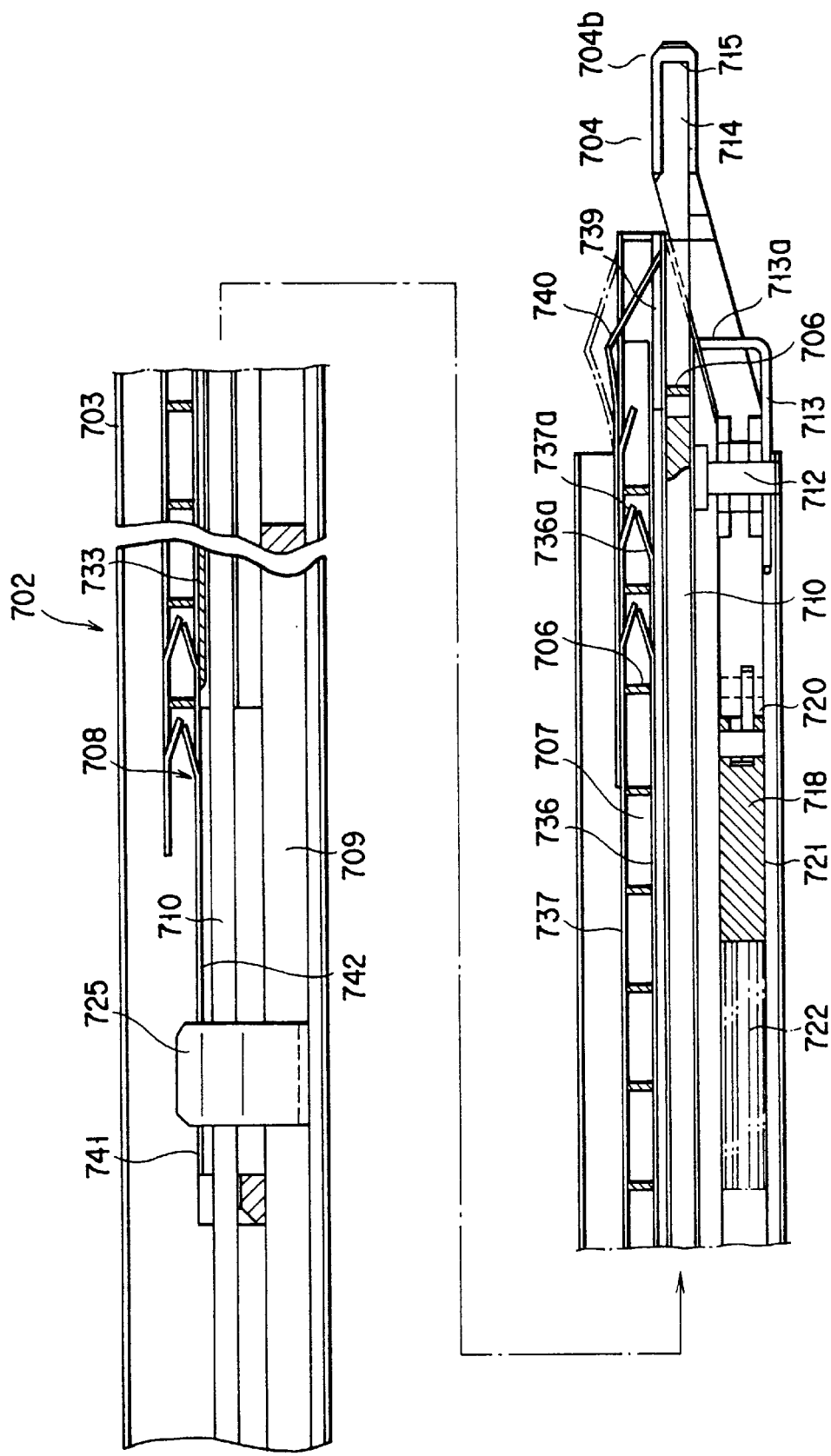
F I G. 145

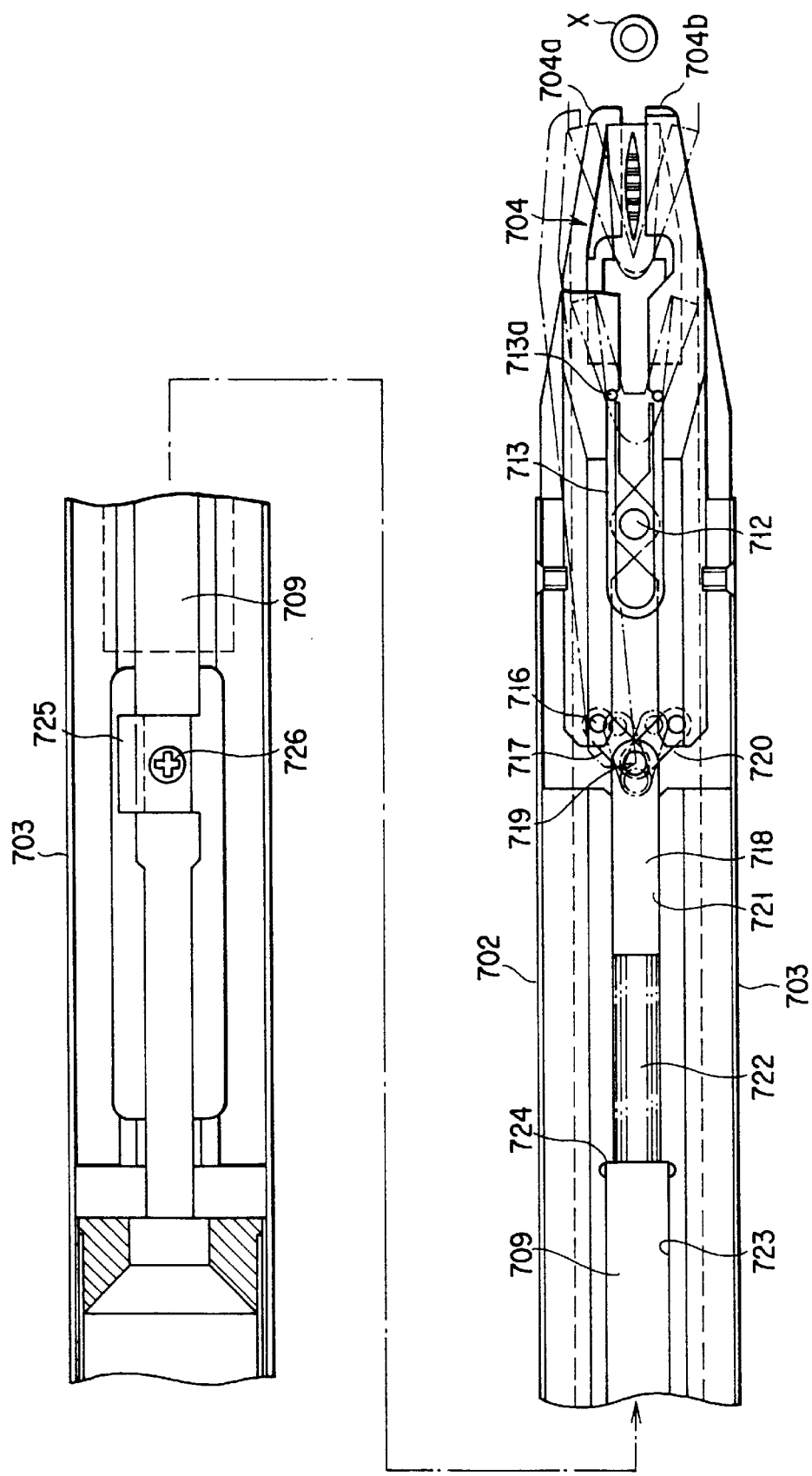
F I G. 146

TISSUE-FIXING SURGICAL INSTRUMENT, TISSUE-FIXING DEVICE, AND METHOD OF FIXING TISSUE

CROSS-REFERENCE TO RELATED APPLICATIONS

This is a Continuation-In-Part of application Ser. No. 08/620,364 filed Mar. 22, 1996, now U.S. Pat. No. 5,797,931, which in turn is a Continuation-In-Part of application Ser. No. 08/384,210 filed Feb. 3, 1995, now U.S. Pat. No. 5,658,300, which in turn is a Continuation of application Ser. No. 08/072,224, filed Jun. 3, 1993 (abandoned).

BACKGROUND OF THE INVENTION

1. Field of the Invention

The present invention relates to a surgical instrument for ligating or suturing tissues, a device for ligating or suturing tissues together, and a method of ligating or suturing tissues.

2. Description of the Related Art

Hitherto, clips applicators of the type shown in Published Unexamined Jpn. Pat. Appln. Publication No. 57-112856 have been used to ligate tubular organs such as blood vessels and bile ducts by using clips. Staplers of the type disclosed in Published Unexamined Jpn. Pat. Appln. Publication No. 3-12126 have been used to suture tubular organs such as intestines by using staples.

Most clips and staplers used for ligating and suturing tissues are made of metal, such as titanium, which is compatible with body tissues. Clips are known which are made of resin capable of being absorbed into body tissues, such as polydioxanone, polylactide, or polyglycolide.

Although the clips and staples are made of metal compatible with tissues, such as titanium, they will remain as foreign bodies in patients. Clips made of resin capable of being absorbed into body tissues are more likely to become loose than those made of metal, because their latching or clamping force is relatively small since it results from the elasticity of the resin.

SUMMARY OF THE INVENTION

The object of this invention is to provide a surgical instrument which can reliably ligate or suture tissues with devices such as clips or staples, a device which can ligate or suture tissues steadfastly, and a method which can reliably ligate or suture tissues.

To attained the object, there are provided the following apparatus, devices and methods according to the present invention:

A surgical instrument for fastening together opposing portions of a body organ, comprising: first support means for supporting the first opposing portion of the body organ; second support means opposing the first support means, for supporting the second opposing portion of the body organ; displacement-preventing means connected to one of the support means for preventing the support means from displacing relative to each other, and made of thermoplastic resin which is softened when heated; and an applicator having holding means for holding at least one of the support means, heating means for heating and softening the displacement-preventing means, and operating means for deforming the displacement-preventing means thus softened, thereby to fix the first and second support means in position to fasten together the opposing portions of the body organ.

A surgical device for fastening together opposing portions of a body organ, comprising: first support means for supporting the first opposing portion of the body organ; second support means opposing the first support means, for supporting the second opposing portion of the body organ; and displacement-preventing means connected to one of the support means for preventing the support means from displacing relative to each other, and made of thermoplastic resin which is softened when heated.

A method of applying a clip to a body organ by means of an applicator, comprising the steps of: preparing a clip comprising a pair of legs and a thermally deformable member, all made of thermoplastic resin; loading the clip in the applicator; placing the body organ between the legs of the clip; heating and softening the thermally deformable member; and closing the legs of the clip, thereby clamping the body organ.

A method of applying a fastener to body tissues by means of an applicator, for fastening the body tissues together, comprising the steps of: preparing a fastener made of thermoplastic resin and having legs; loading the fastener in the applicator; piercing the legs of the fastener through the body tissues; and heating and deforming the legs of the fastener, thereby fastening the body tissues together.

A method of applying a fastener and a retainer to body tissues by means of an applicator, for fastening the body tissues together, comprising the steps of: preparing the fastener and the retainer, both made of thermoplastic resin; loading the fastener and the retainer in the applicator; piercing the legs of the fastener through the body tissues; connecting the legs of the fastener to the retainer; and heating and deforming the legs of the fastener, thereby securing the same to the retainer, thereby fastening the body tissues together.

With the present invention it is possible to clamp a tissue with a device made of thermoplastic resin, such as a clip or a staple, thereby achieving reliable ligation or suture of the tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 18A and 18B are perspective views, both showing the staple applied by the stapler of FIG. 16 and also explaining how to suture a organ tissue with this staple;

FIG. 19 is a partially sectional side view showing the distal end portion of a stapler which is a sixth embodiment of the present invention;

FIG. 20 is a perspective view showing a stapler which is a seventh embodiment of the invention;

FIG. 21 is an exploded view showing the suture section of the stapler shown in FIG. 20;

FIG. 22 is an exploded view of a stapler which is applied by the stapler shown in FIG. 20;

FIG. 23 is a perspective view of a stapler according to an eighth embodiment of this invention;

FIGS. 24A and 24B are cross-sectional views showing the distal end portion of the stapler shown in FIG. 23 and explaining how the stapler applies a staple to fasten body walls together;

FIGS. 25A, 25B, and 25C are cross-sectional views showing a modification of the stapler shown in FIG. 23;

FIG. 26 is an exploded view showing a first modification of the staple which is applied by the stapler shown in FIG. 12;

FIGS. 30A and 30B are perspective views showing a fourth modification of the stapler which is applied by the stapler;

FIG. 31 is a view explaining how the stapler shown in FIGS. 30A and 30B is used to ligate a tubular organ;

FIG. 32A is a diagram schematically showing a clip applicator which is a ninth embodiment of the present invention;

FIG. 32B is a side view of the distal end portion of the clip applicator shown in FIG. 32A;

FIG. 33 is a schematic representation of a stapler which is a tenth embodiment of the present invention;

FIGS. 46A and 46B are cross-sectional view showing the distal end portions and explaining how the stapler is manipulated to apply a plurality of staples;

FIG. 47 is a perspective view showing a clip applicator which is a fifteenth embodiment of the present invention;

FIG. 52 is a perspective view showing clips to be applied by the applicator of FIG. 48;

FIG. 53 is a diagram explaining how to manipulate the clip applicator of FIG. 48;

FIG. 54 is another diagram explaining how to manipulate the clip applicator of FIG. 48;

FIG. 55 is still another diagram explaining how to manipulate the clip applicator of FIG. 48;

FIG. 58 is a sectional view of the distal end portion of the stapler shown in FIG. 56, explaining how the stapler applies staples;

FIG. 59 is a diagram schematically illustrating a clip applicator according to a seventeenth embodiment of this invention;

FIG. 60 is a side view showing the distal end portion of the clip applicator shown in FIG. 59;

FIG. 61 is a perspective view showing a clip to be applied by the applicator of FIG. 59;

FIG. 90 is a perspective view showing a clip in open state, which is a thirty-fifth embodiment of the present invention;

FIG. 91 is a perspective view showing the clip (FIG. 90) in closed state;

FIG. 92 is a side view illustrating a clip in open state, which is a thirty-sixth embodiment of the present invention;

FIG. 93 is a side view showing the clip (FIG. 92) in closed position;

FIG. 94 is a side view showing a clip according to a thirty-seventh embodiment of the present invention;

FIG. 95 is a longitudinal sectional view showing a clip applicator which is the thirty-seventh embodiment of the invention and which is designed to apply the clip shown in FIG. 94;

FIG. 96 is a side view illustrating the clip-holding section of the applicator shown in FIG. 95;

FIG. 97 is a side view showing the clip (FIG. 94) which is clamping a tubular organ;

FIG. 98 is a longitudinal sectional view showing a clip applicator which is a thirty-eighth embodiment of the invention;

FIG. 99 is a side view showing a clip according to a thirty-ninth embodiment of the present invention which is applied by the clip applicator;

FIG. 100 is a view explaining how the clip of FIG. 99 stitches together two tissues;

FIG. 101 is a side view of a clip which is a fortieth embodiment of the present invention;

FIG. 102 is a side view of a clip which is a forty-first embodiment of the present invention;

FIG. 104A is a longitudinal cross-sectional view showing an initial state of use of an elongated portion according to the forty-second embodiment;

FIG. 104B is a longitudinal cross-sectional view showing a clipping state of the elongated portion according to the forty-second embodiment;

FIG. 105 is a perspective view showing an inner structure of the distal end portion of the elongated portion according to the forty-second embodiment;

FIG. 106A is a longitudinal cross-sectional view showing the distal end portion of the elongated portion according to the forty-second embodiment;

FIG. 106B is a cross-sectional view cut along the line 106B—106B of FIG. 106A;

FIG. 110A is a perspective view showing a clip used for the applicator according to the forty-second embodiment;

FIG. 110B is a side view showing the clip used for the applicator according to the forty-second embodiment;

FIG. 112A to FIG. 112B are views explaining states of use of the applicator according to the forty-second embodiment;

FIG. 113 is a view explaining a state of use of the forty-second embodiment;

FIG. 114 is a perspective view showing a clip and the attached portion thereof according to a modified version of the forty-second embodiment;

FIG. 115 is a side view showing a clip according to a forty-third embodiment;

FIG. 116A is a side view showing a clip according to a forty-fourth embodiment;

FIG. 116B is a front view showing a clip according to the forty-fourth embodiment;

FIG. 117 is a perspective view showing a distal end of an applicator according to the forty-fourth embodiment;

FIG. 118A is a cross-sectional view showing an initial state of a distal end portion of the applicator according to the forty-fourth embodiment;

FIG. 118B is a cross-sectional view showing a state of use of the distal end portion of the applicator according to the forty-fourth embodiment;

FIG. 119A is a side view of a modified version of the clip according to the forty-fourth embodiment;

FIG. 119B is a front view of the modified version of the clip according to the forty-fourth embodiment;

FIG. 119C is a perspective view showing the clip according to the forty-fourth embodiment;

FIG. 120 is a cross-sectional view showing a distal end portion of the applicator according to a forty-fifth embodiment;

Figure 127:
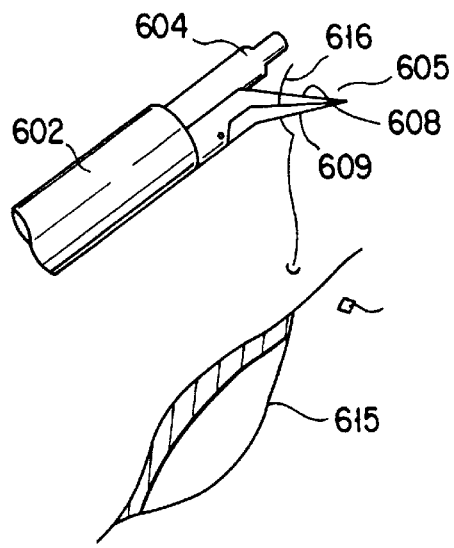
Figure 128:
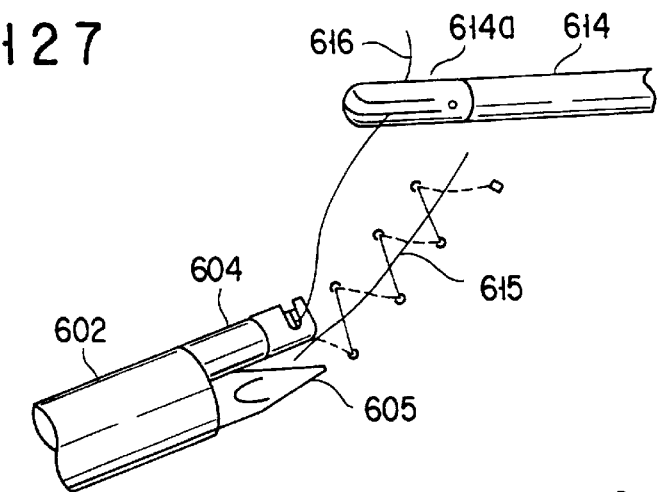
Figure 129:
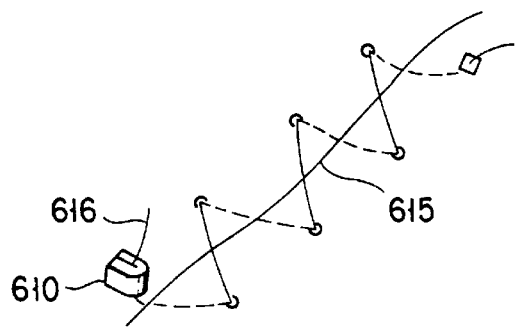
Figure 130:
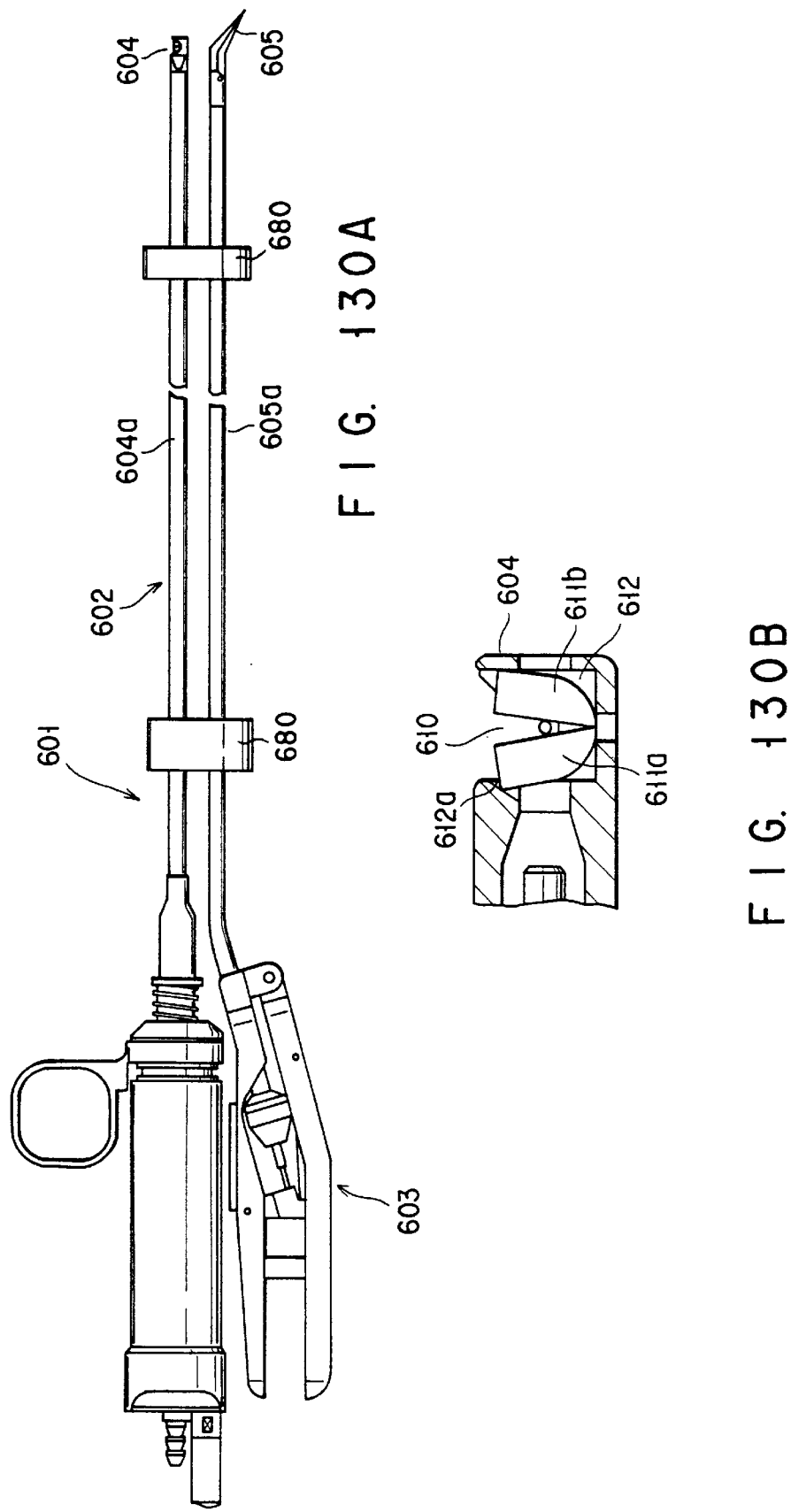
Figure 131:
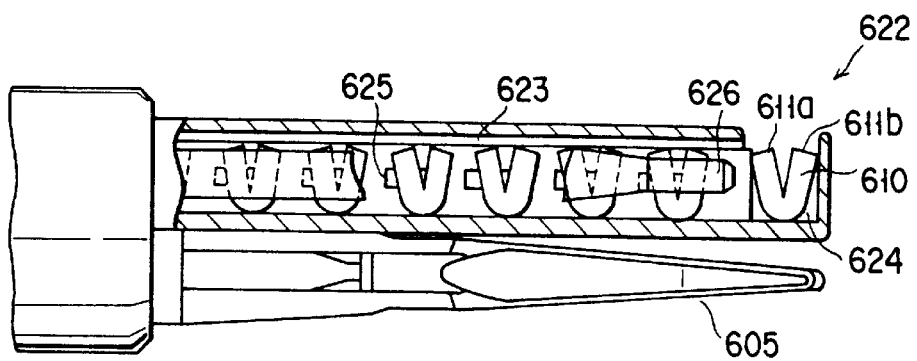
Figure 132:
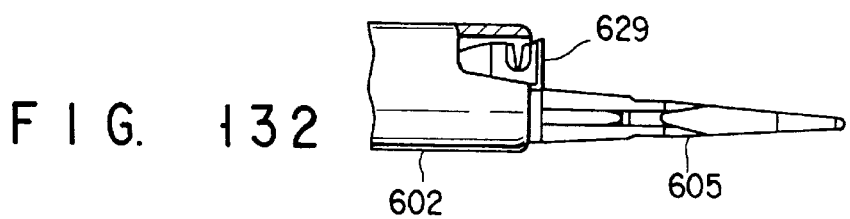
Figure 133:
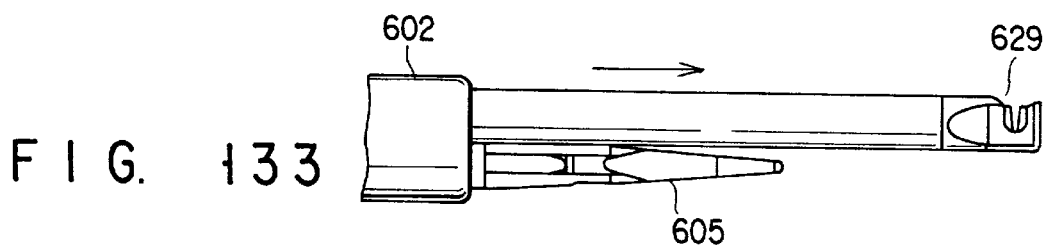
Figure 134:
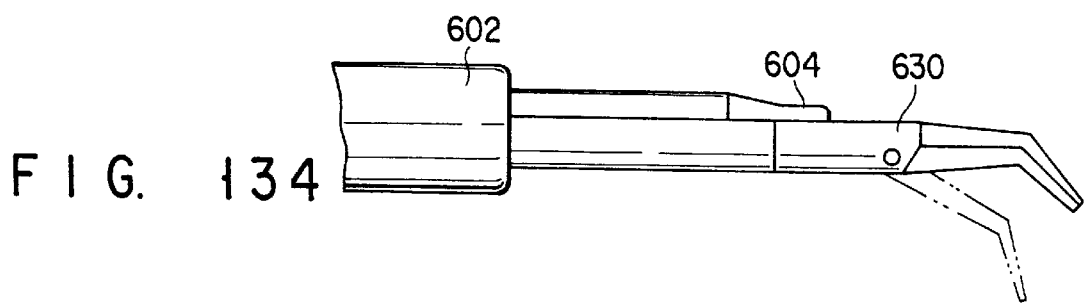
Figure 135:
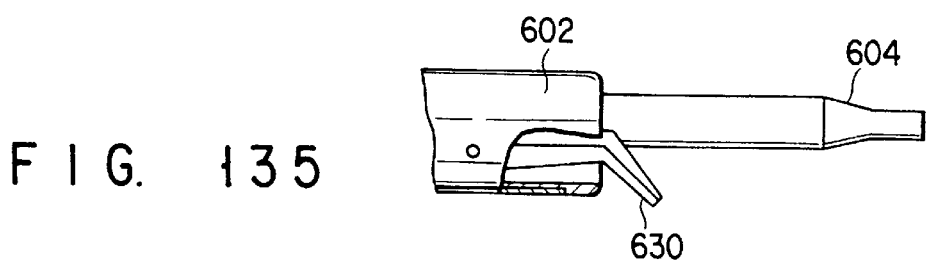
Figure 136:
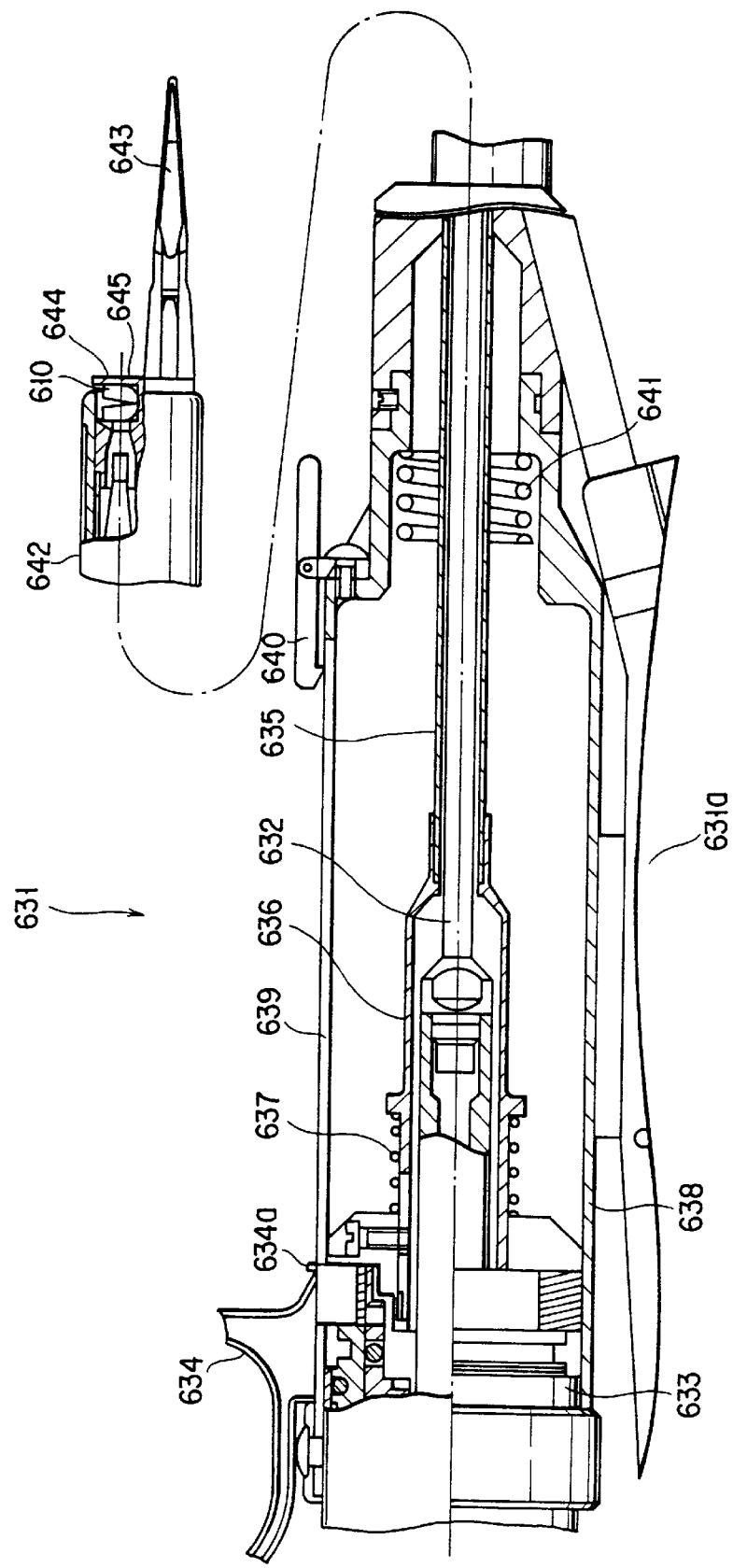
Figure 138:
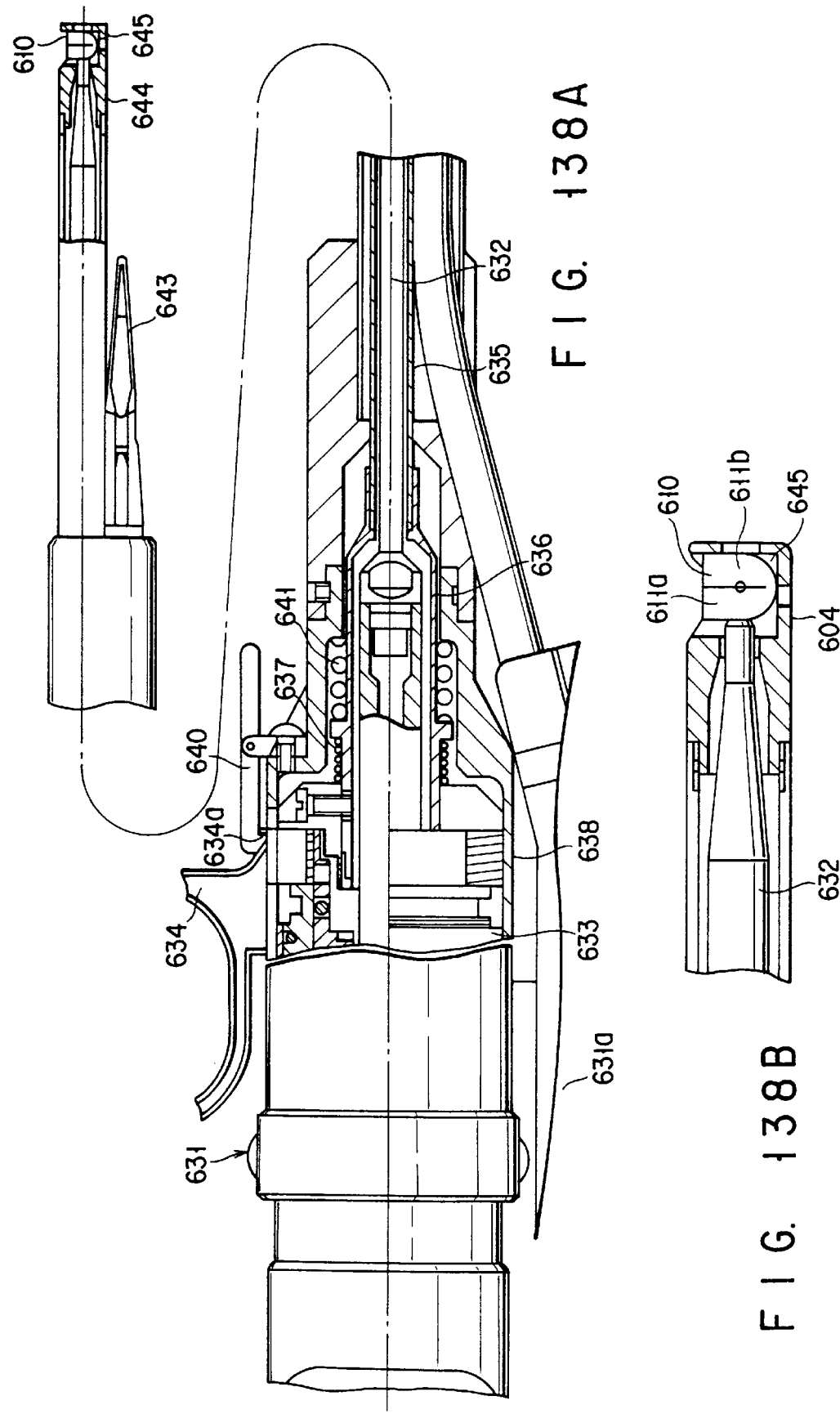
Figure 139:
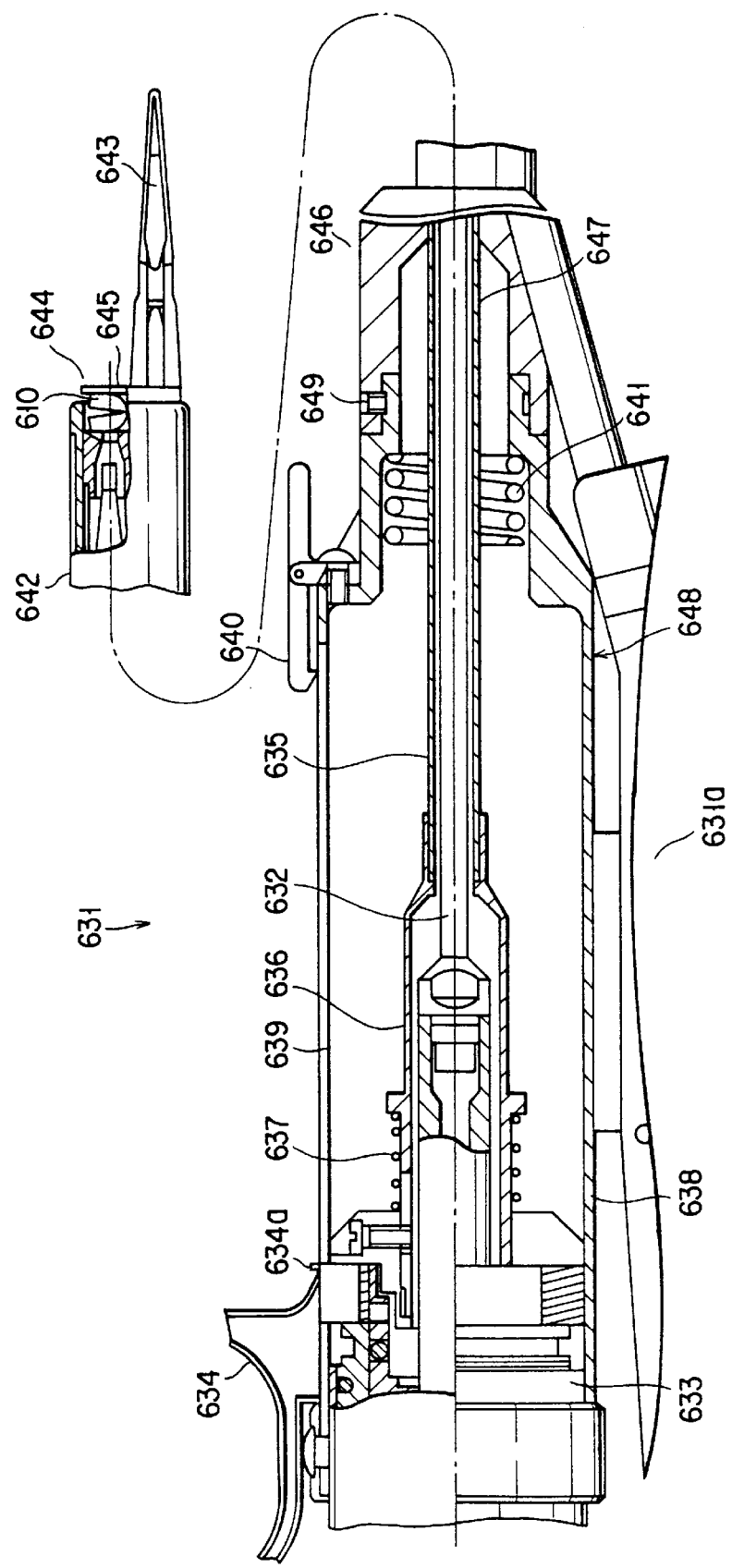
Figure 140:
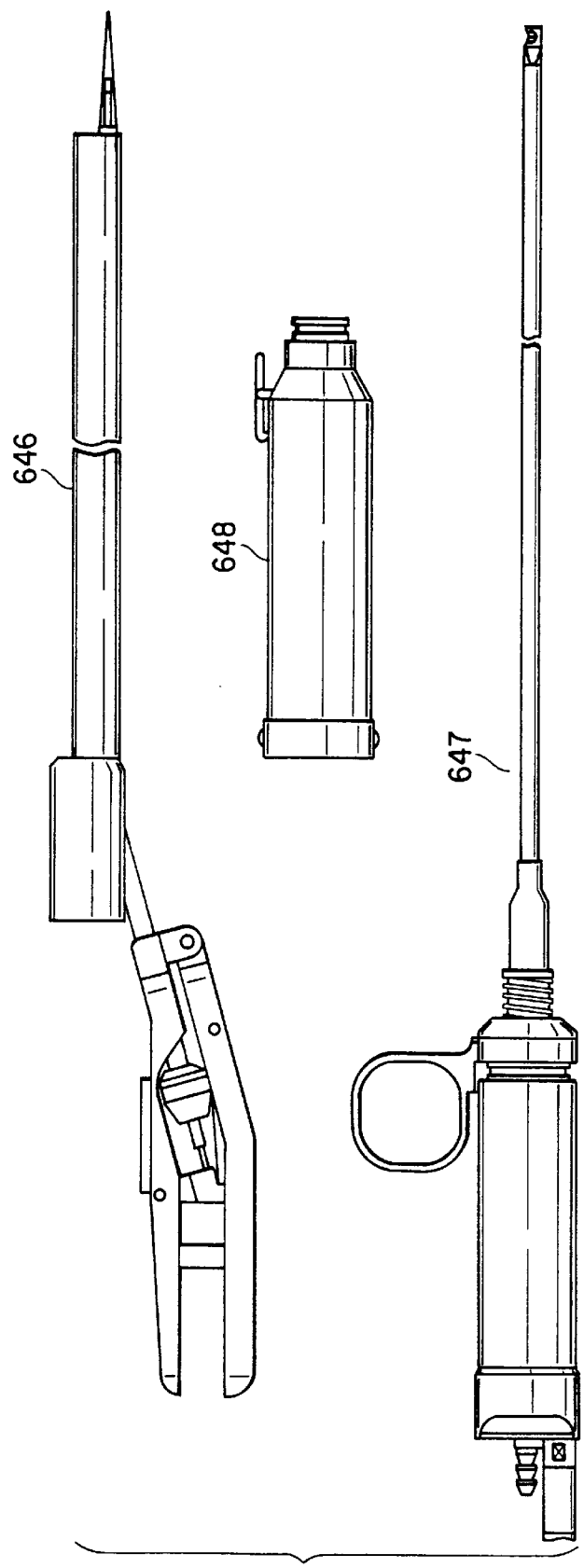
Figure 142A:
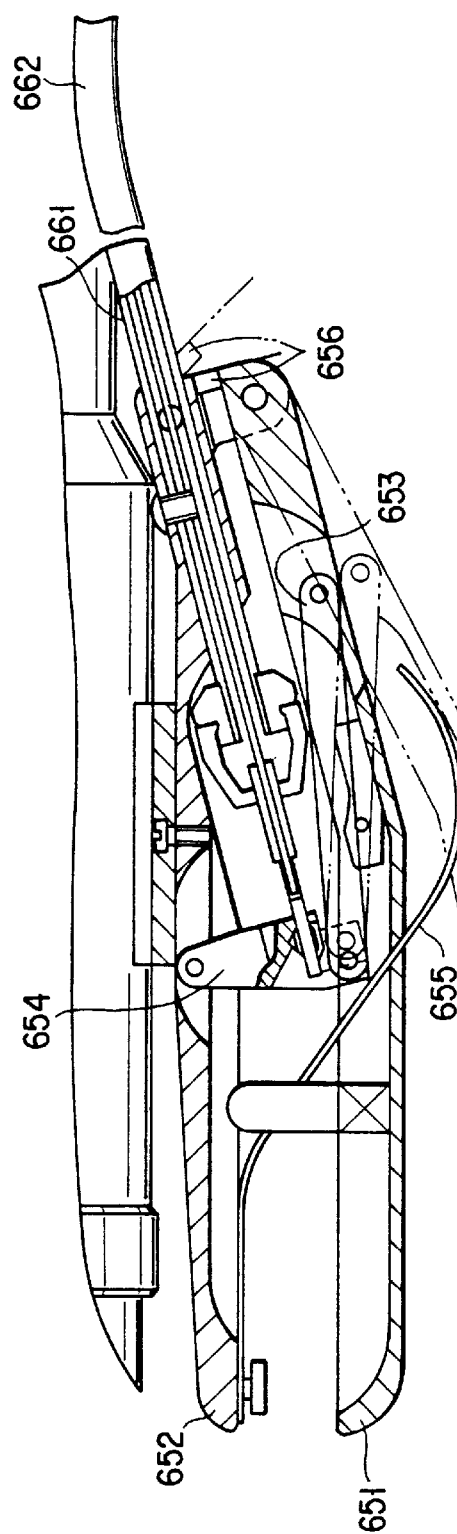
Figure 142B:
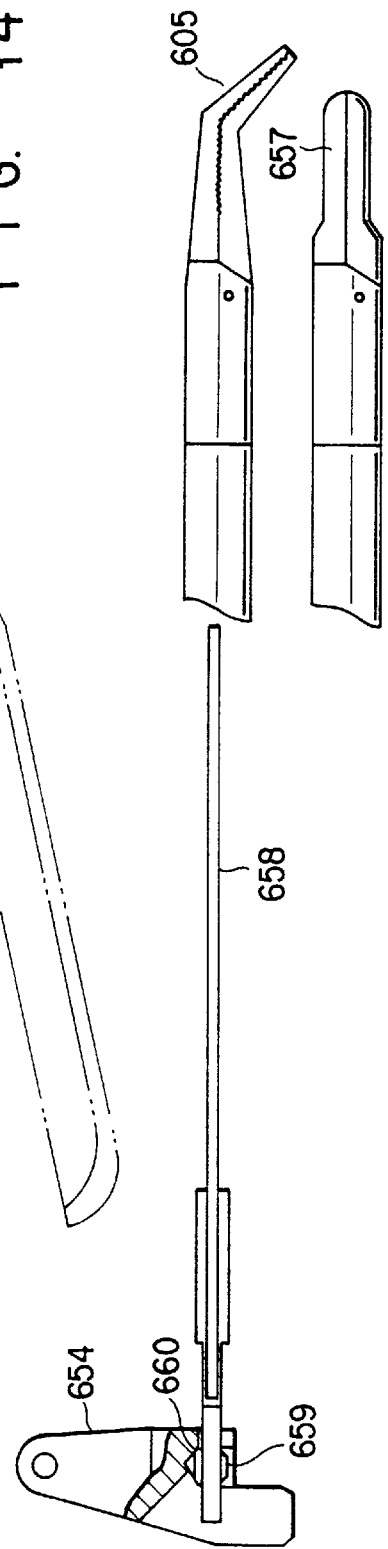
Figures 143A, 143B, 143C:
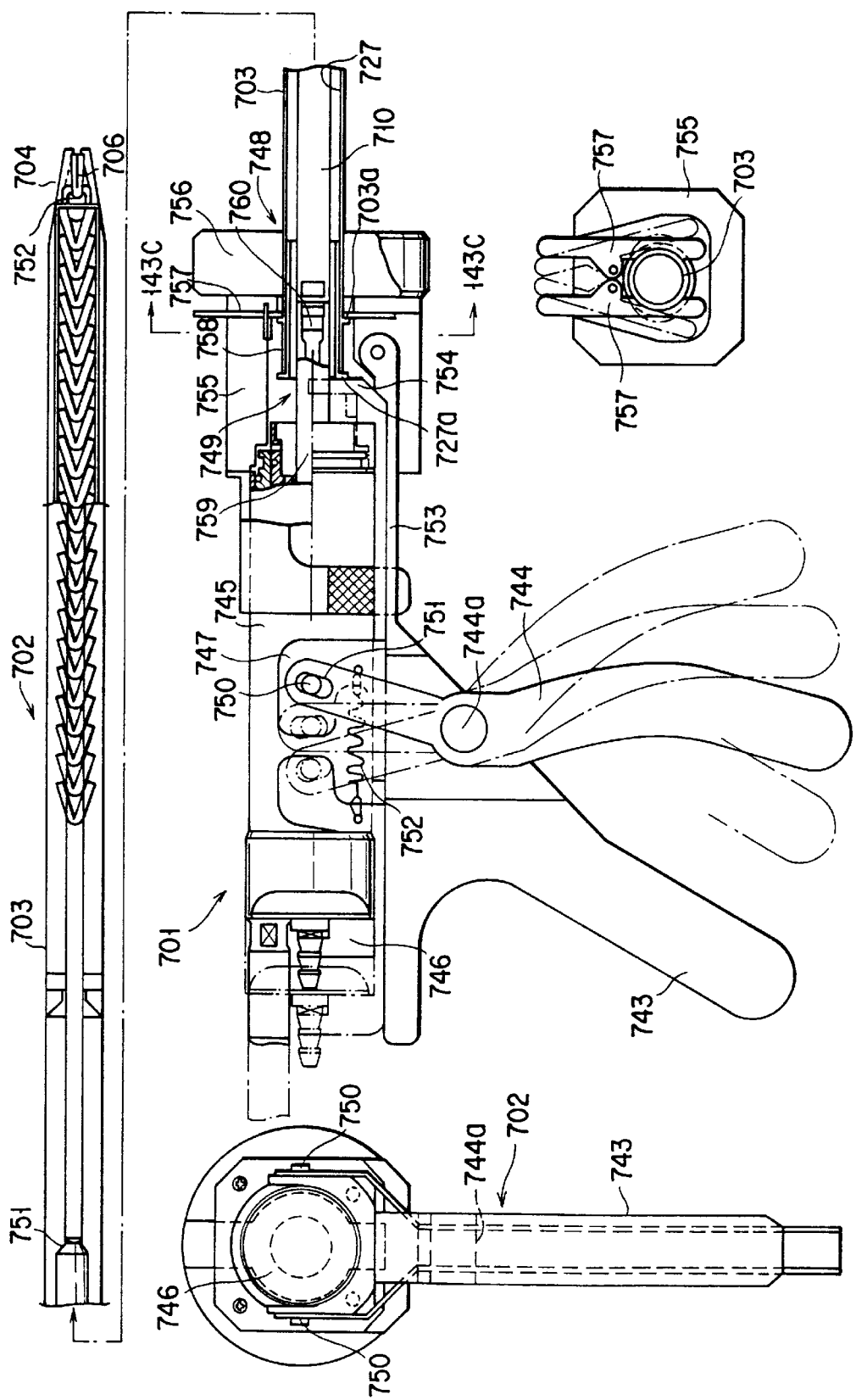
Figure 144A:
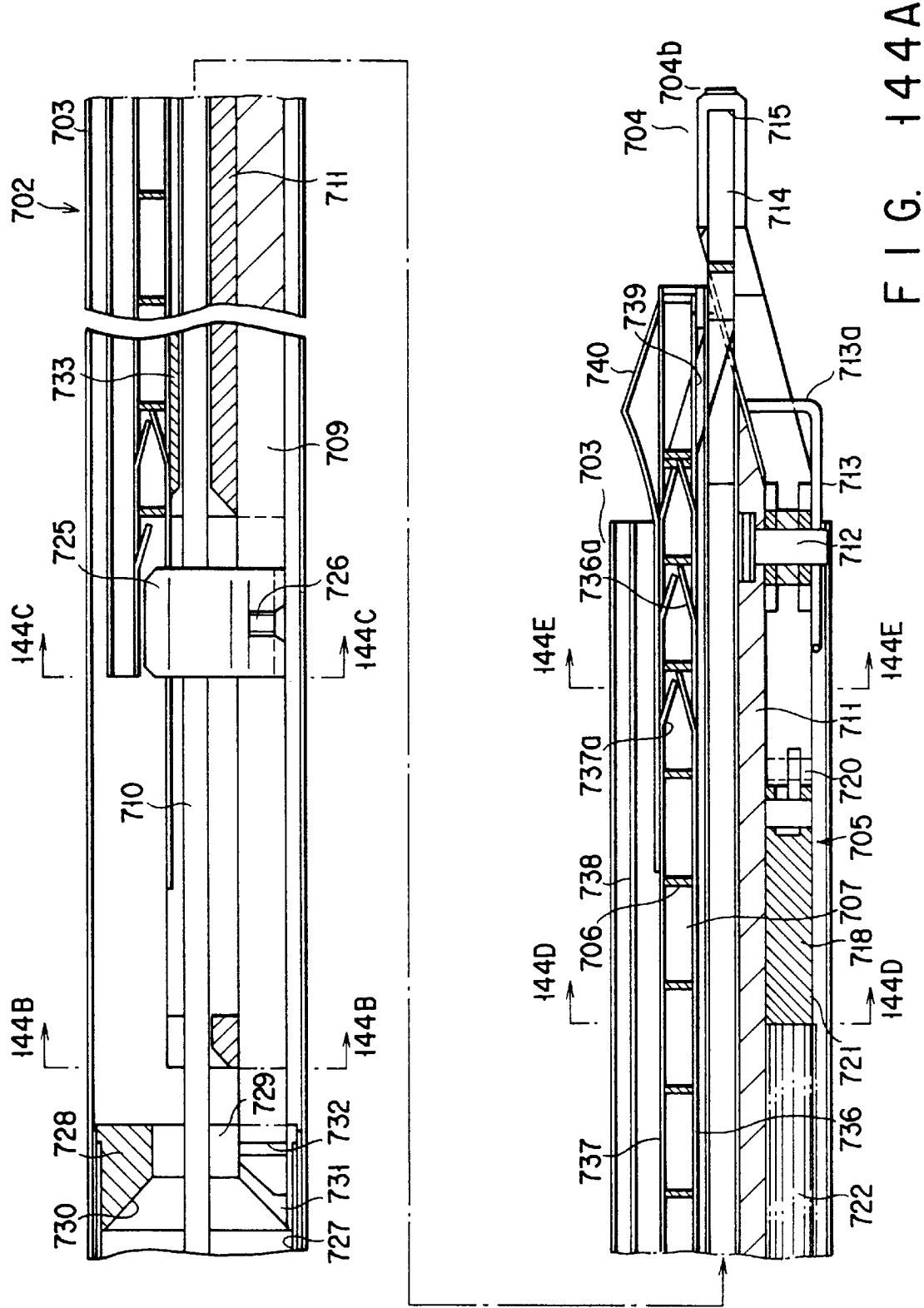
Figure 144B:
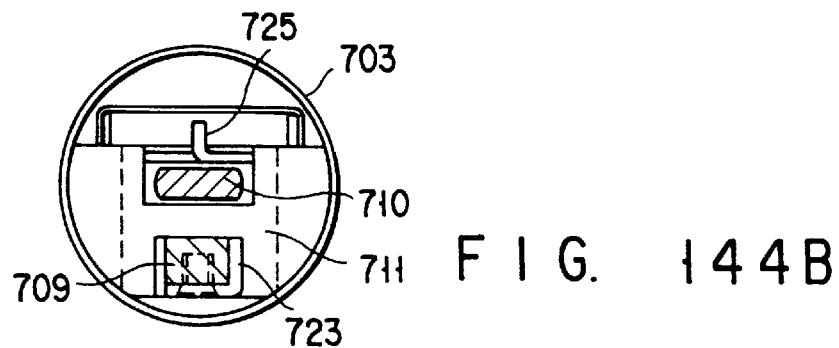
Figure 144C:
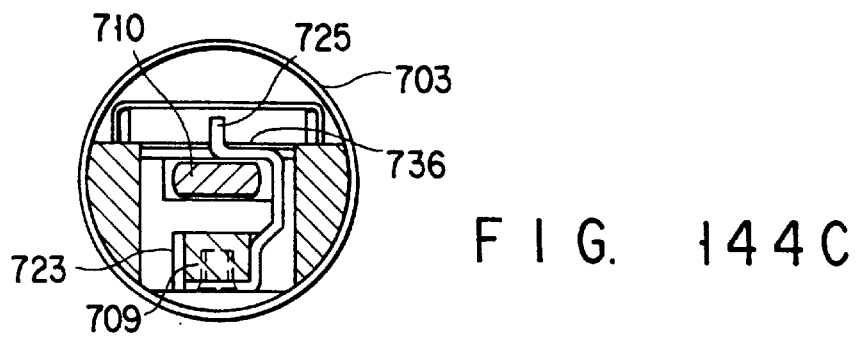
Figure 144D:
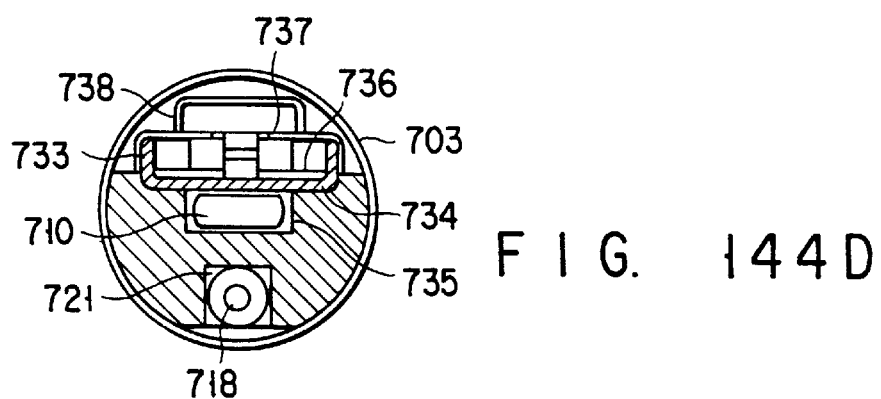
Figure 144E:
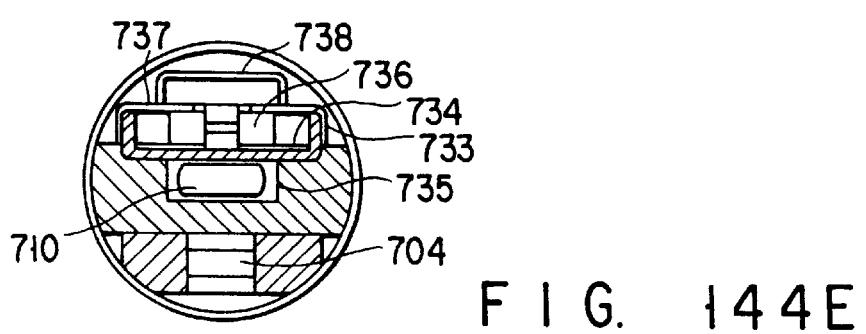
Figures 147A, 147B:
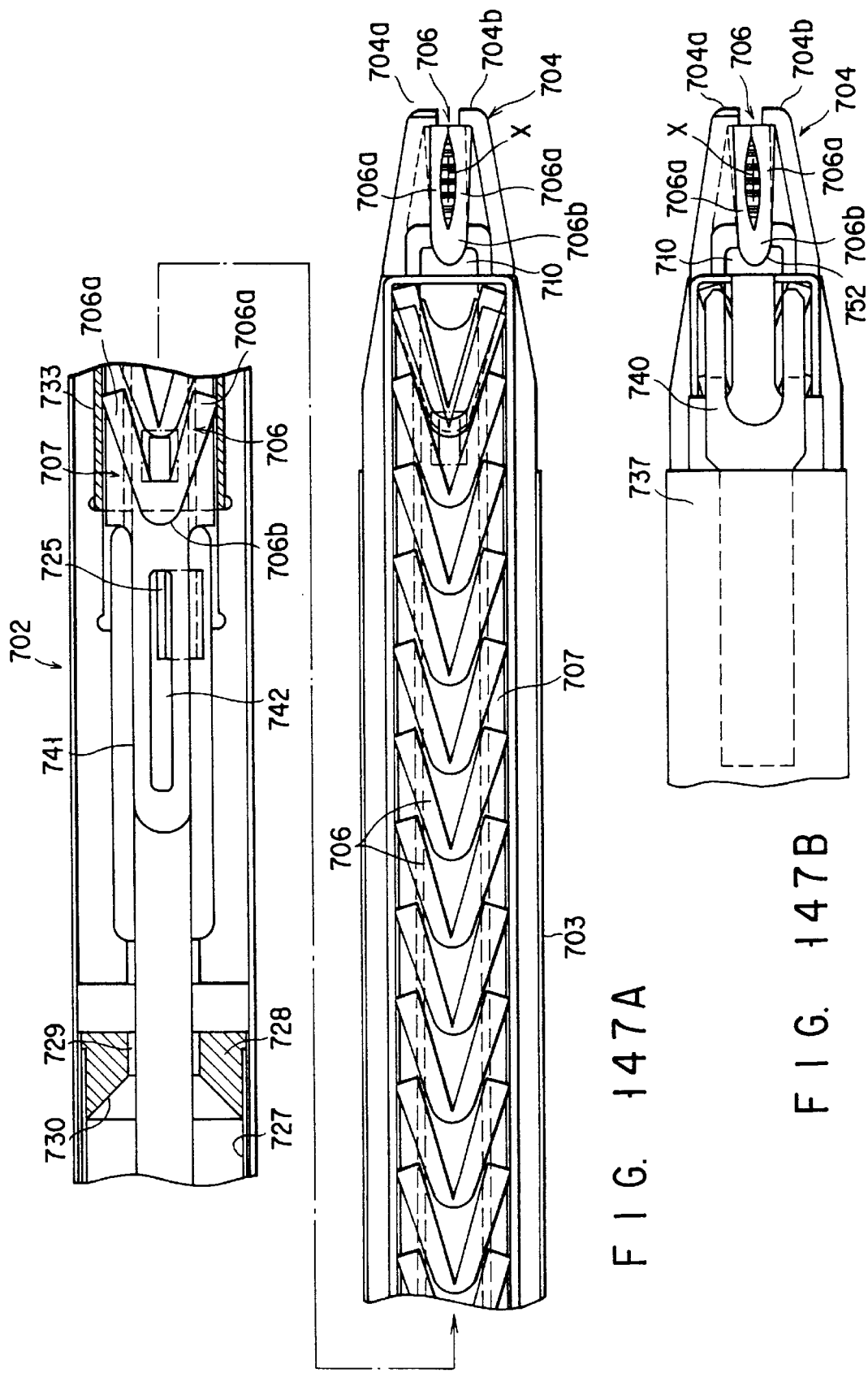

FIG. 121 is a perspective view showing an inner structure of the distal end portion of the applicator according to the forty-fifth embodiment; and FIG. 122 is a cross-sectional view showing the distal end portion of the applicator according to the forty-fifth embodiment;

FIG. 123A is a front view showing a tissue-fixing medical device according to a forty-sixth embodiment;

FIG. 123B is a side view showing the tissue-fixing medical device shown in FIG. 123A;

FIG. 124A is an enlarged front view showing the leading end of the tissue-fixing medical device shown in FIG. 123A;

FIG. 124B is a side view showing the tissue-fixing medical device shown in FIG. 124A;

FIG. 125 is a vertical side sectional view showing the leading end of an applicator of the tissue-fixing medical device shown in FIG. 123A;

FIG. 126 is a diagram showing a first stage for fixing tissues by the tissue-fixing medical device shown in FIG. 123A;

FIG. 127 is diagram showing a second stage for fixing tissues by the tissue-fixing medical device shown in FIG. 123A;

FIG. 128 is a diagram showing a third stage for fixing tissues by the tissue-fixing medical device shown in FIG. 123A;

FIG. 129 is a diagram showing tissues fixed by the tissue-fixing medical device shown in FIG. 123A;

FIG. 130A is a side view showing a modification of the tissue-fixing medical device according to the forty-sixth embodiment;

FIG. 130B is a vertical side sectional view showing the leading end of an applicator of the tissue-fixing medical device shown in FIG. 130A;

FIG. 131 is a side view having a partial cross sectional view of the leading end of a tissue-fixing medical device according to a forty-seventh embodiment;

FIG. 132 is a die view having a partial sectional view of the leading end of a tissue-fixing medical device according to a forty-eighth embodiment;

FIG. 133 is a side view showing a state of the operation of the tissue-fixing medical device shown in FIG. 132;

FIG. 134 is a side view showing the leading end of a tissue-fixing medical device according to a modification of the forty-eighth embodiment;

FIG. 135 is a side view showing a state of the operation of the tissue-fixing medical device shown in FIG. 134;

FIG. 136 is a vertical side sectional view of an operation section of a tissue-fixing medical device according to a forty-ninth embodiment;

FIG. 137 is a vertical side sectional view showing a first stage of the operation of the tissue-fixing medical device shown in FIG. 136;

FIG. 138A is a vertical side sectional view showing the tissue-fixing medical device in the state shown in FIG. 136;

FIG. 138B is an enlarged sectional view showing the leading end of the tissue-fixing medical device in the state shown in FIG. 138A;

FIG. 139 is a vertical side sectional view of an operation section of a tissue-fixing medical device according to a fiftieth embodiment;

FIG. 140 is an exploded view of the tissue-fixing medical device shown in FIG. 139;

FIG. 141A is a front view showing a first operating state of a tissue-fixing medical device according to a fifty-first embodiment;

FIG. 141B is a front view showing a second operating state of the tissue-fixing medical device according to the fifty-first embodiment;

FIG. 141C is a front view showing a third operating state of the tissue-fixing medical device according to the fifty-first embodiment;

FIG. 141D is a front view showing a fourth operating state of the tissue-fixing medical device according to the fifty-first embodiment;

FIG. 142A is a vertical side sectional view of an operation section of a tissue-fixing medical device according to fifty-second and fifty-third embodiments;

FIG. 142B is side view showing the leading end of the tissue-fixing medical device according to the fifty-second and fifth-third embodiments;

FIG. 143A is a side view having a partial cut portion and showing a surgical fixing instrument according to a fifty-fourth embodiment;

FIG. 143B is a rear view of an operation section of the surgical fixing instrument shown in FIG. 143A;

FIG. 143C is a sectional view taken along line 143C—143C shown in FIG. 143A;

FIG. 144A is a vertical side sectional view of an expansion section of the surgical fixing instrument shown in FIG. 143A;

FIG. 144B is a sectional view taken along line 144B—144B shown in FIG. 143A;

FIG. 144C is a sectional view taken along line 144C—144C shown in FIG. 143A;

FIG. 144D is a sectional view taken along line 144D—144D shown in FIG. 143A;

FIG. 144E is a sectional view taken along line 144E—144E shown in FIG. 143A;

FIG. 145 is a vertical plan view showing an initial stage of the operation of an elongation section of the surgical fixing instrument shown in FIG. 143A;

FIG. 146 is a vertical side sectional view showing an initial stage of the operation of an elongation section of the surgical fixing instructing shown in FIG. 143A;

FIG. 147A is a side view showing a state of a clip cartridge of the surgical fixing instrument shown in FIG. 143A from which a fixed plate has been removed; and FIG. 147B is a side view showing the clip cartridge of the surgical fixing instrument shown in FIG. 143A from which the fixed plate has been mounted.

DETAILED DESCRIPTION OF THE PREFERRED EMBODIMENTS

A clip applicator, which is a first embodiment of the present invention, will be described with reference to FIGS. 1 to 6. Of these figures, FIG. 2 shows a clip 1A which the applicator 10 will apply to ligate a tubular organ such as a blood vessel.

Figure 2:
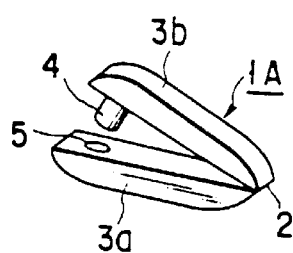
FIG. 2 is a perspective view showing a clip which is to applied by the application shown in FIG. 1.

As shown in FIG. 2, the clip 1A has a first leg 3a (first support means) and a second leg 3b (second support means). The legs 3a and 3b are hinged to each other at a hinge portion 2. The first leg 3a has a through hole 5. A pin 4 protrudes from the second leg 3b, extending toward the hole 5 of the first leg 3a. The legs 3a and 3b can abut each other, whereby the pin 4 is fixed, relatively tight in the hole 5 of the second leg 3a. The legs 3a and 3b are formed integral with each other, made of thermoplastic resin which is compatible with body tissues and which can be absorbed thereinto.

Figure 1:
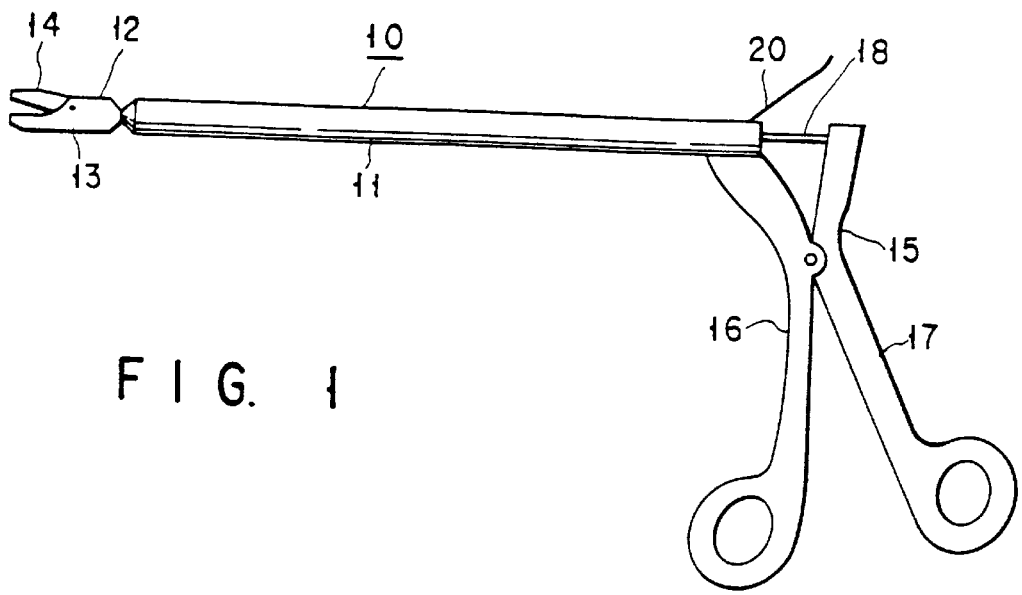
FIG. 1 is a side view showing a clip applicator which is a first embodiment of the present invention.
Figure 3:
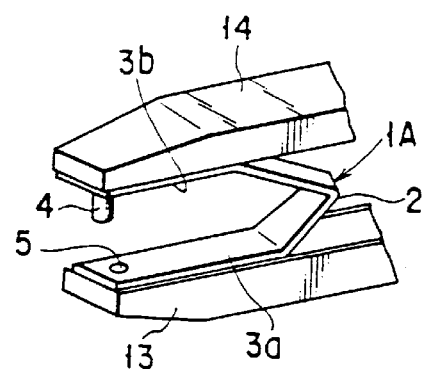
FIG. 3 is a perspective view showing the clip holder of the applicator shown in FIG. 1.

As shown in FIG. 1, the clip applicator 10 has a sheath 11 which will be inserted an abdominal cavity through a guide tube (not shown) such as a trocar. A clip holder 12 is attached to the distal end of the sheath 11, for holding the clip 1A. As FIG. 3 shows, the clip holder 12 comprises a first clip-holding member 13 secured to the sheath 11 and a second clip-holding member 14 connected by a pin to the first clip-holding member 13. The second clip-holding member 14 can rotate about the pin, whereby the clip holder 12 is opened and closed.

Referring back to FIG. 1, an operation section 15 is connected to the proximal end of the sheath 11. The section 15 is manipulated to open and close the clip holder 12 attached to the distal end of the sheath 11. The operation section 15 comprises a fixed handle 16 and a handle 17. The fixed handle 16 is fastened to the proximal end of the sheath 11. The handle 17 is coupled to the fixed handle 16 by a connecting pin, and can rotate around the connecting pin. A wire 18 made of comparatively hard material is connected at one end to the handle 17, extends through the sheath 11, and is connected at the other end to the proximal end of the second clip-holding member 14. Therefore, the handle 17 pulls the wire 18, closing the clip holder 12, when it is rotated in one direction, and pushes the wire 18, opening the clip holder 12, when it is rotated in the opposite direction.

Figure 4:
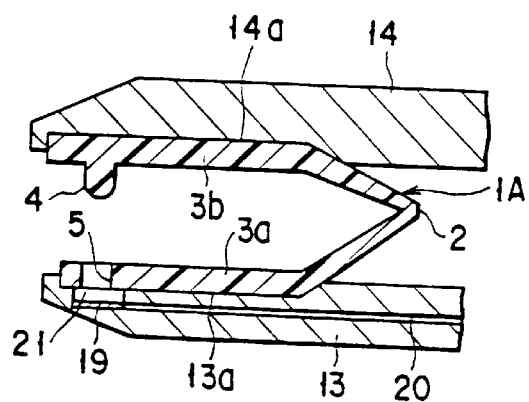
FIG. 4 is a sectional view showing a part of the clip holder of the applicator shown in FIG. 1.

As can be understood from FIGS. 3 and 4, the clip 1A is held between the clip-holding members 13 and 14 of the holder 12, so that it may be inserted into an abdominal cavity and applied therein. To be more specific, the legs 3a and 3b of the clip 1A are fitted, in part, in the recesses 13a and 14a formed in the opposing surfaces of the clip-holding members 13 and 14, respectively. Hence, the holder 12 holds clip 1A steadfastly.

As shown in FIG. 4, an electric heater 19 such as a diode or a ceramic heater 19 is embedded in that surface of the first clip-holding member 13 which opposes the second clip-holing member 14. The heater 19 is connected to one end of a power-supply cord 20, which is embedded in the first clip-holding member 13 and extends through the sheath 11 to the proximal end of the applicator 10. The cord 20 is connected, at its other end, to a power supply (not shown) located outside the applicator 10. The heater 19 is exposed through an escape hole 21 made in said surface of the first clip-holding member 13.

Figures 5A, 5B, 5C:
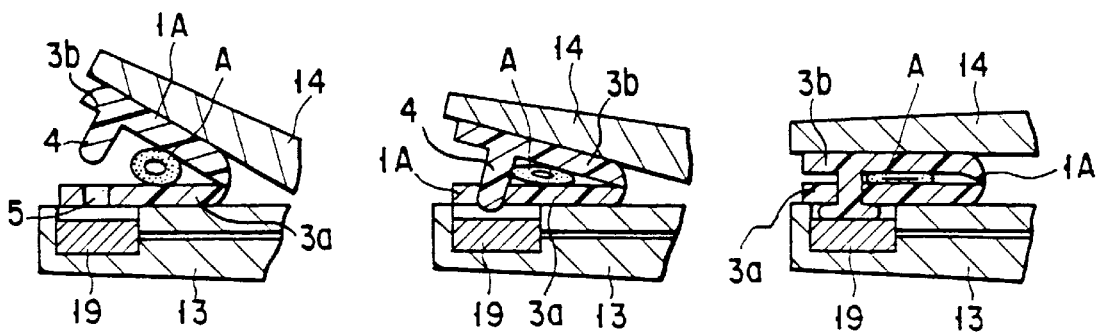
FIGS. 5A, 5B, and 5C are diagrams explaining how to operate the clip applicator of FIG. 1.

With reference to FIGS. 5A, 5B, and 5C, it will be described how the clip applicator 10 is operated to apply the clip 1A to ligate a tubular organ such as a blood vessel. The clip 1A is removed from a cartridge (not shown). As shown in FIG. 5A, the clip 1A is pinched in the gap between the clip-holding members 13 and 14 of the clip holder 12 which is attached to the distal end of the sheath 11.

Next, the sheath 11 is inserted into a body cavity where the tubular organ A is located. The clip applicator 10 is manipulated, thereby placing the tubular organ A in the gap between the legs 3a and 3b of the clip 1A as is illustrated in FIG. 5A. Then, the handle 17 is operated, rotating the second clip-holding member 14 of the clip holder 12 and thus closing the clip 1A. As a result, the pin 4 of the second leg 3b of the clip 1A fits into the through hole 5 of the first leg 3a, as is shown in FIG. 5B. The tubular organ A is thereby collapsed.

In this condition, an electric current is supplied from the power supply (not shown) to the heater 19 embedded in the first clip-holding member 13, by either automatic operation or manual operation. The heater 19 heats the tip of the pin 4 fitted in the hole 5. The tip of the pin 4 is thereby fused to the first leg 3a.

Once the pin 4 of the second leg 3b is fused to the first leg 3a, the clip 1A firmly clamps the tubular organ A. This prevents the clip 1A from becoming so loose as to release the tubular organ A.

Another clip applicator, which is a second embodiment of the invention, will be described with reference to FIGS. 6 and 7.

Figure 6:
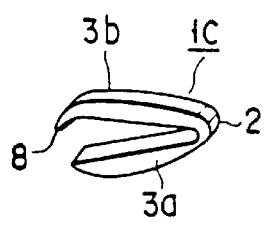
FIG. 6 is a perspective view showing a clip to be applied by a clip applicator according to a second embodiment of the invention.
Figure 7:
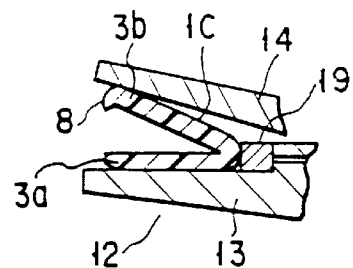
FIG. 7 is a sectional view showing a part of the clip holder of the applicator which is the second embodiment of this invention.

FIG. 6 shows a clip 1C used in this embodiment, and FIG. 7 shows the distal end portion of the clip holder 12 of the clip applicator. As can be understood from FIG. 6, the second leg 3b of the clip 1C has a claw 8 at its distal end. The claw 8 is so shaped as to latch the distal end of the first leg 3a of the clip 1C. As shown in FIG. 7, a heater 19 is located at the hinge portion of the clip 1C. After the clip 1C is closed, with the claw 8 latching the distal end of the first leg 3a, the heater 19 heats and softens the hinge portion. Then, the hinge portion is cooled, whereby the clip 1C is deformed permanently, with the legs 3a and 3b fastened together firmly.

Figure 8A:
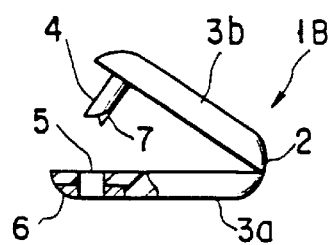
FIGS. 8A and 8B are side views showing a modification of the clip shown in FIG. 6.
Figure 8B:
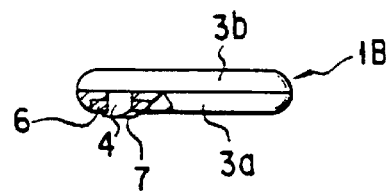

FIGS. 8A and 8B show a modification 1B of the clip 1A shown in FIG. 2. The clip 1B differs from the clip 1A in two respects. First, that portion of the lower surface of the leg 3a which surround the hole 5 is made of heat-resistant resin 6. Second, the pin 4 has a flaring forked tip 7.

Even when the heat generated by the heater 19 is applied to the clip 13, the leg 3a of the clip 1B is not fused. When the clip 1B is closed by operating the applicator 10, the two parts of the forked tip 7 are moved away from each other and, in this condition, and thermally deformed due to the heat generated by the heater 19. Once the forked tip 7 is so deformed, the pin 4 is prevented from slipping out of the hole 5, whereby legs 3a and 3b of the clip 1B are connected together firmly.

Figure 9:
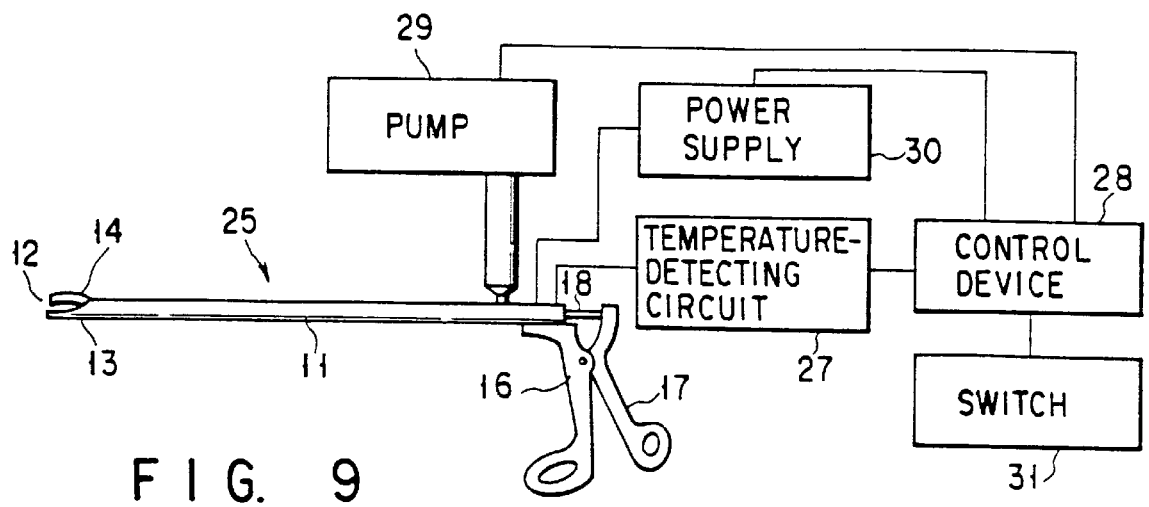
FIG. 9 is a diagram showing a clip applicator according to a third embodiment of this invention.

A clip applicator 25 according to a third embodiment of the invention will be described, with reference to FIGS. 9 and 10.

Figure 10:
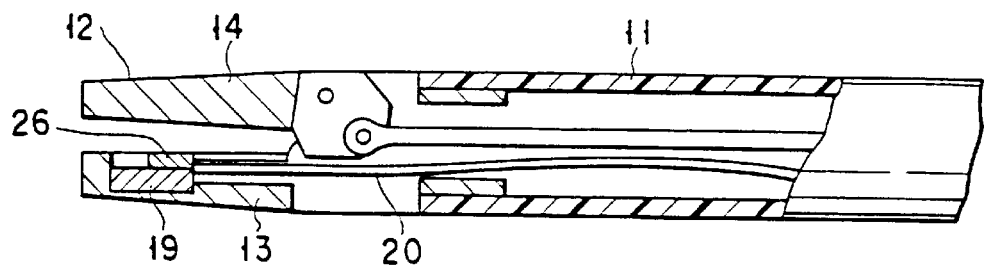
FIG. 10 is a sectional view showing the distal end portion of the clip applicator shown in FIG. 9.

As is evident from FIG. 10, a temperature sensor 26 is arranged near the heater 19 embedded in the first clip-holding member 13 of the clip holder 12. The sensor 26 is connected to a temperature-detecting circuit 27 shown in FIG. 9. The temperature data the circuit 27 has obtained is input to a control device 28. The device 28 controls a cooling-water pump 29 and a power supply 30 in accordance with the temperature data. The control device 28 is turned on or off by operating a switch 31. The pump 29 is connected to the proximal end portion of the sheath 11 of the applicator 25. The cooling water can thereby be supplied from the pump 29 to the clip holder 12 through the sheath 11. The clip applicator 25 is identical in any other structural features to the clip applicator 10 which is shown in FIG. 1.

The handle 17 is manipulated, thus closing the clip holder 12, hence, closing the clip 1A (not shown) held between the clip-holding members 13 and 14. As a result, the clip 1A clamps a tubular organ (not shown). Then, the switch 31 is closed, and the control device 28 supplies a signal to the power supply 30. In response to the signal the power supply 30 supplies a current the heater 19. The heater 19 generates heat. The heat is applied to the pin 4 which is inserted in the hole 5 of the leg 3a.

The temperature sensor 26 detects the temperature of the heater 19 and generates a signal representing this temperature. The signal is supplied to the temperature-detecting circuit 27, which produces temperature data from the signal. The data is input to the control device 28. When the temperature represented by the data exceeds a preset value, the circuit 28 outputs a temperature control signal, which turns off the power supply 30. The heater 19 can therefore be maintained at a temperature which is higher than the glass-transition point of the pin 4 and which is appropriate for thermally deforming the pin 4.

Upon lapse of a prescribed time after the temperature of the heater 19 has reached the predetermined value, said prescribed time being long enough for the pin 4 to fuse with first leg 3a, it is detected that the clip 1A has been thermally deformed. At this time, the control device 28 generates a power-supply stop signal and a pump drive signal. The power-supply stop signal and the pump drive signal are supplied to the power supply 30 and the cooling-water pump 29, respectively. In response to the stop signal, the power supply 30 stops supplying power to the heater 19. In response to the drive signal, the cooling-water pump 29 operates, supplying cooling water (e.g., physiological salt solution) to the clip holder 12 through the sheath 11. The water, thus supplied, cools the holder 12 holding the clip 1A.

Since the cooling water is supplied to the clip holder 12 and cools the clip 1A immediately after the pin 4 of the clip 1A is fused to the first leg 3a of the clip 1A, the thermally deformed portion of the clip 1A can be rendered rigid quickly. The clip 1A can therefore ligate the body tissue readily, within a short period of time.

A stapler 40, which is a fourth embodiment of the present invention and designed to suture body tissues, will be described with reference to FIGS. 11 to 15.

Figure 11:
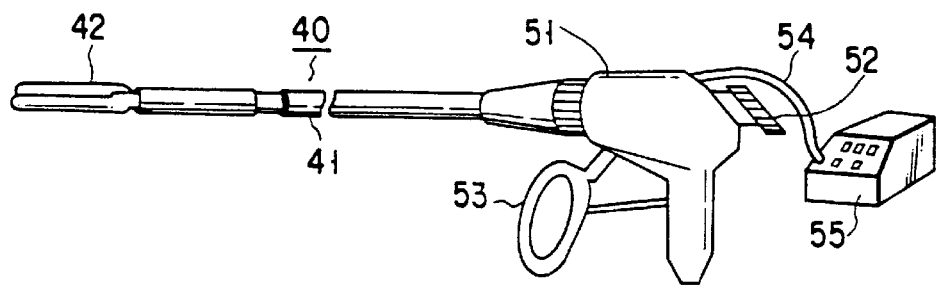
FIG. 11 is a side view showing a stapler which is a fourth embodiment of the present invention.

As FIG. 11 shows, the stapler 40 has an insertion section 41, a clamp section 42, and an operation section 51. The insertion section 41 is a sheath which is to be inserted into an abdominal cavity through a guiding instrument such as a trocar (not shown). The clamp section 42 designed for clamping body tissues is secured to the distal end of the insertion section 41.

Figure 12:
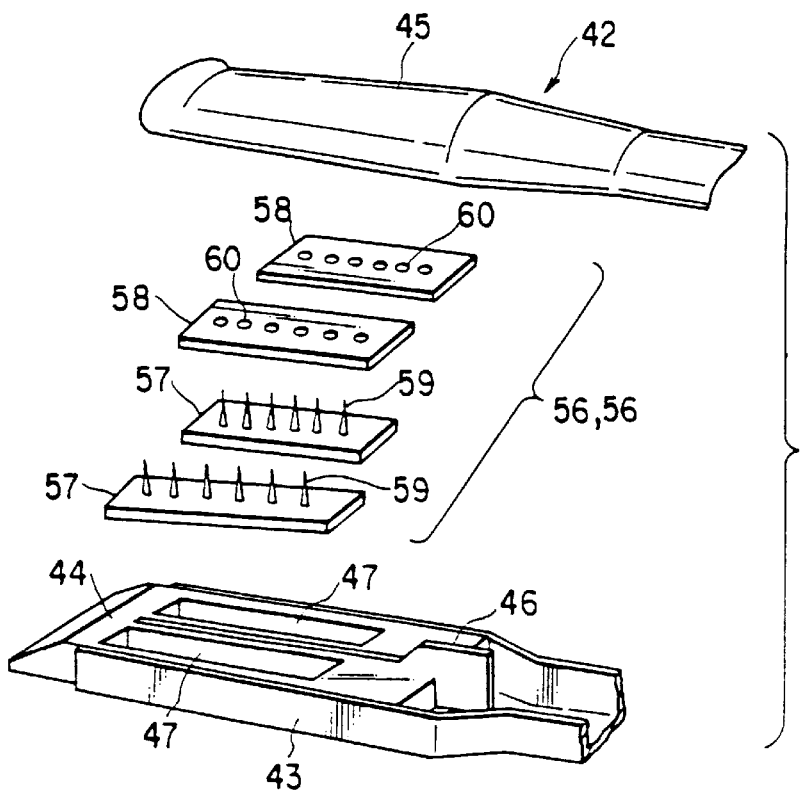
FIG. 12 is an exploded view showing the clamp section of the stapler illustrated in FIG. 11.
Figure 14:
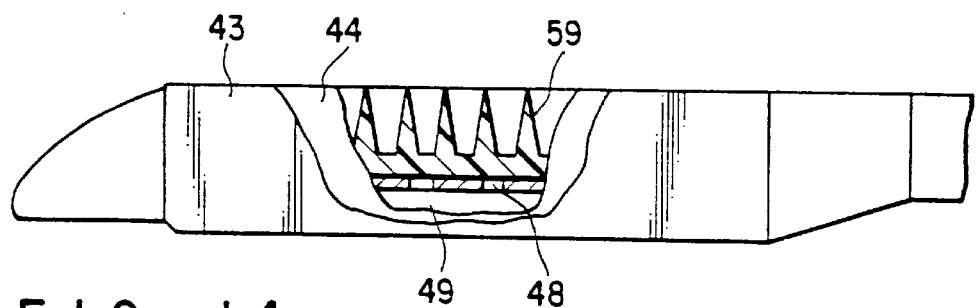
FIG. 14 is a partially sectional side view showing the cartridge of the clamp section.

As shown in FIG. 12, the section 42 comprises a casing 43, a cartridge 44, and an anvil 45. The casing 43 is secured to the distal end of the insertion section 41 and has an opening top. The cartridge 44 is removably contained in the casing 43. The anvil 45 opposes the upper surface of the cartridge 44 and can rotate to open and close the casing 43. The cartridge 44 has a knife-guiding groove 46 made in the upper surface, extending along the longitudinal axis of the casing 43. Two rectangular recesses 47 are made in the upper surface of the cartridge 44, located symmetrically with respect to the knife-guiding groove 46, for receiving staple bases 57 of a stapler 56 which will be described later. A knife (not shown) is moved forward, along the the knife-guiding groove 46. As is shown in FIG. 14, a plurality of gas nozzles 48 is formed in the bottom of each recess 47, for applying gas onto the staple base 57, thereby to push the base 57 upwards. As shown in FIG. 14, the cartridge 44 has a pusher-gas passage 49 through which to supply the gas for pushing the bases 57 upwards.

Figure 13:
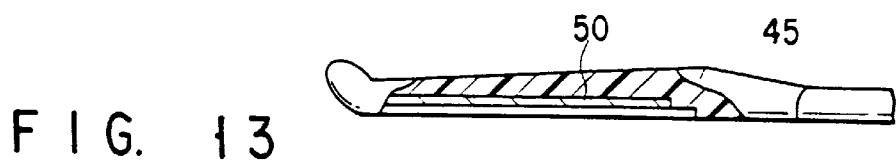
FIG. 13 is a partially sectional view showing the anvil of the clamp section shown in FIG. 12.

As shown in FIG. 13, a heater 50 is embedded in the lower surface of the anvil 45, which function as a stapler-holding surface. The heater 50 is used to thermally deform the tips of the staple pins 59 which stand upright on the staple bases 57 set in the recesses 47.

Referring back to FIG. 11, the operation section 51 is connected to the proximal end of the insertion section 41. The operation section 51 comprises an anvil-rotating handle 52 and a firing handle 53. The handle 52 is manipulated to rotate the anvil 45, thereby to open and close the clamp section 42. The firing handle 53 is squeezed to let the pusher gas flow from a gas cylinder (not shown) incorporated in the section 51 into the pusher-gas passage 49 of the cartridge 44. A power-supply cord 54, which is connected at one end to the heater 50, extends from the operating section 51 and is connected to a power supply 55.

As FIG. 12 shows, each staple 56 comprises a staple base (first support means) 57 and a plate-shaped staple cover (second support means) 58. A plurality of staple pins 59 stand upright on the staple base 57. The staple cover 58 has a plurality of holes 60 for receiving the staple pins 59. All components of each stable 56 are made of resin which is absorbable into body tissues.

It will be described how to apply the staples 56 by the stapler to stitch body tissues together. First, the cartridge 44 containing the bases of the staples 56 is placed in the casing 43 of the clamp section 42, and the staple covers 58 are fitted in the anvil 45. Then, the clamp section 42 containing the staples 56 is attached to the distal end of the insertion section 41 of the stapler 40. The insertion section 41 is guided into a body cavity, thus locating the clamp section 42 at a desired position within the body cavity. The anvil-rotating handle 52 is manipulated, thereby opening the anvil 45. The clamp section 42 is moved until the body tissues B are clamped placed between the cartridge 44 and the anvil 45.

In this condition, the firing handle 53 is squeezed, making the pusher gas flow from the gas cylinder (not shown) into the recesses 47 made in the upper surface of the cartridge 44 through the pusher-gas passage 49 cut in the the cartridge 44. The gas pushes up the staple bases 57 placed in the recesses 47. As the staple bases 57 are thus pushed upwards, the staple pins 59 standing upright on the bases 57 pierce the tissues B and fit into the holes 60 of the staple covers 58.

Figure 15A:
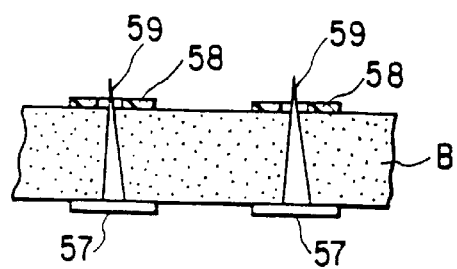
FIGS. 15A and 15B are diagrams explaining the operation of the stapler shown in FIG. 11.
Figure 15B:
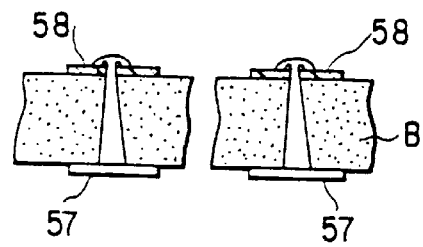

Then, a current is supplied from the power supply 55 to the heater 50. The heater 50 heats the tips of the staple pins 59 protruding from the holes 60 of the staple covers 58. The tips of the pins 59 fuse with the upper surface of the staple cover 58 as is shown in FIG. 15B which illustrates the body tissues B already cut with the knife (not shown) incorporated in the stapler 40.

As described above, the heater 50 embedded in the anvil 45 can fuse the tips of the staple pins 59, fastening the pins 59 to the upper surface of the staple covers 58. The staple bases 57 can thereby coupled to the staple covers 58 steadfastly. As a result, the body tissues B can be reliably fixed or clamped between each staple base 57 and the staple cover 58 associated therewith. Since the staple bases 57 and the staple covers 58 are made of resin which can be absorbed into tissues, they will be absorbed into the tissues B after the suture of the body tissues B.

Another stapler 70, which is a fifth embodiment of this invention, will be described with reference to FIGS. 16, 17, and 18.

The stapler 70 is designed to apply a staple 65 of the type shown in FIG. 18. The staple 65 comprises two net-like strips (support means) 66 and 67 and a plurality of staple pins (fastening means) 68. The strips 66 and 67 are made of heat-resistant material which can be absorbed into body tissues. The staple pins 68 are made of resin which is absorbable into body tissues. Each pin 68 has a proximal end 68a having a larger diameter than the remaining portion.

Figure 16:
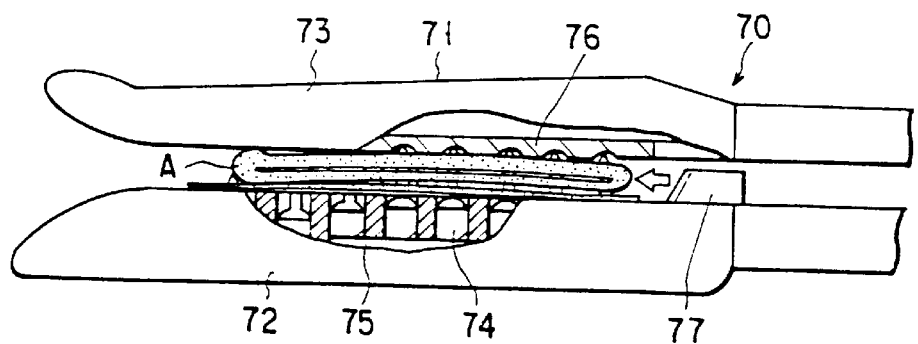
FIG. 16 is a partially sectional side view showing the distal end portion of a stapler which is a fifth embodiment of the present invention.

FIG. 16 is a partially sectional side view of the distal end portion of the stapler 70. As this figure shows, a clamp section 71 is connected to the distal end of the sheath of the stapler 70. The clamp section 71 is designed to clamp a tubular organ A such as a blood vessel. The section 71 comprises a cartridge 72 and an anvil 73. The cartridge 72, which is removable, contains the staple pins 68 and has pushers 74 and a pusher handle 75 for pushing the pushers 74 upwards, one after another. The anvil 73 is connected to the sheath and opposes the staple-holding surface (i.e., the upper surface) of the cartridge 72.

A heater 76 is arranged in the staple-holding surface (i.e., the lower surface) of the anvil 73, for heating and fusing the tips of the staple pins 68. As shown in FIG. 17, the net-like strips 66 and 67 are mounted on the staple-holding surface of the cartridge 72 and that of the anvil 73, respectively. The staple pins 68 are arranged in rows extending parallel to the axis of the cartridge 72. The pusher bar 75 extend also parallel to the axis of the cartridge 72 and can be moved back and forth. A knife 77 is mounted on the staple-holding surface of the cartridge 72. The knife 77 can be moved back and forth along the axis of the cartridge 72. When moved forward, it can cut a tubular organ A clamped between the cartridge 72 and the anvil 73.

To suture the tubular organ A with the staple 65 by means of the stapler 70, thus structured, the distal end portion of the stapler 70 is guided into a body cavity containing the tubular organ A. The clamp section 71 is then manipulated, thereby clamping the organ A between the cartridge 72 and the anvil 73. Next, the pusher bar 75 is slit forward by remote control, pushing the pushers 74 upwards one after another. The staple pins 73 are thereby pushed up, piercing the net-like strips 66, the organ A, and the net-like strip 67 and abutting the staple-holding surface of the anvil 73, as is shown in FIG. 17. In this condition, the heater 76 is turned on, heating and fusing the tips of the staple pins 68. As a result, the tips of the pins 68 collapse between the anvil 73 and the net-like strip 67 as shown in FIG. 18B. At the same time the tips of the pins 68 are so fused, the knife 77 is moved forward, thus cutting the tubular organ A along the row of of staple pins 68.

In this way, the stapler 70 can suture the tubular organ A with the staple 65, as steadfastly as does the stapler 40 shown in FIGS. 11 to 14.

Still another stapler, which is a sixth embodiment of the present invention, will be described with reference to FIG. 19.

Figure 17:
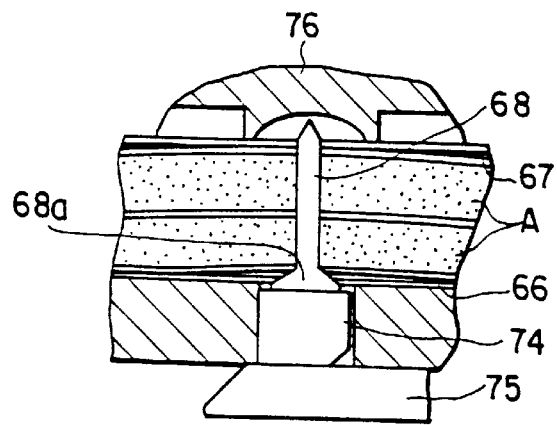
FIG. 17 is a cross-sectional view showing part of the clamp section of the stapler shown in FIG. 16, and explaining how to suture a tubular organ by means of the stapler.

Referring to FIG. 19, the clamp section of this stapler comprises a cartridge 72, an anvil 73, a pusher 74, a pusher bar 75, and a knife 77, which are identical to those of the stapler shown in FIG. 17. The clamp section has a heater 78 which can slide back and forth in the passage formed within the anvil 73, along the axis of the anvil 73. The heater 78 is used to heat the tips of U-shaped staples 80 made of resin which is absorbable into body tissues. A staple-receiving plate 79 is mounted on the lower surface of the anvil 73. The plate 79 is made of heat-resistant material and has a plurality of through holes 81 for receiving the tips of the staples 80.

This stapler is manipulated in the same way as the stapler. The sliding heater 78 located in the anvil 73 can locally heat the tips of each staple 80 partly inserted in the through holes 81 of the staple-receiving plate 79. As a result, the tips of the staples 80 are fused onto the upper surface of the plate 79, whereby the stapler can suture the tubular organ A with the staple 80, as steadfastly as does the stapler 70 (FIG. 16) which is the fifth embodiment of the invention.

A circular stapler 90, which is a seventh embodiment of this invention, will be described with reference to FIGS. 20, 21, and 22.

FIG. 22 is an exploded view showing a staple 85 which this stapler 90 apply to stitch tubular organs together. The staple 85 comprises a ring-shaped base 86, a plurality of pins 87, and a ring-shaped cover 89. The base 86 consists of four arcuate segments. The pins 87 protrude from the base 86 in parallel to one another and spaced apart in the circumferential direction of the base 86. The cover 89 also consists of four arcuate segments, each having the same number of pin-receiving holes 88. All components of the staple 85 are made of thermoplastic resin which can be absorbed into body tissues or which is compatible with body tissues.

As is shown in FIG. 20, the circular stapler 90 comprises an insertion section 91 which is to be inserted into a tubular organ A, a suture section 92 connected to the distal end of the insertion section 91, and an operation section 93 connected to the proximal end of the insertion section 91. The suture section 92 comprises a staple-feeding section 94 and a staple-receiving section 96, as is illustrated in FIG. 21. The staple-feeding section 94 is fastened to the insertion section 91. The staple-receiving section 96 is coupled to the distal end of the section 94 by a connecting bolt 95.

The staple-feeding section 94 contains a staple pusher 97 for pushing the staple base 86 forward, and a cylindrical cutter 98 for cutting off any unnecessary portions of the tubular organ A after the two severed parts of the organ A are stitched together. Both the staple pusher 97 and the circular cutter 98 can be driven back and forth by means of a hydraulic cylinder (not shown). As shown in FIG. 20, a handle 99 is connected to the operation section 93, for operating the hydraulic cylinder.

Referring to FIG. 21, the staple-receiving section 96 has a staple-holding surface 100 for holding the pins 87 which protrude from the base 86 pushed forward from the staple-feeding section 94. Formed in the surface 100 is a staple-holding groove 101 designed for holding the ring-shaped cover 89 of the staple 85. A heater 102 is placed at the bottom of the groove 101, for heating the tips of the staple pins 87.

The staple-feeding section 94 has a screw hole 103 which is cut in its the distal end and which is coaxial with the section 94. The connecting bolt 95 is set in screw engagement with the hole 103, coupling the staple-receiving section 96 to the distal end of the section 94. Arranged within the screw hole 103 is an electrically conductive spring 104, which extends through the connecting bolt 95 and is connected to the heater 102, for supplying electric power to the heater 102.

The stapler 90, thus constructed, is operated as follows, in order to stitch together two severed parts of the tubular organ A. As shown in FIG. 20, the insertion section 92 is inserted into the tubular organ A until the staple-feeding section 94 and the staple-receiving section 96 are placed within said two severed parts, respectively. In this condition, the severed edges of the organ parts, which have shrunk and collapsed, are located between the sections 94 and 96.

The handle 99 is squeezed, driving the staple is pusher 97 forward. The staple base 86 is thereby pushed forward, whereby the staple pins 87 pierce the severed edges of the organ parts, are then inserted into the pin-receiving holes 88 of the ring-shaped cover 89, and finally abut on the heater 102 arranged in the staple-receiving section 96. In this condition, an electric current is supplied to the heater 102, which heats the tips of the pins 87. The tips of the pins 87 are thereby fused onto the ring-shaped cover 89. As a result, the severed parts of the tubular organ A are fastened together. Thereafter, the cylindrical cutter 98 is thrust forward, cutting the unnecessary portions from the sutured parts.

The circular stapler 90 can, therefore, achieve the same advantages as the stapler (FIG. 19) which is the sixth embodiment of the present invention.

Another stapler 110, which is an eighth embodiment of the invention, will be described with reference to FIG. 23 and FIGS. 24A and 24B. As FIG. 23 shows, this stapler 110 comprises an insertion section 111 and an operation section 112. The operation section 112 is connected to the proximal end of the insertion section 111, and has a handle 113, a heater switch 114, and a water-supply switch 115. A power supply 116 and a water-supplying device 117 are connected to the operation section 112.

FIGS. 24A and 24B are cross-sectional views showing the internal structure of the distal end portion of the insertion section 111. The distal end portion of the section 111 contains a generally M-shaped staple 118. The staple 118 is made of thermoplastic resin which is absorbable into, or is compatible with, body tissues. The staple 118 has claws 119a and 119a, each at one end, which are sharp enough to piece body walls A and which can fasten body walls together.

The distal end portion of the insertion section 111 contains a staple pusher 121 which can be driven back and forth along the axis of the insertion section 111, for pushing the staple 118 from the insertion section 111 through a staple-feeding hole 120 made in the distal end of the insertion section 111. A heater 122 is attached to the distal end of the staple pusher 121. The heater 122 is connected to the power supply 116 by a cable 123 and has, in its front, a recess 122a. The recess 112a has the same shape as the staple 118, for holding the staple 118.

The insertion section 111 contains a tube 124, through which the water-supplying device 117 supplies cooling water to the distal end of the insertion section 111, thereby to cool the staple 118. An anvil 125 is located in the distal end of the section 111. The anvil 125 has a flange for supporting the center portion of the staple 118. The flange functions to hold the center portion of the staple 118.

The stapler 110, thus constructed, is operated as follows, in order to fasten the body walls A together. First, the insertion section 111 is so positioned that the the staple-feeding hole 120 is directed to the body walls A to be stitched together. Then, the handle 113 of the operation section 112 is squeezed, driving the staple pusher 121 to the distal end of the section 111. The pusher 121 subsequently pushes the center portion of the staple 118 against the anvil 125 as is shown in FIG. 24A. Pushed further, the staple 118 is bent or closed, whereby its claws 119a and 119b pierce the body walls A and finally abut on each other, piercing the walls A at other portions, as is illustrated in FIG. 24B.

Next, the heater switch 114 of the operation section 112 is pushed, supplying an electric current to the heater 122 through the cable 123. The heater 122 heats the staple 118, removing the bending strain from the staple 118. Thereafter, the water-supply switch 115 of the operation section 112 is pushed, whereby the water-supplying device 117 supplies cooling water to the distal end of the insertion section 111. The staple 118 is thereby cooled and hence deformed permanently. At this time, the staple 118 is held by the anvil 125. To release the staple 118 from the anvil 125, it suffices to move the staple 118 sideways to a position where the staple slips out of the anvil 125.

Since the stapler 110 heats and cools the staple 118, thus deforming the same permanently as described above, it fasten the walls A to each other, both readily and reliably. In addition, the use of the generally M-shaped staple 118 makes it possible to suture flat body tissues together.

FIGS. 25A, 25B, and 25C show a modification of the stapler 110 according to the eighth embodiment of the invention, and explain how this stapler applies a staple 118 to stitch body walls A together. The modification differs from the stapler 110 in that a staple holder 126 is removably attached to the front of the heater 122. Both the staple 118 and the staple holder 126 are made of resin which is absorbable into, or is compatible with, body tissues.

Figure 27A:
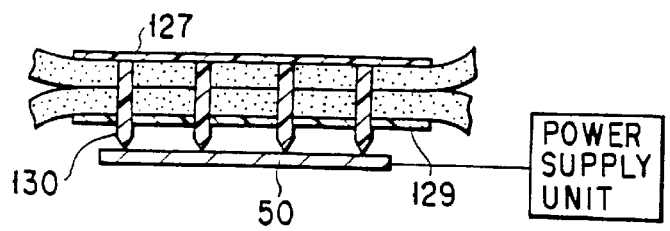
FIGS. 27A and 27B are sectional views of the staple shown in FIG. 26 and explaining how the staple fastens tow tissue layers together.
Figure 27B:
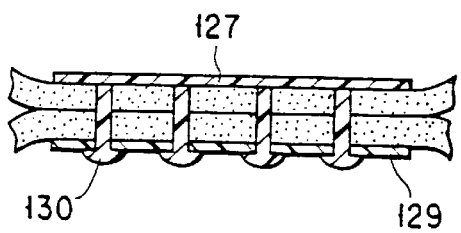

FIG. 26 and FIGS. 27A and 27B show a staple which can be applied by the stapler 40 shown in FIG. 12. As is shown in these figures, the staple comprises a base 127, a plurality of pins 128 protruding downwards from the lower surface of the base 127, and a pin-holding plate 129 having through holes 130. The holes 130 have a diameter larger than that of the pins 128. The components of the staple 127 are all made of materials which can be absorbed into body tissues. More precisely, the pins 128 are made of material having a softening point higher than the material of the pin-holding plate 129. As is shown in FIG. 27A, a heater 50 is used to heat and thermally deform the lower ends of the pins 128.

After inserted in the through holes 130 of the pin-holding plate 129, the pins 128 of the staple 127 are fused at their tips, whereby the tissue layers clamped, as if riveted, between the base 127 and the pin-holding plate 129. The tissue layers are thereby fastened to each other steadfastly. Since the plate 129 shields the heat emanating from the heater 50, thermal damages, if any, to the body tissues can be minimized. Further, since the staple pins 128 have no projections or stepped portions, they do not damage the body tissues so much.

Figure 28:
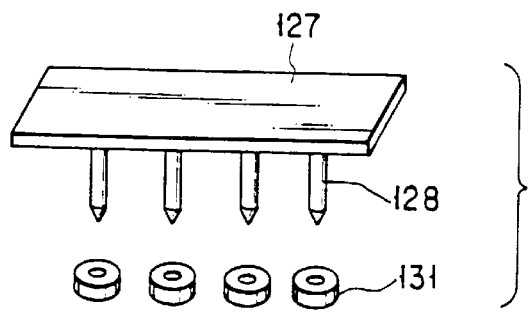
FIG. 28 is an exploded view illustrating a second modification of the staple which is applied by the stapler shown in FIG. 12.
Figure 29:
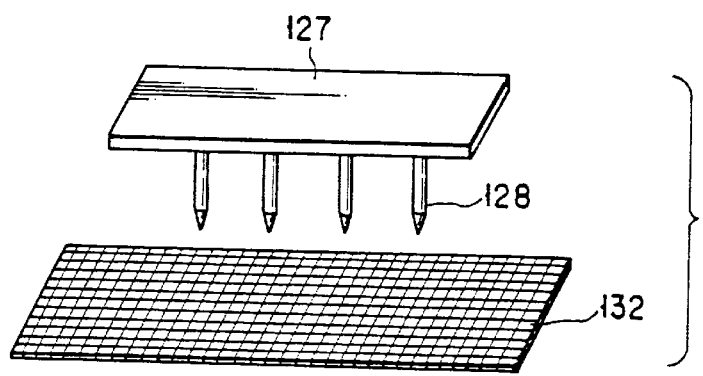
FIG. 29 is an exploded view showing a third modification of the staple which is applied by the stapler shown in FIG. 12.

The stapler 40 can apply other types of staplers which are shown in FIGS. 28 and 29. The staple shown in FIG. 28 differs from the stapler shown in FIG. 27 in that a plurality of rings 131 replace the plate 129. The staple shown in FIG. 29 differs from the stapler shown in FIG. 27 in that a meshed plate 132 having grids replaces the plate 129.

FIGS. 30A and 30B shows a staple 133 of so-called "magic tape type." The staple 133 has a number of arch-shaped projections 134 which protrude from a half of the lower side as shown in FIG. 30A, and also a number of J-shaped projections 135 protrude from the entire upper side. Each of the J-shaped projections 135 can catch one arch-shaped projection 134. The staple 133 is made of resin which can be absorbed into, or is compatible with, body tissues.

How to ligate a tubular organ (e.g., a blood vessel) by using the staple 133 will be described, with reference to FIG. 31. First, the staple 133 is wound tight around the severed edge portions of a tubular organ 137, thereby tying them together. Then, a heater 138 is put in contact with the arch-shaped projections 134, fusing the projections 134 to the upper side of the staple 133, whereby the tubular organ 137 is ligated. The staple 133 wound around the tubular organ 137 is a strip having a first portion and a second portion which hold the opposing parts of the organ 137, respectively.

The magic-tape type staple 133 can be applied to ligate tubular organs of various sizes, and can adjust the tightening the organs to any desired degree.

A clip applicator 140, which is a ninth embodiment of this invention, will be described with reference to FIGS. 32A and 32B. This applicator 140 is designed to apply a clip 152 of the same type as shown in FIG. 6. The distal end of the applicator 140 contains a Langevin-type ultrasonic oscillator 141 which has a horn at its tip. Connected to the distal end of the oscillator 141 is an oscillation-transmitting member 142. The member 142 comprises an oscillation-transmitting body 143 and a tip 144. The body 143 has a threaded hole. The tip 144 has a threaded portion set in screw engagement with the threaded hole of the body 143.

An L-shaped member 145 is located near the tip 144 of the oscillation-transmitting member 142. The member 145 has a distal end portion 145a located in front of the tip 144, spaced apart therefrom by a predetermined distance. The L-shaped member 145 is connected at rear end to a support pipe 146, which in turn is fastened to a sliding member 147. The sliding member 147 is slidably mounted on the distal end portion of a case 148 containing the ultrasonic oscillator 141. The case 148 has a grip 149 at which the applicator 140 can be held by hand. The ultrasonic oscillator 141 is connected to a drive circuit 150, which is connected to a drive signal generator 151.

In operation, the drive circuit 150 amplifies a drive signal the generator 151 has output. The amplified drive signal is supplied to the ultrasonic oscillator 141. Driven by the signal, the oscillator 141 generate ultrasonic oscillation, which is applied to the oscillation-transmitting body 143 and hence to the tip 144. The body 143 has such a length that the oscillation amplitude is maximal (i.e., with the anti-node located) at the end face of the tip 144.

The applicator 140 is operated as follows, in order to apply the clip 152. First, the clip 152 is clamped between the tip 144 and the distal end portion 145a of the L-shaped member 145. Next, the sliding member 147 is slid toward the case 148, moving the portion 145a toward the tip 144. The clip 152 is thereby collapsed, with its legs contacting each other at their tips. As a result, the clip 152 constricts a tubular organ (not shown) placed between the legs with an appropriate force. In other words, the clip 152 held between the tip 144 and the L-shaped member 145 clamps the organ. In this condition, the ultrasonic oscillator 141 is driven, applying ultrasonic oscillation to the tip 144 for a predetermined time. During this time, the contacting legs of the clip 152 undergo dynamic friction, generating heat and eventually fusing to each other. As a result, the clip made of resin closes permanently, clipping the tubular body steadfastly.

A stapler 155, which is a tenth embodiment of this invention, will be described with reference to FIGS. 33, 34, 35, 36A, 36B.

As FIG. 33 shows, this stapler 155 comprises a sheath 156 to be inserted into a tubular organ such as intestine, a stapling section 157 coupled to the distal end of the sheath 156, and an operation section 158 connected to the proximal end of the sheath 156.

Figure 34:
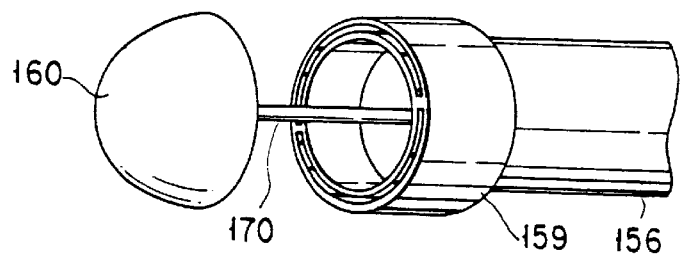
FIG. 34 is a perspective view showing the distal end portion of the stapler shown in FIG. 33.

As clearly shown in FIG. 34, the stapling section 157 comprises a hollow cylindrical housing 159 atttached to the distal end of the sheath 156, and an anvil 160 located at the front of the housing 159. As shown in FIG. 33, the housing 159 contains a staple pusher 161 and a cylindrical cutter 162, which can be moved back and forth. The stable pusher 161, which is a hollow cylinder, is used to push a first ring 173 (later described) toward the anvil 160. The cutter 162 is provided for cutting off the unnecessary portions of the tubular organ after the two severed parts of the organ have been stapled together.

Figure 35:
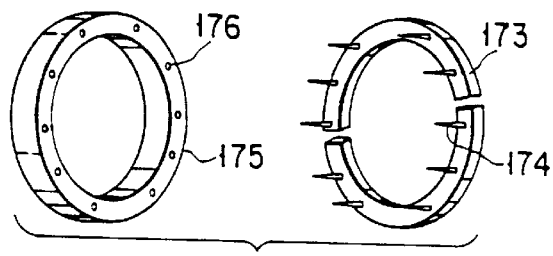
FIG. 35 is an exploded view illustrating a staple which is applied by the stapler of FIG. 33.

As is shown in FIG. 35, the staple to be applied by the stapler 155 comprises two rings 173 and 175. The first ring 173 has a plurality of styluses 174 which protrude in parallel to one another and spaced apart in the circumferential direction of the ring 173. The second ring 175 is removably held in the annular groove (not shown) cut in the back of the anvil 160. The ring 175 has as many holes 176 as the styluses 174, into which the styluses 174 will be inserted. Both rings 173 and 175 are made of resin which is absorbable absorbed into, or is compatible with, body tissues.

Referring back to FIG. 33, the operation section 158 comprises a housing 163 and a sliding member 164. The housing 163 is fixed to the sheath 156, and the sliding member 164 can move back and forth within the housing 163. A handle 166a is formed integral with the housing 163 and extending downward therefrom. Another handle 166b is formed integral with the sliding member 164 and extends downwards therefrom. Both handles 166a and 166b can be grasped so that the handle 116 be moved toward the handle 166a, thereby to slide the member 164 forward against the bias of a compression spring 165 contained in the sliding member 164.

As can be understood from FIG. 33, the sliding member 164 is a hollow member and contains an ultrasonic oscillator 167. The oscillator 167 is biased onto the inner front wall of the sliding member 164 by means of a compression spring 168. A hollow oscillation-transmitting member 169, which is a hollow cylinder, is coupled by a horn to the front end of the oscillator 167. The distal end of the member 169 is coupled to the rear end of the staple pusher 161, whereby the oscillation of the oscillator 167 is transmitted to the staple pusher 161 via the horn and the member 169. An anvil shaft 170 extends through the oscillation-transmitting member 169. The shaft 170 has a threaded end protruding from the housing 159 and set in screw engagement with a knob 171 which is rotatably connected to the rear end of the housing 159. When the knob 171 is turned in one direction and the other, the anvil shaft 170 is moved back and forth, whereby the space between the hollow cylindrical housing 159 and the anvil 160. The ultrasonic oscillator 167 is connected by a lead line 177 to an oscillator-driving circuit 178, which in turn is connected to a drive signal generator 179.

Figure 36A:
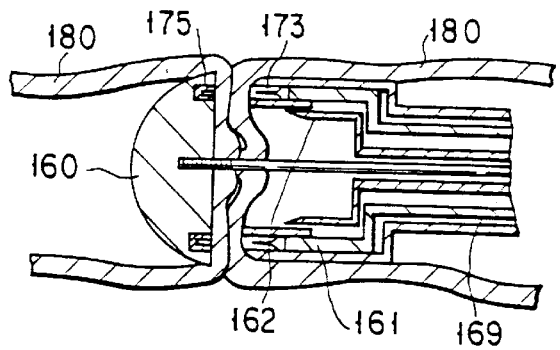
FIGS. 36A and 36B are diagrams explaining how the stapler of FIG. 33 is operated to stitch together two severed parts of a tubular organ.

The stapler 155, thus constructed, is operated as follows, to apply the staple shown in FIG. 35. First, the knob 171 is turned in a prescribed direction, moving the anvil 160 toward the hollow cylindrical housing 159, thereby clamping the abutting ends of two severed parts of a tubular organs 180 between the housing 159 and the anvil 160 as is shown in FIG. 36A. Then, the handles 166*a* and 166*b* are gripped, moving the handle 166*b* and hence sliding the member 164 forward. As a result, the first ring 173 of the staple is pushed out of the hollow cylindrical housing 159, whereby the styluses 174 of the first ring 173 pierce the abutting walls of the severed parts of a tubular organ 180 and fit into the holes 176 of the second ring 175. Thus, the severed parts of the organ 180 are fastened together.

Figure 36B:
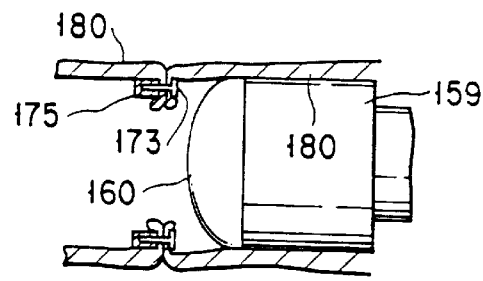

Next, the ultrasonic oscillator 167 is driven, generating ultrasonic oscillation. The oscillation-transmitting member 169 transmits the oscillation to the staple pusher 161 and hence to the first ring 173. The styluses 174 of the first ring 173, which are inserted in the holes 176 of the second ring 175, undergo dynamic friction with the second ring 175. The styluses 174 are thereby heated and fuse, whereby the rings 173 and 175 are connected to each other. Thereafter, the handle 166*b* is further pulled toward the handle 166*a*, the spring 168 is compressed, thrusting the cylindrical cutter 162 forward. As a result, the cutter 162 cuts off the unnecessary portions of the walls of the severed parts of the tubular organ 180, as is illustrated in FIG. 36B.

As described above, both rings 173 and 175 of the staple are oscillated at an ultrasonic frequency in the stapler 155 and fuse to each other by virtue of the heat generated by the dynamic friction between them. The stapler 155 can, therefore, achieve reliable suture of a tubular organ.

Figure 37:
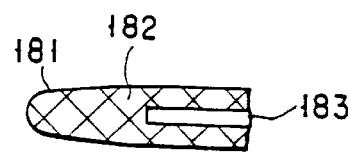
FIG. 37 is a plan view showing one of the two jaws of a clip applicator according to an eleventh embodiment of the invention.
Figure 38:
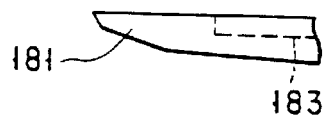
FIG. 38 is a side view showing the jaw shown in FIG. 37.

FIGS. 37 and 38 show one of jaws 181 of a clip applicator which is an eleventh embodiment of the present invention. The clip applicator has a pair of jaws 181 for holding a clip between them. Each jaw 181 has a clip-holding surface which has of a stylus-holding section 182 and a clip-holding groove 183. The stylus-holding section 182 comprises a net-shaped projections made of tungsten carbide.

Figure 39A:
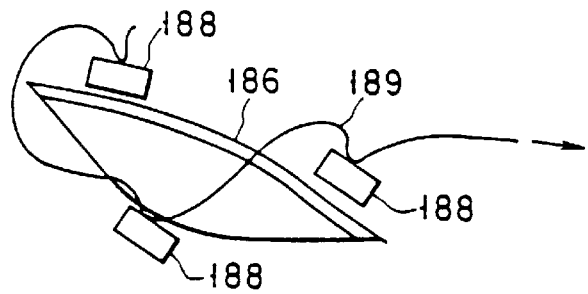
FIGS. 39A and 39B are diagrams explaining how a clip applicator according to a twelfth embodiment of the invention apply a plurality of clips, gathering and stitching together the tissues.
Figure 39B:
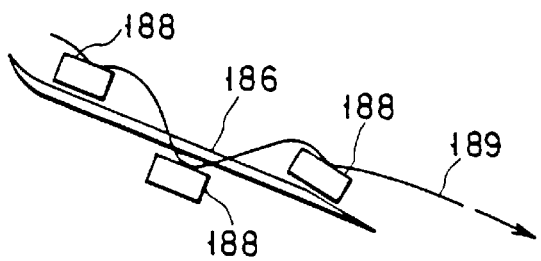

FIGS. 39A and 39B explain how a clip applicator according to a twelfth embodiment of the invention apply a plurality of clips 188 in order to gather and stitch together the tissues on the sides of a wound. As shown in FIG. 39A, the clips 188 loosely connected by a thread 189 are fixed to both sides of the wound in staggered fashion. Then, the thread is pulled, moving the clips 188 on one side of the would toward those on the other wide thereof as shown in FIG. 39B. As a result, the tissues on the sides of the wound are gathered and stitched to each other.

A clip applicator 191, which is a thirteenth embodiment of the present invention, will be described with reference to FIGS. 40, 41 and 42 and FIGS. 43A, 43B and 43C.

Figure 40:
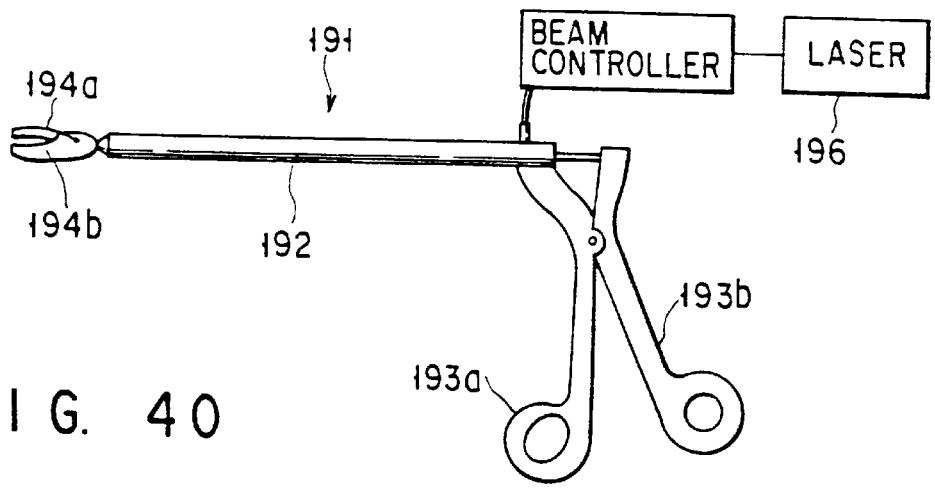
FIG. 40 is a schematic representation of a clip applicator which is a thirteenth embodiment of the present invention.

As can be understood from FIG. 40, the clip applicator 191 comprises a sheath 192, two handles 193*a* an 193*b* both connected to the proximal end of the sheath 192, and a pair of jaws 194*a* and 194*b* connected to the distal end of the sheath 192. The sheath 192 can be inserted into a body cavity, guided through a tubular instrument such as a trocar. The handle 193*a* is fixed to the sheath 192, and the handle 193*b* is rotatably coupled to the middle portion of the fixed handle 193*a*. The lower jaws 194*b* is fastened to the distal end of the sheath 192, and the upper jaw 194*a* is rotatably coupled to the lower jaw 194*b*. A connecting rod extends through the sheath 192, connecting the upper jaw 194*a* to the upper end of the rotatable handle 193*b*. Hence, when the rotatable handle 193*b* is moved toward and away from the fixed handle 193*a*, the rod moves the upper jaw 194*a* into its open position and into its close position.

Figure 41:
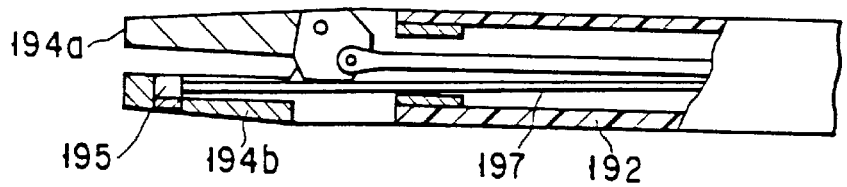
FIG. 41 is a partly sectional side view showing the distal end portion of the clip applicator shown in FIG. 40.

As is shown in FIG. 41, the lower jaw 194*b* has a hole 195 opening in the side opposing the upper jaw 194*a*. As shown in FIG. 40, a laser 196 and a beam controller are located outside the clip applicator 191. The laser 196 is connected to the beam controller. An optical fiber 197 extends from the beam controller to the hole hole 195, passing through the sheath 192.

Figure 42:
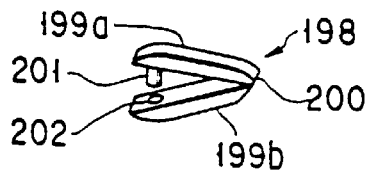
FIG. 42 is a perspective view illustrating a clip which the applicator of FIG. 40 is to apply.

FIG. 42 shows a clip 198 which the applicator 191 applies. The clip 198 is made of resin, having an upper leg 199*a* and a lower leg 199*b* which are connected to each other at a hinge portion 200. The upper leg 199*a* has a pin 201 protruding toward the lower leg 199*b*. The lower leg 199*b* has a through hole 202 so positioned as to received the pin 201 when the legs 199*a* and 199*b* abut on each other.

Figures 43A, 43B, 43C:
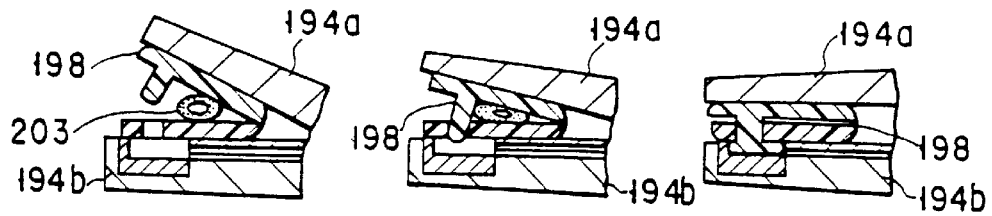
FIGS. 43A, 43B, and 43C are diagrams explaining how the clip applicator is used to ligate a tubular organ.

The clip applicator 191 is manipulated as follows, in order to apply the clip 198 to ligate a tubular organ. The clip 198 is held between the jaws 194*a* and 194*b* as shown in FIG. 43A, and a tubular organ 203 is placed between the legs 199*a* and 199*b* of the clip 198. Next, as shown in FIG. 43B, the handles 193*a* and 193*b* are gripped, moving the handle 193*b* toward the handle 193*a*, whereby putting the upper jaw 194*a* into the close position. As shown in FIG. 43C, the clip 198 is closed, with its pin 201 inserted into the hole 202. In this condition, a laser beam is applied from the laser 196 into the hole 195 of the lower jaw 194*b* through the beam controller and the optical fiber 197. The thermal energy of the beam melts that portion of the pin 201 which is inserted in the hole 202, fusing the same to the lower side of the lower leg 199*b*.

Once the lower end of the pin 201 has been thus fused to the lower side of the leg 199*b*, the clip 198 does not release the tubular organ 203. Thus, the clip applicator 191 can ligate tubular organs with reliability.

The clip applicator 191 is of the type designed to apply one clip at a time. Instead, it may be of the type which can apply a plurality of clips at a time.

A stapler 210 according to a fourteenth embodiment of the invention will be described, with reference to FIGS. 44, 45, and 46.

Figure 44:
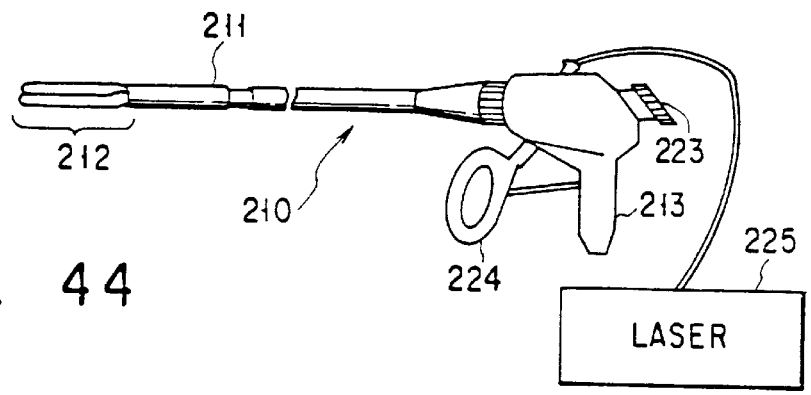
FIG. 44 is a side view of a stapler according to a fourteenth embodiment of the present invention.

As is evident from FIG. 44, the stapler 210 comprises an insertion section 211, a stapling section 212 attached to the distal end of the insertion section 211, and an operation section 213 fixed to the proximal end of the insertion section 211.

Figure 45:
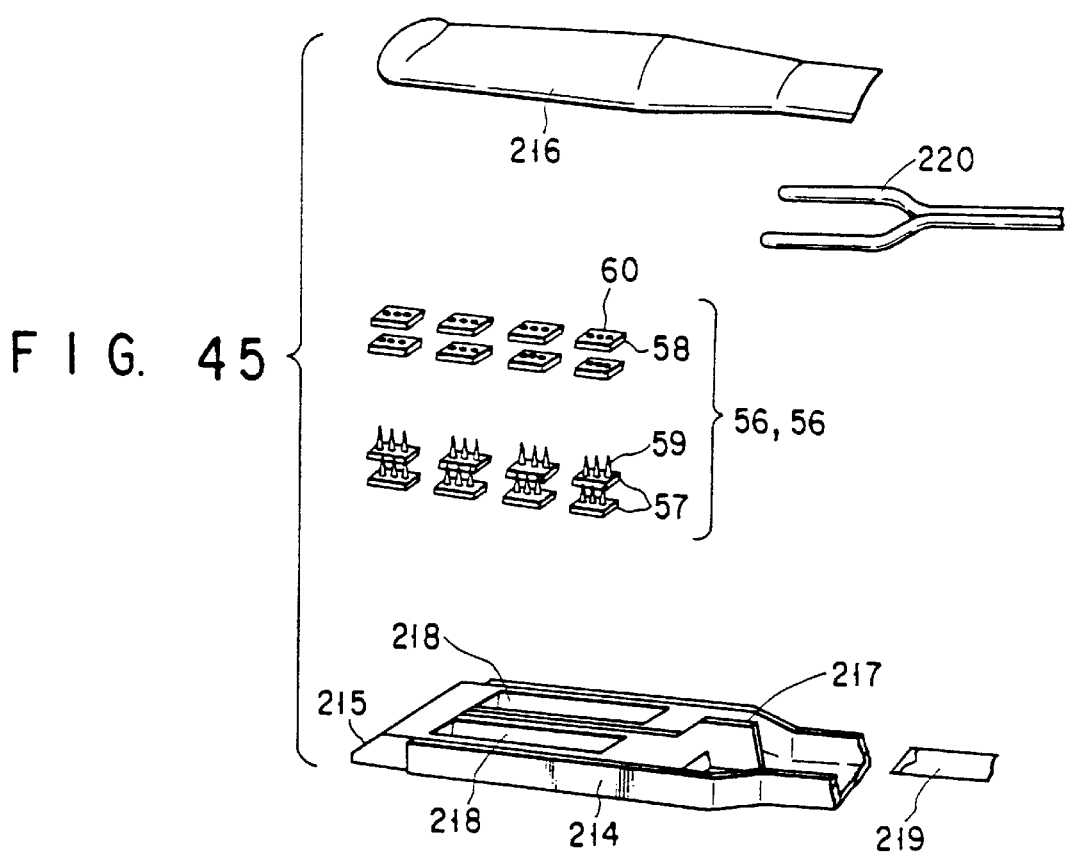
FIG. 45 is an exploded view showing the distal end portion of the stapler shown in FIG. 44.

As FIG. 45 shows, the stapling section 212 comprises a casing 214, a cartridge 215, and an anvil 216. The casing 214 is generally a top-opening rectangular box and secured to the distal end of the insertion section 211. The cartridge 215 is removably contained in the casing 214. The anvil 216 is hinged at its read end to the rear end of the casing 214 and can therefore be rotated to an open position and a closed position; it is normally in the closed position, covering the top (i.e., staple-holding surface) of the casing 214. A knife-guiding groove 217 is formed in the top surface of the casing 214, extending along the axis of the casing 214 for guiding a knife 219 used for sever body tissues. Also formed in the top surface of the casing 214 are two rectangular recesses 218 located on the sides of the groove 217, for holding the bases 57 of staples 56. The staple bases 57 are placed in each recess 218. The staples 56 are identical to those shown in FIG. 12, and will not described here again.

The anvil 216 contains a laser probe 220 and a heat-resistant member 221. The laser probe 220 is used to heat and deform deforming the tips of the pins 59 of each staple 56. As shown in FIG. 46A and 46B, the heat-resistant member 221 is positioned, opposing the tip of the laser probe 220. The anvil 216 also contains staple covers 58.

Referring to FIG. 44 again, the operation section 213 has a handle 223 for opening and closing the anvil 216, and a firing handle 224 for applying a laser beam to the probe 220. A laser 225 is connected to the operation section 213.

The stapler 210 is manipulated in the following way. First, the stapling section 212 is positioned such that the body tissues 222 are placed between the cartridge 215 and the anvil 216. Next, the handle 223 is operated, rotating the anvil 216 to the closed position and, hence, clamping the body tissues 222. The pins 59 of each staple 56 pierce the tissues 222 and slip into the holes 60 of the cover 58 and protrude from the cover 58, as is illustrated in FIG. 46A. The firing handle 224 is pulled, applying a laser beam from the laser 225 to the laser probe 220 and hence to the tips of pins 59. The pins 59 are heated and fused onto the upper surface of the cover 58 as is shown in FIG. 46B. As a result, the staples 56 fasten the body tissues 222 together—as steadfastly as in the staplers shown in FIGS. 11 and 19.

A clip applicator 230, which is a fifteenth embodiment of the invention, will be described with reference to FIGS. 47 to 55.

Figure 48:
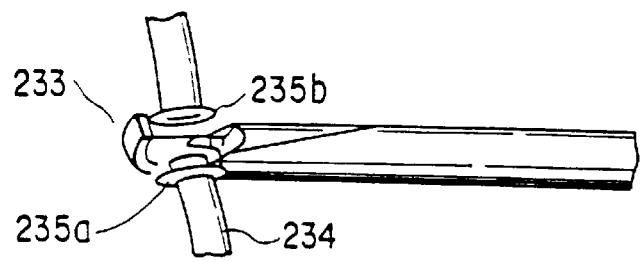
FIG. 48 is a perspective view showing a clip applicator which is a fifteenth embodiment of the present invention.

As shown in FIG. 47, the clip applicator 230 comprises an operation section 231, an insertion tube 232 extending from the distal end of the operation section 231, and a clip-applying section 233 connected to the distal end of the tube 232. The tube 232 is to be inserted into a body cavity, and the clip-applying section 233 is designed to apply two clips 235a and 235b to ligate a tubular organ 234 such as a blood vessel and subsequently sever the organ 234, as is illustrated in FIG. 48.

Figure 49:
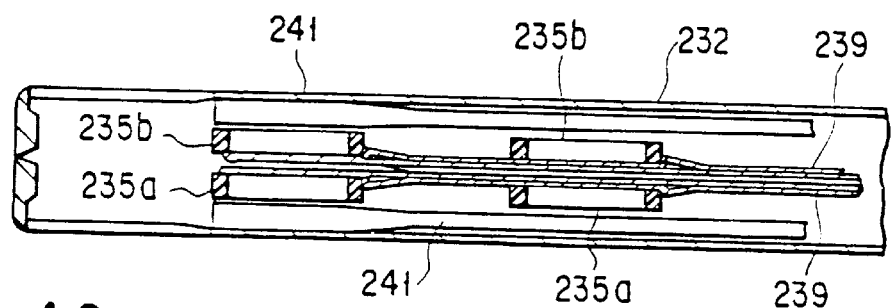
FIG. 49 is a sectional view showing the distal end portion of the clip applicator shown in FIG. 48.
Figure 50:
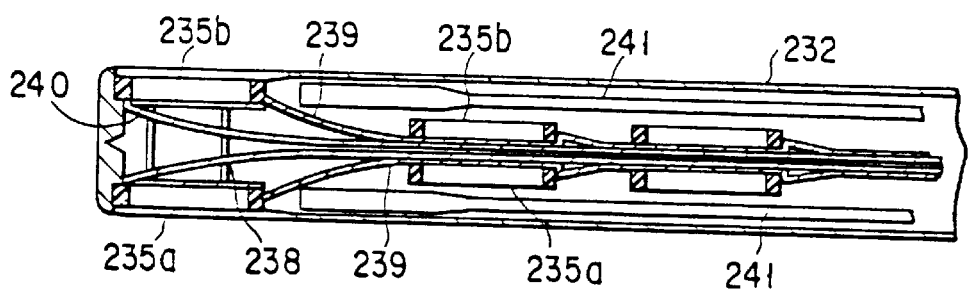
FIG. 50 is a diagram explaining how to manipulate the clip applicator of FIG. 48.
Figure 51:
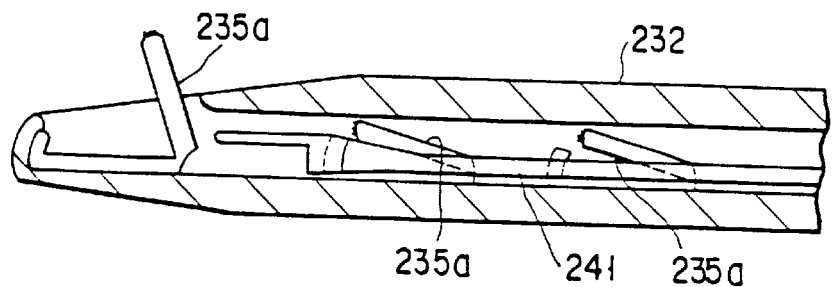
FIG. 51 is also a diagram explaining how to manipulate the clip applicator of FIG. 48.

Both clips 235a and 235b are made of resin which can be absorbed into body tissues. As shown in FIG. 52, each clip has a sawtoothed portion 236 at one end, and a holder portion 237 at the other end. The holder portion 237 is designed to hold the sawtoothed portion 236. The clips 235a and 235b are connected by two strips 238 of adhesive tape. As shown in FIG. 49, the clips 235a and 235b are contained in the insertion tube 232 and can be pushed to the clip-applying section 233 by means of a pair of clip-pushing springs 239 which extend through the insertion tube 232. Another pair of springs 240 extend through the tube 232, between the clip-pushing springs 239. When the springs 240 are thrust to the clip-applying section 233, their distal end portions spread sideways by their own bias, moving two clips 235a and 235b already pushed into the clip-applying section 233 as is illustrated in FIG. 50. As a result, the clips 235a and 235b are placed at positions where they oppose the distal ends of clip-holders 241 located within the insertion tube 232.

The clip holders 241 are connected to an ultrasonic oscillator 242 which is incorporated in the operation section 231 as shown in FIG. 47, so that the ultrasonic oscillation generated by the oscillator 242 may be transmitted to the clip holders 241. The ultrasonic oscillator 242 can be moved back and forth in the operation section 231 when a handle 243 (FIG. 47) is operated. More precisely, when the handle 243 is squeezed, the oscillator 242 is pushed forward. As shown in FIG. 55, a knife 245 extends through the insertion tube 232 and can slide along the axis of the tube 232 for cutting the tubular organ 234 and the strips 238 of adhesive tape.

In operation, the clips 235a and 235b pushed into the clip-applying section 233 are closed by operating the clip holders 241. This done, the ultrasonic oscillator 242 is energized, generating ultrasonic oscillation. The clip holders 241 transmits the oscillation to the closed clips 235a and 235b. By virtue of the ultrasonic oscillation, heat is generated between the sawtoothed portion 236 and holder portion 237 of each clip which are in frictional contact. The portions 236 and 237 of the clip are thereby fused together. As a result, the clips 235a and 235b would not open, reliably clamping the tubular organ 234.

Since the sawtoothed portion 236 and holder portion 237 of each clip are heated by ultrasonic oscillation, the remaining parts of the clip are not heated so much as to lose their rigidity.

The legs of the clip hitherto been used to ligate a tubular organ by mechanical means (e.g., latches) needs to have a large contacting surfaces to ensure reliable ligation of the organ. Inevitably it large and thick as a whole; it requires a large incision for penetration into a body cavity and is difficult to handle. By contrast, the clips 235a and 235b are sufficiently small since the legs of each clip are fastened to each other by ultrasonic oscillator, not by any mechanical means.

Figure 56:
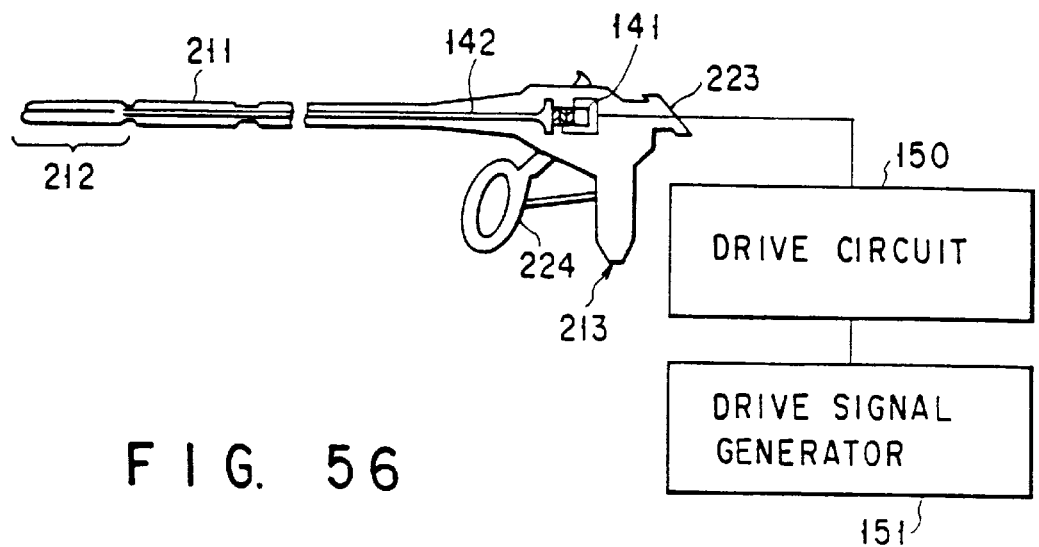
FIG. 56 is a schematic representation of a stapler which is a sixteenth embodiment of this invention.
Figure 57:
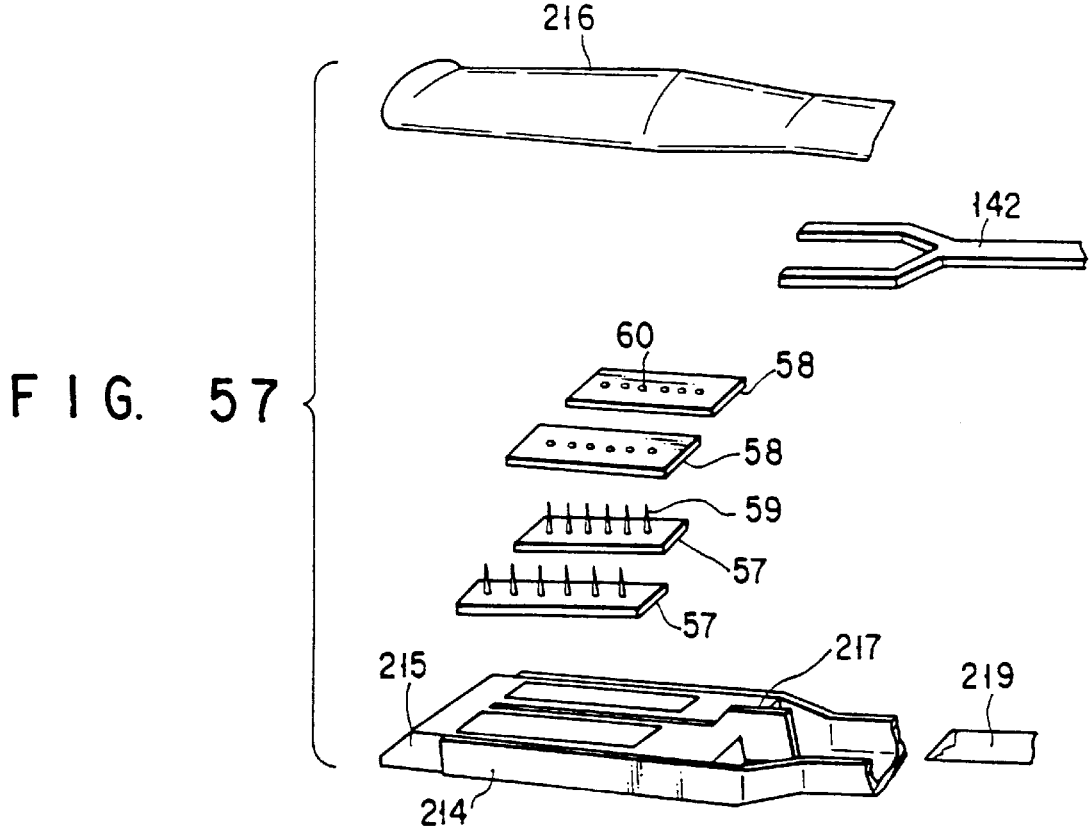
FIG. 57 is an exploded view showing the distal end portion of the stapler shown in FIG. 56.

A stapler, which is a sixteenth embodiment of the invention, will be described with reference to FIGS. 56, 57, and 58. This stapler is identical to the stapler 210 shown in FIGS. 44 and 45, except that the laser probe 220 is replaced by the ultrasonic oscillator 141 and the oscillation-transmitting member 142, both shown in FIG. 32, in order to fasten the staple bases 57 and the staple covers 58 by means of ultrasonic oscillation. Once the base 57 and corresponding cover 58 of each staple 56 are fused together by virtue of ultrasonic oscillation as shown in FIG. 58, the staple 56 keeps holding body tissues 222 in stead fast connection.

Another clip applicator, which is a seventeenth embodiment of the present invention, will be described with reference to FIGS. 59, 60, and 61.

As can be seen from FIG. 59, the clip applicator comprises an operation section 250 and an insertion section 251 extending from the distal end of the operation section 250. The operation section 250 contains an ultrasonic oscillator 252 and a horn 253, and has a handle 254 and a grip 255. An oscillation-transmitting member 256 extends forward from the horn 253 through the insertion section 251. The member 256 has an oscillating tip 257. A clip holder 258 is inserted in the distal end of the insertion section 251 and can be moved along the axis of the section 251 as the handle 254 is operated. The ultrasonic oscillator 252 is connected to a drive circuit 259, which in turn is connected to a drive signal generator 260.

FIG. 61 shows a clip 261 which the applicator applies to ligate a body organ. The clip 261 is a molding made of thermoplastic resin. It consists of a pair of legs 262a and 262b and a hinge 263 connecting the legs 262a and 262b at one end. A plurality of tiny projections 264 protrude from the opposing sides of the tips of the legs 262a and 262b. The leg 262a is thinner than the leg 262b and can be bent more easily.

As is shown in FIG. 60, the clip holder 258 has an L-shaped anvil 265 which opposes the oscillating tip 257 of the oscillation-transmitting member 256. The clip 261 is held, with the legs 262a and 262b abutting on the oscillating tip 257 and the anvil 265, respectively. The the oscillation-transmitting member 256 is held in a retreated position by a spring (not shown), and the anvil 265 can be moved backwards by operating the handle 254.

The clip applicator shown in FIG. 59 is operated in the following way. First, the clip 261 is held between the anvil 265 and the oscillating tip 257 of the member 256 as is shown in FIG. 60. Then, body tissues to be fastened together are moved into the gap between the legs 262a and 262b of the clip 261, while being observed through an endoscope. Next, the handle 254 is pulled, moving the anvil 265 backwards. The clip 261 is thereby closed, clamping the tissues. In this condition, the ultrasonic oscillator 252 is driven, generating ultrasonic oscillation. The oscillation-transmitting 256 transmits the oscillation to the clip 261. The projections 264 of the leg 262a and those 264 of the leg 262b, which abut in point contact, are oscillated and fused together, whereby the legs 262a and 262b are permanently connected to each other.

Due to the point contact between the projections of the leg 262a and those of the leg 262b, heat is generated concentratedly at the tips of the projections 264, whereby the projections 264 can be fused within a short time. Even if the tissues are wet with body fluid such as blood, the projections reliably abut on one another, the legs 262a and 262b can be fastened together readily and steadfastly.

Figure 62:
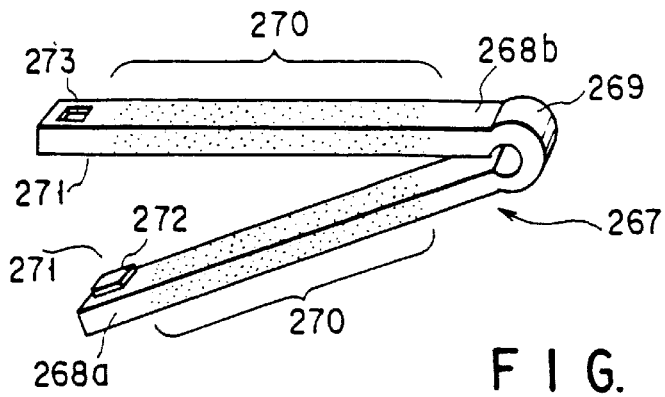
FIG. 62 is a perspective view showing a clip which is an eighteenth embodiment of the present invention.

FIG. 62 shows a clip 267 which is an eighteenth embodiment of the present invention. The clip 267 comprises a pair of legs 268a and 268b and a hinge 269 connecting the legs 268a and 268b at one end. All components of the clip 267 are formed integral, made of resin. Those portions 270 of the legs 268a and 268b, which extend between the hinge 269 and the free ends of the legs 268a and 268b, are made of foamed resin or porous resin. The mutually opposing sides of the tips of the legs 268a and 268b serve as fusing surfaces 271. A rectangular fuse 272 is mounted on the surface 271 of the leg 268a. The leg 268b has a rectangular recess 273 formed in that side of its tip which faces away from the fusing surface 271. The recess 273 serves to transmit ultrasonic oscillation readily to the leg 268b.

When the clip 267 is held and closed at the distal end of the applicator shown in FIG. 59 (i.e., the seventeenth embodiment) and then subjected ultrasonic oscillation, the fuse 272 is fused to the fusing surface 271 of the legs 268a and 268b, whereby the legs 268a and 268b are deformed and fastened together firmly. The ultrasonic oscillation applied to the recess 273 is not well transmitted to the portions 270 of the clip 267 because the portions 270 are less dense than any other portions. Hence, the portions 270 generate far less heat, if any, scarcely affecting the tissues clamped between the legs 268a and 268b with oscillation or heat. Not the entire portions 270, but only the surface regions thereof may be made of foamed resin or porous resin. Alternatively, a sponge-like resin layer may be bonded to the inner surface of each leg.

Figure 63:
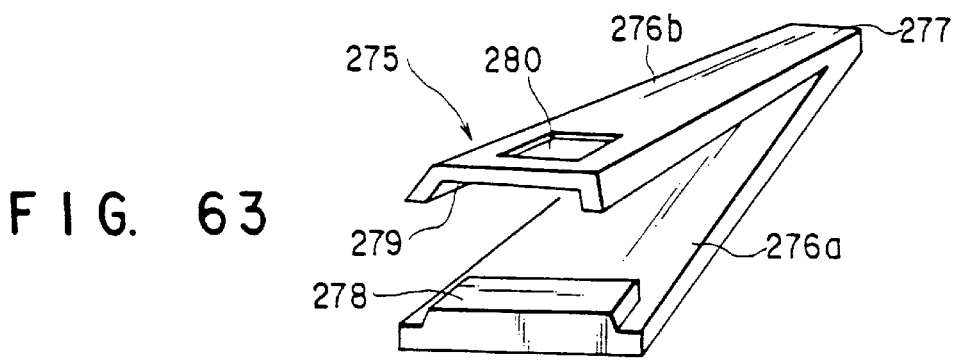
FIG. 63 is a perspective view illustrating a clip which is a nineteenth embodiment of the invention.

FIG. 63 shows a clip 275 which is a nineteenth embodiment of the present invention. The clip 275 comprises a pair of legs 276a and 276b and a hinge 277 coupling the legs 276a and 276b at one end. All components of the clip 275 are formed integral, made of thermoplastic resin. The leg 276a has a raised portion 278 on the inner surface of its free end, whereas the leg 276b has a recessed portion 279 formed in the inner surface of its free end. The leg 276b has a rectangular recess 280 formed in the outer side of its free-end portion. When to be used, the clip 275 is held in the distal end of the applicator shown in FIG. 59 (i.e., the seventeenth embodiment), with the oscillating tip 257 of the member 256 abutting on the bottom of the rectangular recess 280. Once the clip 275 is closed, clamping tissues between the legs 276a and 276b, the raised portion 278 of the leg 276a fits into the recessed portion 278 of the leg 276b. The legs 276a and 276b are thereby prevented from displacing sideways from each other. This helps to shorten the time required for fusing the free ends of the legs 276a and 276b together.

Figure 64:
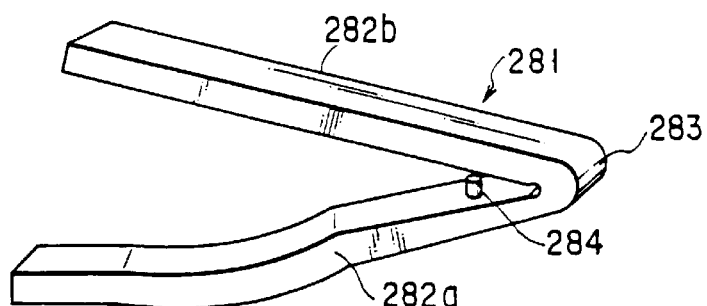
FIG. 64 is a perspective view showing a clip which is a twentieth embodiment of this invention.

FIG. 64 shows a clip 281 which is a twentieth embodiment of this invention. Like those shown in FIGS. 61, 62, and 63, the clip 281 comprises a pair of legs 282a and 282b and a hinge 283 coupling the legs 282a and 282b at one end, and all of its components are formed integral and made of thermoplastic resin. The leg 282a has a projection 284 protruding from that part of its inner surface which is close to the hinge 283. To ligate tissues together, the clip 281 is closed, holding the tissues between the legs 282a and 282b, with the projection 284 abutting on the inner surface of the leg 282b. In this condition, ultrasonic oscillation is applied to the clip 281. The projection 284 is thereby melted and fused to the leg 282b, whereby the legs 282a and 282b are fastened to each other, clamping the tissues steadfastly. As can be understood from FIG. 64, the middle portion of the leg 282a is gently curved away from the leg 282b.

Since no projections protrude from the free-end portion of the leg 282a or 282b, body tissues can be smoothly guided into the gap between the legs 282a and 282b; the projection 284, located near the hinge 283, does not impede the guiding of the tissues. Further, since the middle portion of the leg 282a is gently curved away from the leg 282b, the tissues clamped between the legs 282a and 282b do not hinder the fusing of the projection 284. The clip 281 can be applied to fasten flat tissues together, too.

A twenty-first embodiment of the present invention will be described, with reference to FIG. 65, FIGS. 66A, 66B and 66C, and FIG. 67.

Figure 65:
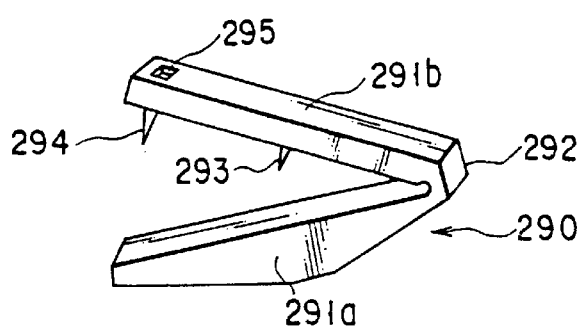
FIG. 65 is a perspective view showing a clip which is to be applied by a clip applicator according to a twenty-first embodiment of the present invention.

FIG. 65 shows a clip 290 used in this embodiment. Like those shown in FIGS. 61, 62, 63, and 64, the clip 290 comprises a pair of legs 291a and 291b and a hinge 292 coupling the legs 291a and 291b at one end, and all of its components are formed integral and made of thermoplastic resin. The clip 290 has two styluses 293 and 294 protruding from the inner surface of the leg 191b and located at the middle and the free-end portions of the leg 291b, respectively. The stylus 293 is shorter than the stylus 294. The leg 291b has a rectangular recess 295 formed in the outer side of the free-end portion, for efficiently transmitting ultrasonic oscillation to the leg 291b.

Figure 67:
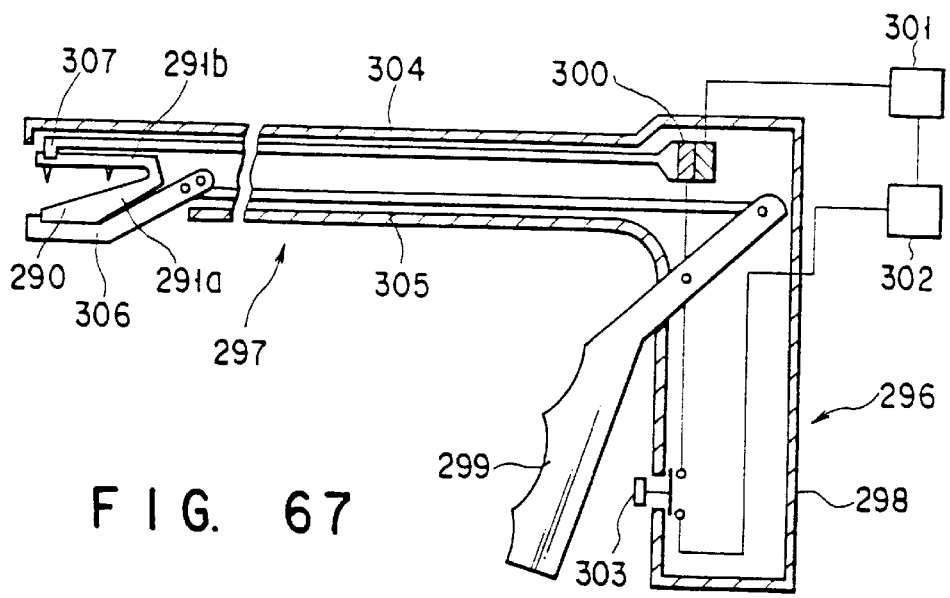
FIG. 67 is a sectional side view showing the applicator which is the twenty-first embodiment of the invention.

FIG. 67 shows an ultrasonic clip applicator designed to apply the clip 290. As is shown in the figure, the applicator comprises an operation section 296 and an insertion section 297. The operation section 296 comprises a grip 298 and a handle 299 rotatably connected to the grip 298. The grip 298 contains an ultrasonic oscillator 300. A push-button switch 303 consisting of a push button (i.e., movable contact) and two stationary contacts. One stationary contact is electrically connected to the oscillator 300, which in turn is connected to a drive circuit 301 provided out side the grip 298. The other stationary contact is electrically connected to an oscillation circuit 302, which is located outside the grip 298 and connected to the drive circuit 301.

The insertion section 297 contains a member 304 for transmitting ultrasonic oscillation and a link 305 for opening and closing a jaw 306. The link 305 has its proximal end connected to the handle 299 and its distal end coupled to the rear end of the jaw 306. The jaw 306 is rotatably coupled to the distal end of the insertion section 297. The oscillation-transmitting member 304 has an oscillating tip 307.

Figures 66A, 66B, 66C:
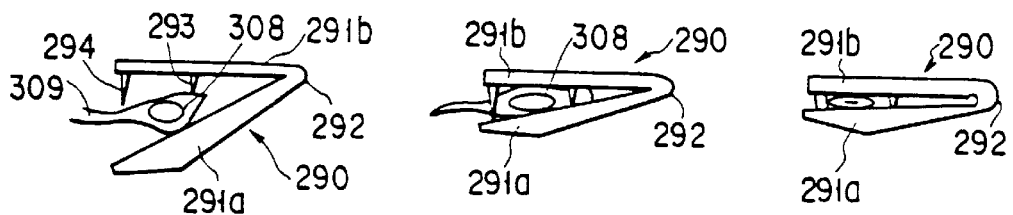
FIGS. 66A, 66B, and 66C are diagrams explaining how to apply the clip of FIG. 65 to ligate a tubular organ.

The clip applicator is manipulated as follows to apply the clip 290 in the following way. First, the clip 290 is held between the jaw 306 and the oscillating tip 307 as is shown in FIG. 67. Then, as shown in FIG. 66A, a tubular organ 308 (e.g., a blood vessel) is positioned in the gap between the legs 291a and 291b of the clip 290. Thereafter, the handle 299 is squeezed, rotating the jaw 306 and subsequently closing the clip 290 as shown in FIG. 66B. The tubular organ 308 is thereby clamped and collapsed between the legs 291a and 291b. Then, the push-button switch 303 on the grip 298 is pushed, driving the ultrasonic oscillator 300. The oscillator 300 generates ultrasonic oscillation, which is transmitted to the clip 290 by the oscillation-transmitting member 304.

The styluses 293 and 294, which pierce a layer of fat or the like, if any, and abut on the inner surface of the leg 291b, are fused at their tips, fixing the leg 291a to the leg 291b. Hence, the clip 290 is deformed in its closed state, ligating the tubular organ 308. Both styluses 293 and 294 can easily pierce the organ 308 by virtue of the ultrasonic oscillation applied to them.

Thus, even if some tissues have not been separated from the tubular organ 308, the clip 290 can reliably ligate the organ 308. Since the styluses 293 and 294 bite into the organ 308 as the clip 290 is closed by rotating the jaw 306, that portion of the organ 308 which should be ligated is not displaced from the clip 290.

Figure 68:
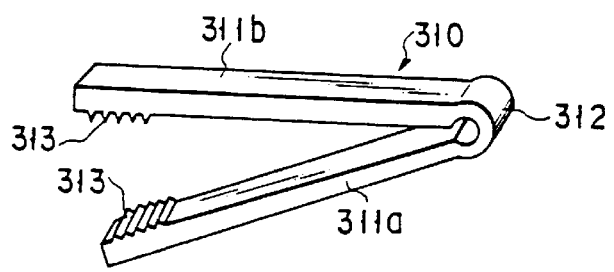
FIG. 68 is a perspective view showing a clip which is a twenty-second embodiment of the present invention.

FIG. 68 shows a clip 310 which is a twenty-second embodiment of the present invention. The clip 310 comprises a pair of legs 311a and 311b and a hinge 312 connecting the legs 311a and 311b at one end. All components of the clip 310 are formed integral and made of thermoplastic resin. Each leg has a serration 313 on the inner surface of its free-end portion. The serration 313 serves as fusing surface. The clip 310 is applied in the same way as the clips shown in FIGS. 61 to 65. The serrations 313 formed on the abutting end portions of the legs 311a and 311b can be readily fused together when ultrasonic oscillation is applied to the clip 310. The legs 311a and 311b can therefore be fastened together, creating a sufficient clamping or ligation force.

Figure 69:
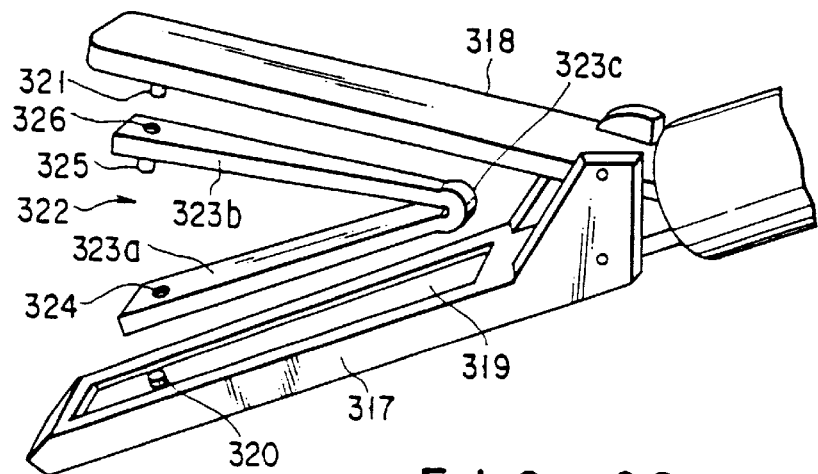
FIG. 69 is a perspective view illustrating the jaw of a clip applicator which is a twenty-third embodiment of this invention.
Figure 70:
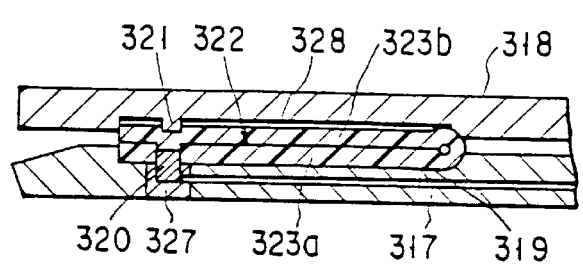
FIG. 70 is a sectional view showing the jaw of FIG. 69.

A twenty-third embodiment of the invention will be described with reference to FIGS. 69 and 70. FIG. 69 shows the distal end portion of a clip applicator according to this embodiment. As FIG. 69 shows, the applicator has a pair of jaws 317 and 318. The first jaw 317 has a clip-holding groove 319 formed in its inner surface and a rod-shaped heater 320 protruding from the bottom of the clip-holding groove 319. As is shown in FIG. 70, the heater 320 is held by an heat-insulating member 327 which is embedded in the first jaw 317. The second jaw 318 has a clip-holding groove 328 and a clip-holding projection 321 protruding from the bottom of the groove 328.

The jaws 317 and 318 are designed to close a clip 322. The clip 322 comprises a pair of legs 323a and 323b and a hinge 323a connecting the legs 323a and 323b at one end. All components of the clip 310 are formed integral and made of thermoplastic resin. The leg 323a has a through hole 324 in its free end portion, whereas the leg 323b has a projection 325 protruding from the inner surface of its end portion. The projection 325 is so positioned as to fit into the hole 324 of the leg 323a when the clip 322 is closed. The leg 323b has a hole 326 in the outer side of its end portion, for receiving the clip-holding projection 321 of the second jaw 318.

To load the clip 322 in the distal end portion of the clip applicator, the leg 323a is placed in the clip-holding groove 319 of the first jaw 317, and simultaneously the rod-shaped heater 320 is inserted into the hole 324 of the leg 323a. Further, the leg 323b is placed in the clip-holding groove 328 of the second jaw 318, and the clip-holding projection 321 of the second jaw 318 is inserted into the hole 326 of the leg 323b. As a result, the clip 322 is held between the jaws 317 and 318, in its open position.

The distal end portion of the clip applicator is guided into a body cavity and moved until the body tissues to be fastened together are caught in the gap between the legs 323a and 323b. Thereafter, the heater 320 is turned on, heating the projection 325 of the leg 232b and fusing the same to the leg 323a. The legs 323a and 323b are thereby permanently fastened to each other, clamping the tissues between them steadfastly.

It is only the projection 325 that the heater 320 heats. Since no other parts of the clip 322 are heated very little or not heated at all, the tissues are not thermally affected. The rod-shaped heater 320 may be replaced by a stylus-shaped one, so that the projection 325 may be heated more efficiently.

Figure 71:
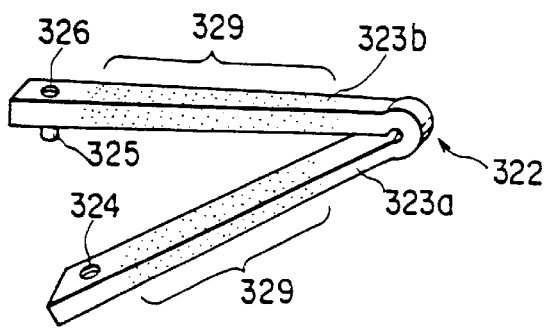
FIG. 71 is a perspective view showing a clip which is a twenty-fourth embodiment of the present invention.

FIG. 71 shows a clip which is a twenty-fourth embodiment of the present invention. This clip is identical to the clip 322 shown in FIG. 69, except that a heat-sensitive material, which changes color as it is heated, is contained in the middle portions 329 of legs 323a and 323b. The clip is applied by the same method as the clip 322 of FIG. 69. Hence it is possible to detect the temperature to which the legs 323a and 323b have been heated, from the color the middle portions 329 do present. This helps to heat and fuse the projection 325 appropriately.

A clip 330, which is a twenty-fifth embodiment of the invention, will be described with reference to FIGS. 72, 73, 74A, 74B, and 75. The clip 330 is of a type which is permanently closed by means of ultrasonic oscillation.

Figure 72:
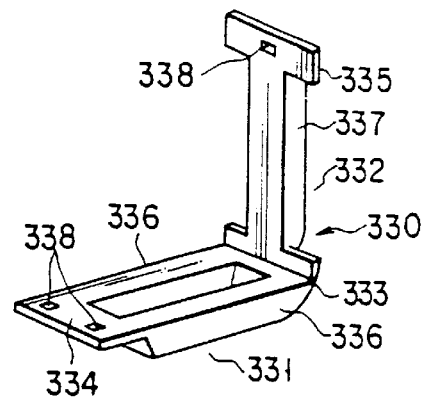
FIG. 72 is a perspective view illustrating a clip which is a twenty-fifth embodiment of the invention.
Figure 73:
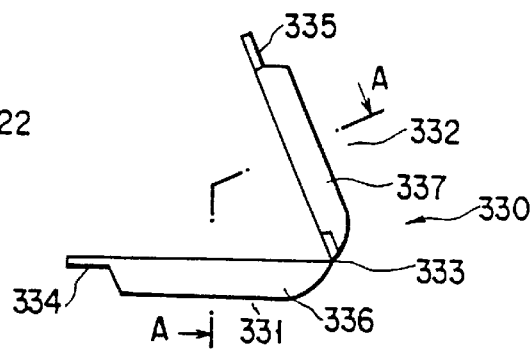
FIG. 73 is a side view of the clip illustrated in FIG. 72.
Figures 74A, 74B:
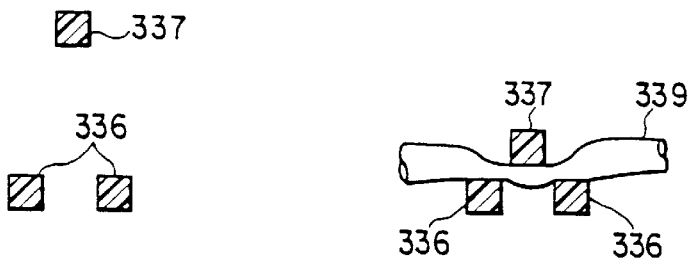
FIGS. 74A and 74B are cross-sectional views of the clip, taken along line A—A in FIG. 73.

As shown in FIG. 72, the clip 330 comprises a pair of legs 331 and 332 and a hinge 333 connecting the legs 331 and 332 at one end. All components of the clip 330 are formed integral and made of thermoplastic resin. The middle portions of the legs 331 and 332 function as tissue-clamping members. The legs 331 and 332 have thin plate-like end portions 334 and 335 which are to be fused together. The middle portion of the leg 331 is comprised of two parallel square bars 336, and that of the leg 332 is comprised of one square bar 337. These bars 336 and 337 are thicker than the end portions 334 and 335. The bars 336 are spaced apart for a distance slightly longer than the width of the bar 337. As long as the clip 330 remain open, the bars 336 and 337 assume such positions as shown in FIG. 74A. When the clip 330 is closed, the bar 337 will have its lower side substantially covering the space between the the bar 336, as is illustrated in FIG. 74B. The end portion 334 of the leg 331 has projections 338 on its inner surface. Similarly, the end portion 335 of the leg 332 has a projection 338 on its inner surface.

Figures 75, 76:
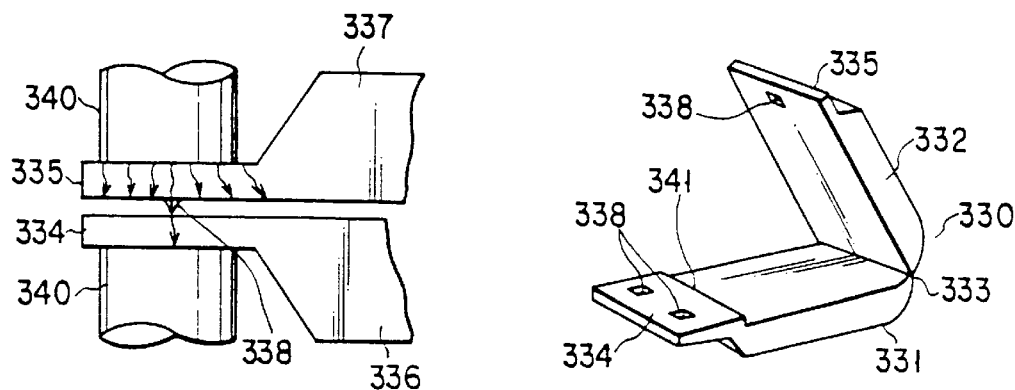
FIG. 75 is a diagram explaining how to fuse together the legs of the clip shown in FIG. 72.
FIG. 76 is a perspective view showing a clip which is a twenty-sixth embodiment of the invention.

The clip 330, thus constructed, is applied in the following way. The clip 330 is held in its open position, at the distal end of a clip applicator (not shown), which is guided into a body cavity. In the body cavity the distal end of the applicator is moved until a tubular organ 339 the clip 330 is to ligate is placed between the legs 331 and 332. Then, the clip 330 is closed, with the end portions 334 and 335 pressed together by the oscillating tips 340 of the applicator as is shown in FIG. 75. In this condition, the tips 340 applies ultrasonic oscillation to the end portions 334 and 335. The projections 338 of the end portion 334, which are in frictional contact with the end portion 335, and the projection 338 of the end portion 335, which is in frictional contact with the end portion 334, are heated and fused. Also, the end portion 334 and 335 are eventually fused together. As a result, the clip 330 firmly clamps the tubular organ 339.

Since the end portions 334 and 335 are thinner than the bars 336 and 337, the heat can hardly be transmitted to the bars 336 and 337 clamping the organ 339. Further, since the bars 336 and 337 do not contact one another, they have no friction among them and, hence, will generate no heat and will not fuse together. Hence, only the end portions 334 and 335 are fused together. Thus, the tubular organ 339 clamped by the bars will not be thermally affected at all.

FIG. 76 shows a clip 330 which is a twenty-sixth embodiment of the present invention. The clip 330 comprises a pair of legs 331 and 332 and a hinge 333 coupling the legs 331 and 332. The middle portions of the clip 332 are flat plates, not bars as those of the clip shown in FIG. 72. The leg 331 has a step 341 in the inner surface, so that when the clip 330 is closed, the middle portion of the leg 331 does not touch the leg 332 though the plate-like end portions 334 and 335 contact each other. The clip 330 of FIG. 76 is identical to the clip shown in FIG. 72 (i.e., the twenty-fifth embodiment) in function and advantage. Body tissues or organs clamped by the clip 330 are not thermally affected only if the end portions 334 and 335 are thin or only if the middle portions of the legs 331 and 332 do not contact.

Figure 77:
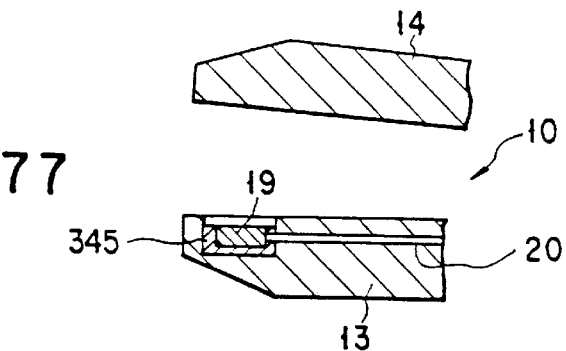
FIG. 77 is a sectional view showing the jaws of a clip applicator according to a twenty-seventh embodiment of the present invention.

FIG. 77 shows a clip applicator 10 according to a twenty-seventh embodiment of this invention, which is a modification of the first embodiment (FIG. 1). The applicator 10 is characterized in that the electric heater 19 attached to the first clip-holding member 13 is wrapped by a heat-insulating member 345. The heat-insulating member 345 can be made of various materials such as ceramic, gas- or liquid-sealed material, or heat-resistant resin (e.g., fluorine resin). It is only the pin 4 of the clip that contacts the electric heater 19. Therefore, the heat the heater 19 generates is not transmitted to any other component of the clip, and the heat is applied concentratedly to the pin 4.

Another clip applicator, which is a twenty-eighth embodiment of the invention, will be described with reference to FIGS. 78 and 79.

Figure 78:
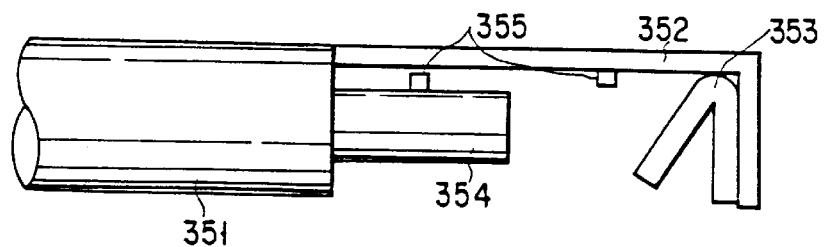
FIGS. 78 and 79 are perspective views illustrating a clip applicator according to a twenty-eighth embodiment of the invention.
Figure 79:
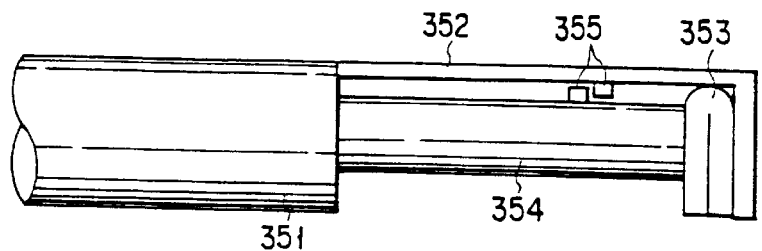

As can be understood from FIGS. 78 and 79, the applicator comprises a sheath 351, a clip holder 352 extending through the sheath 351 and protruding from the distal end thereof, and a rod-shaped oscillation-transmitting member 354 extending through the sheath 351 and protruding there of. The clip holder 352 has an tip which is L-shaped to hold a clip 353. The member 354 is connected at its proximal end to an ultrasonic oscillator (not shown) which is housed in the proximal end of the applicator. The member 354 can be moved back and forth, for transmitting ultrasonic oscillation generated by the oscillator to the clip 353 held at the tip of the holder 352. When pushed forward, the oscillation-transmitting member 354 can press the clip 353 firmly onto the tip of the clip holder 352 and can apply ultrasonic oscillation to the clip 352.

Two stoppers 335 protrude from the clip holder 352 and the oscillation-transmitting member 354, respectively. The stopper 335 on the member 354 abuts on the stopper 335 on the clip holder 352, upon moving toward the tip of the holder 352 for a predetermined distance, preventing any further forward motion of the member 354.

The clip applicator applies the clip 353 in the following way. First, the distal end of the applicator is inserted into a body cavity, with the clip 353 held at the tip of the clip holder 352. The distal end of the applicator is moved in the body cavity, thereby placing a tubular organ (not shown) such as a blood vessel in the gap between the legs of the open clip 353. Then, the oscillation-transmitting member 354 is pushed forward, closing the clip 353, which clamps the tubular organ. The ultrasonic oscillator is driven, generating ultrasonic oscillation. The member 354 transmits the oscillation to the clip 353, whereby the legs of the clip 353 are fused to each other at their contacting surfaces, ligating the tubular organ.

When the stopper 355 on the member 354 abuts on the stopper 355 on the clip holder 352, the member 354 can no longer move forward and ceases to contact the clip 353. Hence, the ultrasonic oscillation is no longer applied to the clip 353, and the legs of the clip 353 are not fused further. The tubular organ is, therefore, clipped steadfastly.

Figure 80A:
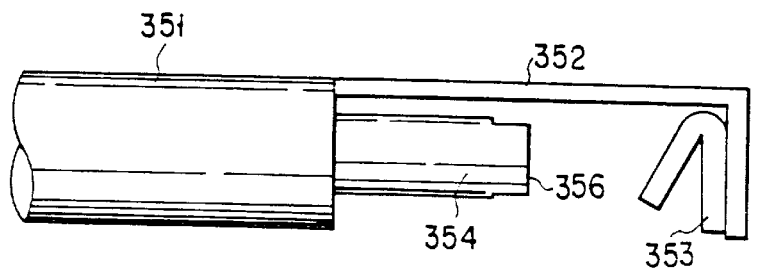
FIG. 80A is a perspective view showing the distal end portion of a clip applicator according to a twenty-ninth embodiment of this invention.
Figure 80B:
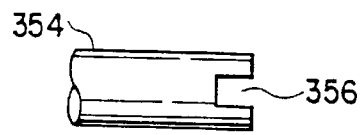
FIG. 80B is a plan view showing the distal end portion of the oscillation-transmitting member of the applicator shown in FIG. 80A.
Figure 81:
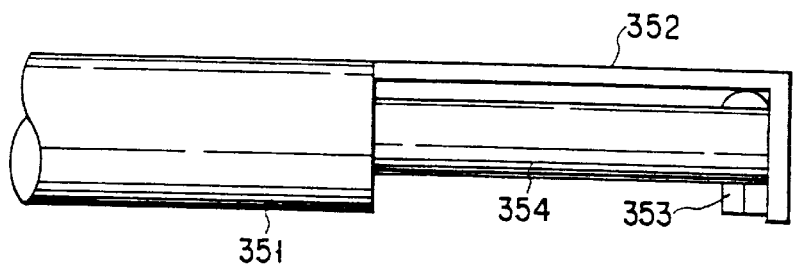
FIG. 81 is a side view showing the distal end portion of the clip applicator shown in FIG. 80A.
Figure 82:
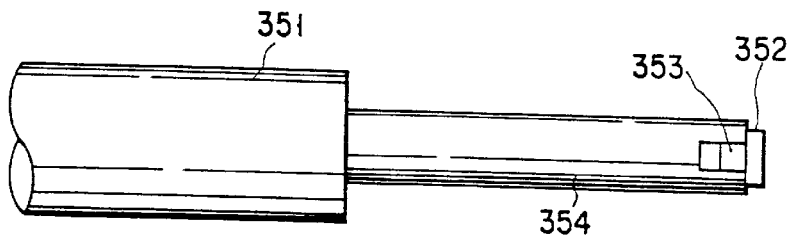
FIG. 82 is a plan view illustrating the distal end portion of the clip applicator shown in FIG. 80A.

A clip applicator according to a twenty-ninth embodiment of the invention will be described, with reference to FIGS. 80A, 80B, 81, and 82. The applicator differs from the twenty-eighth embodiment (FIGS. 78 and 79) in two respects. First, neither the clip holder 352 nor the oscillation-transmitting member 354 has a stopper. Second, the member 354 has a groove 356 cut in its distal-end face, as is illustrated in FIGS. 80A and 80B. The groove 356 serves the purpose of holding the clip 353 steadily.

The clip applicator is used in the following way, in order to ligate a tubular organ (e.g., a blood vessel). One of the legs of the clip 353 is fitted in the groove 356 cut in the distal-end face of the oscillation-transmitting member 354. This done, the distal end of the applicator is inserted into a body cavity and moved therein, thereby placing the tubular organ between the legs of the clip 353. Thereafter, the member 354 is thrust toward the tip of the clip holder 352, thereby collapsing or closing the clip 353. The clip 353 clamps the tubular organ such as a blood vessel. In this condition, the ultrasonic oscillator is driven, generating ultrasonic oscillation. The member 354 transmits and applies the oscillator to the clip 353. As a result, heat is generated at those surfaces of the clip legs which are in frictional contact, whereby the legs of the clip 353 fuse to each other. The moment the member 354 abuts on the tip of the clip holder 352, it can no longer apply the ultrasonic oscillation to the clip 353, because the groove 356 is slightly deeper than the thickness of the clip 353 completely closed. Hence, the clip 353 are not fused further. The tubular organ is, therefore, clipped reliably.

Figure 83:
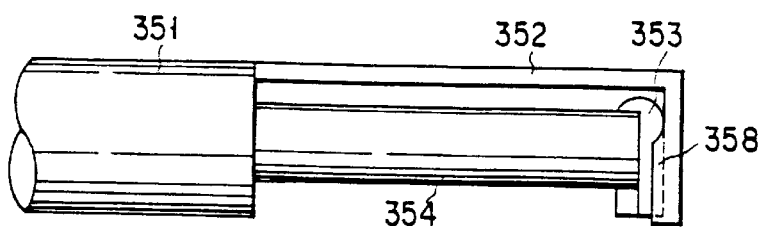
FIGS. 83 and 84 are a side view and plan view of a clip applicator which is a thirtieth embodiment of the present invention.
Figure 84:
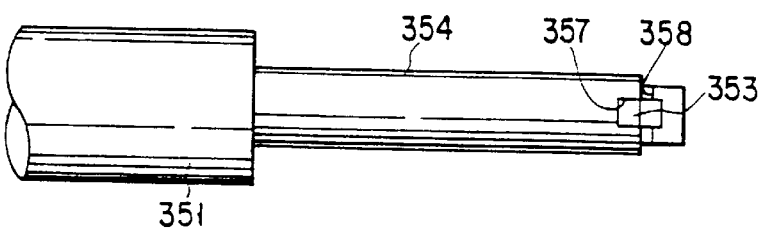

A clip applicator according to a thirtieth embodiment of the invention will be described, with reference to FIGS. 83 and 84. This applicator differs from the twenty-eighth embodiment (FIGS. 78 and 79) in three respects. First, neither the clip holder 352 nor the oscillation-transmitting member 354 has a stopper. Second, the member 354 has a groove 357 cut in its distal-end face, for receiving the clip 353 held at the tip of the clip holder 352. Third, the tip of the clip holder 352 has a groove 358 for receiving the clip 353.

Figure 85:
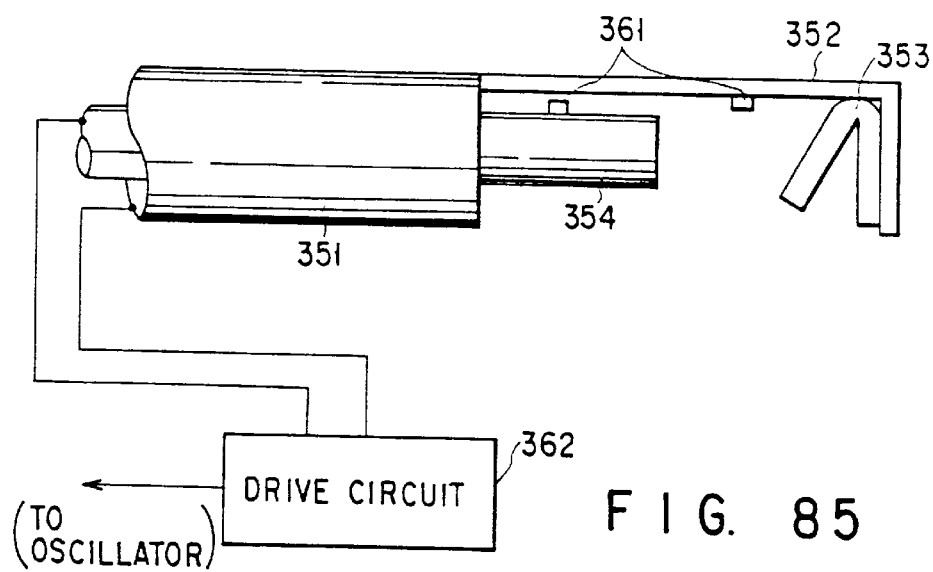
FIG. 85 is a schematic representation of a clip applicator according to a thirty-first embodiment of the present invention.

A clip applicator, which is a thirty-first embodiment of the invention, will be described with reference to FIG. 85. The clip applicator is identical to the twenty-eighth embodiment (FIGS. 78 and 79), except that the stopper on the clip holder 352 and the stopper on the oscillation-transmitting member 354 are used as switch contacts 361 for driving a drive circuit 362 which is connected to an ultrasonic oscillator (not shown). The clip applicator is manipulated in the same way as the clip applicator shown in FIGS. 78 and 79, placing a tubular organ such as a blood vessel in the gap between the legs of the clip 353. Then, the member 354 is moved forward, closing the clip 353 held at the tip of the clip holder 352. The clip 353 thereby clamps the tubular organ. Thereafter, the ultrasonic oscillator is turned on, generating ultrasonic oscillation. The member 354 applies the oscillation to the clip 353. As a result, heat is generated at those surfaces of the clip legs which are in frictional contact, and the legs of the clip 353 fuse to each other. Then, the switch contact 361 on the the member 354 abuts on the switch contact 361 on the clip holder 352, whereupon the drive circuit 362 stops supplying drive signals to the ultrasonic oscillator. Subsequently, the oscillator cease to generate ultrasonic oscillation. Hence, the clip 353 are not fused further. The tubular organ, e.g., a blood vessel, is therefore clipped reliably.

Figure 86:
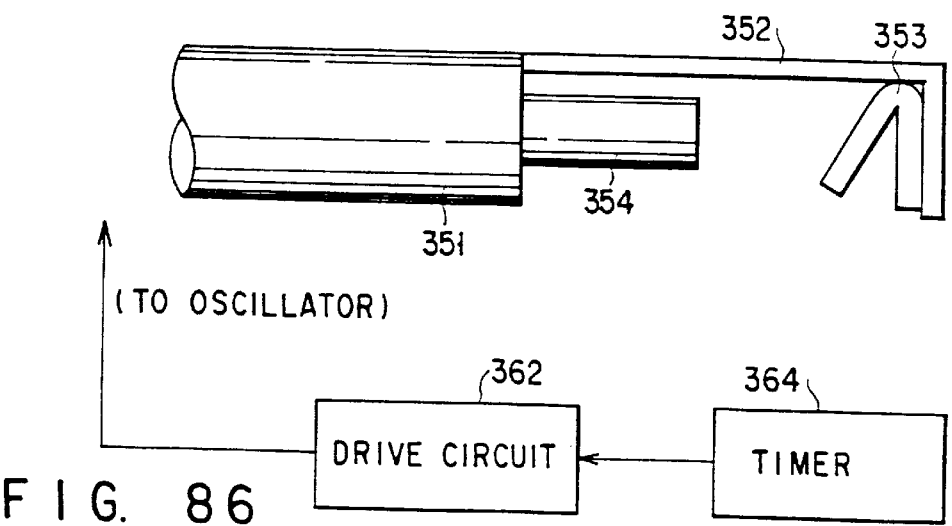
FIG. 86 is a diagram schematically showing a clip applicator which is a thirty-second embodiment of this invention.

A clip applicator, which is a thirty-second embodiment of the invention, will be described with reference to FIG. 86. This clip applicator is a modification of the thirty-first embodiment (FIG. 85), and is different in that a timer 364 is used in place of the switch contacts 361. The timer 364 is connected to a drive circuit 362 for driving an ultrasonic oscillator (not shown). The time the legs of the clip 353 require to fuse completely to each other, while being oscillated is set in the timer 364. Hence, upon lapse of this period, or the moment the legs of the clip 353 are completely fused together, the timer 364 supplies a stop signal to the drive circuit 362. In response to the stop signal the drive circuit 362 stops supplying drive signals to the ultrasonic oscillator, which ceases to generate ultrasonic oscillation. Hence, the fusion of the legs of the clip 353 automatically is terminated. Thus, the clip 353 can firmly clamp a tubular organ such as a blood vessel.

Figure 87:
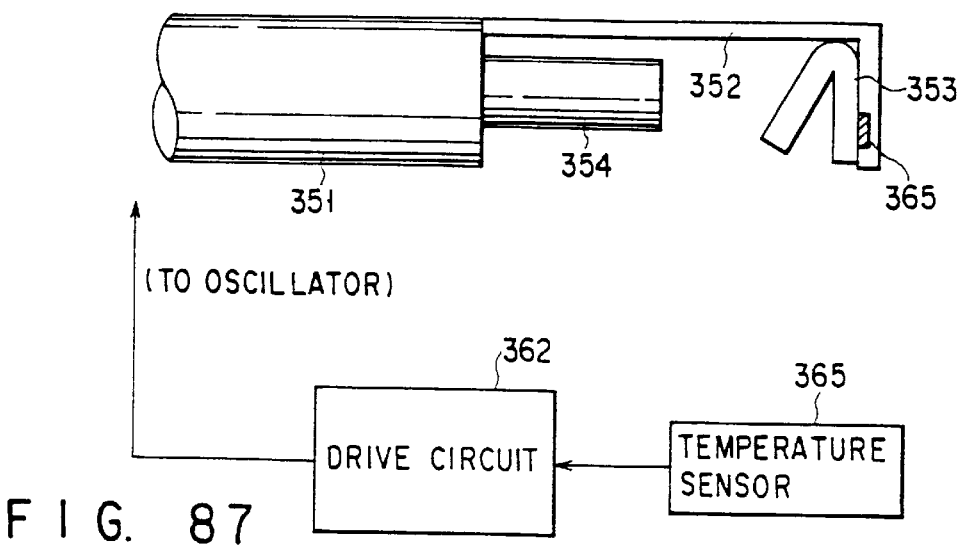
FIG. 87 is a diagram schematically illustrating a clip applicator according to a thirty-third embodiment of this invention.

A clip applicator, which is a thirty-third embodiment of this invention, will be described with reference to FIG. 87. This clip applicator is a modification of the thirty-second embodiment (FIG. 86), and is characterized in that a temperature sensor 365 is used in place of the timer 364. The sensor 365 is connected to a drive circuit 362 for driving an ultrasonic oscillator (not shown). The temperature sensor 365 is embedded in the clip-holding side of the tip of the clip holder 352, so as to detect the temperature of the clip 353 held at the tip. Upon detecting that the temperature of the clip 353 has reached a predetermined value, indicating that the legs of the clip 353 have just fused together, the sensor 365 outputs a signal to the drive circuit 362. In response to this signal the circuit 362 stops supplying drive signals to the ultrasonic oscillator, which ceases to generate ultrasonic oscillation. Hence, the legs of the clip 353 will not fuse excessively.

A clip 370, which is a thirty-fourth embodiment of the present invention, will be described with reference to FIGS. 88A and 88B and FIGS. 89A and 89B.

Figures 88A, 88B:
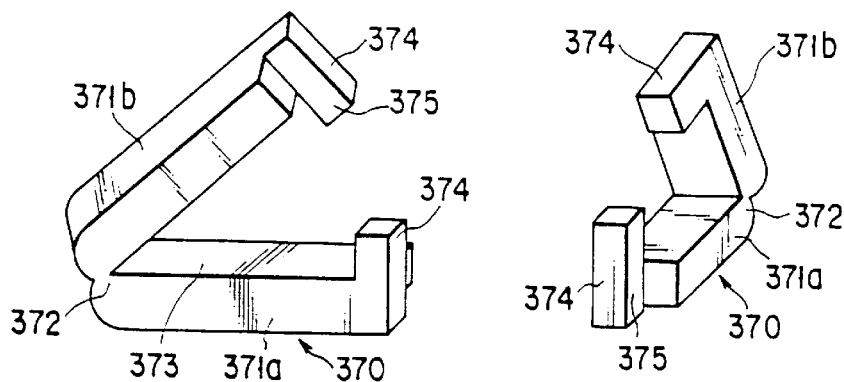
FIGS. 88A and 88B are perspective views, both showing a clip in open state, which is a thirty-fourth embodiment of this invention.

The clip 370 is a one-piece member made of thermoplastic resin. As shown in FIGS. 88A and 88B, the clip 370 comprises a pair of legs 371a 371b and a hinge 372 connecting the legs 371a and 371b together. Each leg consists of a tissue-holding portion 373 and a fusing portion 374. The fusing portion 374 has a fusing surface 375. As can be understood from FIGS. 89A and 98B, the fusing surfaces 374 of the legs 371a and 371b will contact when the clip 370 is closed as the legs 371a and 371b are rotated in a plane parallel to their fusing surfaces 374.

Figures 89A, 89B:
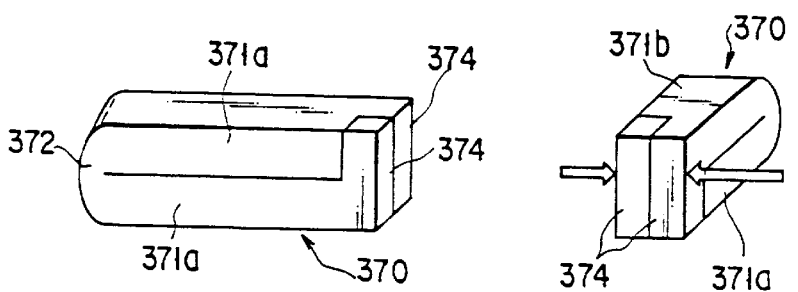
FIGS. 89A and 89B are perspective views, both showing the clip (FIGS. 88A and 88B) in closed state.

The clip 370 is applied in the following way. A tubular organ such as a blood vessel is positioned between the legs 371a and 371b, and the clip 370 is closed as shown in FIG. 89A. An clip applicator (not shown) is manipulated, applying forces to the closed clip 370 in the directions of arrows as illustrated in FIG. 89B, while the fusing portions 374 are being heated by means of a heater or ultrasonic oscillation. As a result, the portions 374 are fused together at their fusing surfaces 375.

The organ clamped between the legs 271a and 271b may have elasticity great enough to apply forces to push the clip 270 open and, hence, to apply shearing force at the fusing surfaces 375 of the fusing portions 374. Nonetheless, the mutual fusion of the portions 374 is so strong that the clip 370 remains closed, clamping the tubular organ firmly and steadily.

FIGS. 90 and 91 shows a clip which is a thirty-fifth embodiment of this invention. This clip is also a one-piece clip made of thermoplastic resin. As shown in FIG. 90, the clip comprises a pair of legs 376a 376b and a hinge 377 coupling the legs 376a and 376b together. The leg 376b has a wedge-shaped projection 378 protruding from the inner surface of its free-end portion. The other leg 376b has a recess 379 formed in the inner surface of its free-end portion. The projection 378 and the recess 379 serve as means for preventing the legs 376a and 376b from moving relative to each other.

When the clip is closed as is illustrated in FIG. 91, the projection 378 of the leg 376b is fitted into the recess 379 of the leg 376a. The sides of the projection 378 contact the sides of the recess 379. These sides are substantially parallel to the plane in which the legs 376a and 376b are rotated. The organ (not shown) clamped between the legs 276a and 276b may have elasticity great enough to apply forces to push the clip open and, hence, to apply shearing force at the contacting sides of the projection 378 and the recess 379. Nonetheless, the projection 378 remains fitted in the recess 379 since the projection 378, which is wedged-shaped, has tightly fitted into the recess 379 having a cross section complementary to that of the projection 378.

After the clip has been closed, the distal end portions of the legs 376a and 376b are pinched together by applying forces in the directions of arrows, as illustrated in FIG. 91, while the free-end portions of the legs 376a and 376b are being heated, by means of a heater or ultrasonic oscillation, at the contacting sides of the projection 378 and the recess 379. As a result, the free-portions 374 are fused together, clamping a tubular organ (not shown) such as a blood vessel steadfastly.

FIGS. 92 and 93 shows a clip 380 which is a thirty-sixth embodiment of this invention. The clip 380 is a one-piece clip made of thermoplastic resin. As shown in FIG. 92, the clip 380 comprises a pair of legs 381a 381b and a hinge 382 coupling the legs 381a and 381b together. The leg 381b has a fusing tongue 383 extending downwards from its free end. The tongue 383 contacts the end face of the leg 381a when the clip 380 is closed, as is illustrated in FIG. 93. The connecting surfaces of the tongue 383 and the leg 381a is perpendicular to the plane in which the legs 381a and 381b are rotated.

The clip 380 is applied as follows to clamping a tubular organ such as a blood vessel. First, the clip 380 in its open state is moved such that the organ is placed in the gap between the legs 381a and 381b. This done, the clip 380 is closed, and the free-end portions of the legs 381a and 381b are heated by means of a heater or ultrasonic oscillation and thereby fused together at the contacting surface of the tongue 383 and the free end of the leg 381a. The organ (not shown) clamped between the legs 276a and 276b may have elasticity great enough to apply forces to push the clip 380 open and, hence, to apply shearing force at the contacting surfaces of the tongue 383 and the free end of the leg 381a. In spite of the shearing force, the tongue 383 remains fused to the end face of the leg is 381a. As a result, the clip 380 keeps clamping the tubular organ between its legs 381a and 381b.

A clip applicator 405, which is a thirty-seventh embodiment of the invention, will be described with reference to FIGS. 94 to 96.

FIG. 94 shows a clip 401 which the applicator 405 (FIG. 95) is to apply. The clip 401 comprises a pair of legs 403 and a hinge 402 connecting the legs 403. Each leg 403 has a projection 404 protruding from its outer surface. Either the hinge 402 or the entire clip 401 may be heated to be permanently deformed to clamp body tissues between the legs 403.

The clip 401 is made of a polymer or copolymer of dioxanone, lactide or glycolide. Of the polymer, 5 to 50% by weight is monomer having a relatively low molecular weight of 10,000 or less. Hence, the polymer has a thermal-deforming point of 100° C., more preferably 45 to 80° C.

As shown in FIG. 95, the clip applicator 405 comprises an insertion section 406 which is a thin pipe. A pair of clip-holding members 408 and 409 are rotatably connected at one end by a hinge 407, thus constituting a clip holder. The first clip-holding member 408 is fastened to the distal end of the insertion section 406. Each clip-holding member has a groove 410 in its inner surface. The grooves 410 of the members 408 and 409 are positioned to face each other. The grooves 410 will receive the projections 404 of the clip 402 when the member 409 is rotated into its closed position, with the clip 401 held between it and the member 408.

A pin 411 protrudes sideways from the distal end portion of the clip-holding member 409. A connector 412 is rotatably connected at one end to the pin 411. The other end of the connector 412 is fastened to the distal end of an operating rod 413, which extends through the insertion section 406. The rod 413 protrudes from the proximal end of the section 406. Fixed to the proximal end of the insertion section 406 is an operating handle 417. The handle 417 comprises a handle 414 fixed to the proximal end of the insertion section 406, a handle 416 rotatably connected to the fixed handle 414 by a pin 415. The upper end of the notable handle 416 is connected to the proximal end of the operating rod 413. Hence, when the handle 416 is moved toward and away from the fixed handle 414, the rod 413 is pulled backward and forward, opening and closing the clip holder constituted by the members 408 and 409.

The insertion section 406 has a fluid passage 418. The passage 418 extends between the distal opening 419 of the insertion section 406 and a connecting tube 420 protruding from the proximal end portion of the section 406. A syringe 421 is removably coupled to the connecting tube 420.

The clip applicator 405 is manipulated as follows to apply the clip 410 in order to ligate a tubular organ such as a blood vessel and a bile duct.

First, the rotatable handle 416 is moved, thereby rotating the clip-holding member 409 into the open position as shown in FIG. 96. The clip 401 is put into the gap between the clip-holding members 408 and 409. Once the projections 404 of both clip legs 403 enter the grooves 410 of the members 408 and 409, the clip 401 can hardly slip out of the nip between the clip-holding members 408 and 409.

Then, the insertion section 406 is inserted into the body cavity where a tubular organ 422 to ligate is located. The section 406 is further moved, thereby catching the organ 422 between the legs 403 of the clip 401. Next, the rotatable handle 417 is squeezed, pushing the operating rod 413 forward. The clip-holding member 409 is thereby rotated into the closed position, closing the clip 401 and, hence, collapsing the tubular organ 422.

In this condition, the piston of the syringe 421 connected to the fluid passage 418 is pushed, pumping a heated fluid to the distal opening 419 of the insertion section 406 through the fluid passage 418. The heated fluid is hence applied onto the clip 401. The fluid is hot enough to deform the clip 401 thermally. Heated with the fluid, the clip 401 softens such that the legs 403 wraps the tubular organ 422 as is shown in FIG. 97. Thereafter, the piston of the syringe 421 is pushed, this time, pumping cold water to the distal opening 419 of the insertion section 406 through the fluid passage 418 and subsequently applying the cold water onto the clip 401. The fluid is hot enough to deform the clip 401 thermally. Cooled with the water, the clip 401 hardens and is permanently deformed, thus clamping the tubular organ 422 steadfastly.

Merely by thermally deformed with the heated fluid, the clip 401 can reliably ligate the tubular organ 422—requiring no mechanical fastening means whatever. Therefore, the clip 401 can be made small and simple. In addition, the clip 401 can be softened at a relatively low temperature, hot water and cold water can sell serve as heating medium and cooling medium, respectively.

A clip applicator 405, which is a thirty-eighth embodiment of the invention, will be described with reference to FIG. 98. The clip applicator 405 is identical to the thirty-seventh embodiment (FIG. 95), except in that heater 424 such as a diode or a ceramic heater is set in a recess 423 made in the inner surface of the clip-holding member 405. The heater 424 is electrically connected by to a power supply (not shown) provided outside the applicator 405 by a lead wire 425 which extends through the insertion section 406 and out of the proximal end of the section 406.

After the clip-holding member 409 is rotated into its closed position, thus closing the clip 401 and ultimately collapsing the tubular organ 422 held between the members 408 and 408 of the clip 401, an electric current is supplied from the power supply via the lead wire 425 to the heater 424. The heater 424 generates heat, which thermally deforms the clip 401. Then, both legs 403 of the clip 401 are cooled and permanently deformed, firmly clamping the organ 422 between them.

The clip heating/cooling means is not limited to those employed in the thirty-seventh embodiment (FIG. 95) and the thirty-eighth embodiment (FIG. 98). Instead, a laser beam or hot air may be utilized as clip-heating medium, and any coolant other than cold water (e.g., coolant gas) may be used as clip-cooling medium.

A staple 431, which is a thirty-ninth embodiment of this invention will, will be described with reference to FIGS. 99 and 100. As is shown in FIG. 99, the staple 431 (used as a suture) is a strip having two clawed ends 432, each extending downwards from one end. The staple 431 has two grooved portions 433 having a groove made in its upper surface, at a ⅓-length distance from the ends, respectively.

The staple 431 is made, as a whole, of polymer or copolymer of dioxanone, lactide or glycolide. The polymer or copolymer contains 5 to 40% by weight of a platicizer, either fatty acid or ester of fatty acid, and thus has a thermal-deforming point of 45 to 80° C. Various commercial available plasticizers can be used in the polymer or copolymer, but preferable for use in the invention are:

dibutyl sebacate, epoxidated soybean oil, dibutyl stearate, epoxidated safflower oil, esters of oleic acid, and esters of linoleic acid.

The staple 431 is applied in the following way to stitch body tissues together. First, the staple 431 is heated and softened. Then, one clawed end 433 of the staple 431 is forced into the end portion of a tissue 434a, piercing the same, as shown in FIG. 100. Further, the staple 431 is bent at the first grooved portion 433. The staple 431 is then bent at the grooved portion 433, and other clawed 433 of the staple 431 is then forced into the end portion of a tissue 434b, piercing the same. As a result, the staple 431 is deformed as illustrated in FIG. 100. Finally, the staple 431, thus deformed thermally, is cooled and hardened, firmly stitching the body tissues 434a and 434b to each other.

The staple 431 may be heated, deformed, and hardened by means of either a special-purpose stapler or by a general-purpose stapler.

Merely by thermally softened, then deformed, and finally cooled and permanently deformed, the staple 431 can suture body tissues 434a and 434b together, both readily and reliably—requiring no mechanical fastening means whatever. The staple 431 can therefore be made small and simple. Moreover, the staple 431 can be softened at a relatively low temperature, it can be heated and cooled by a comparatively simple method.

FIG. 101 shows a clip 435 which is a fortieth embodiment of the present invention. The clip 435, which is identical in shape to the clip 401 (FIG. 94), is made of polymer or copolymer of dioxanone, lactide or glycolide. The polymer or copolymer contains 5 to 40% by weight of an oily image intensifier such as Urographine (tradename) or Lipodole (trade name), and thereby has a thermal-deforming point of 45 to 80° C.

The clip 435 is applied in the same way as the clip 401 (FIG. 94). The clip 435 achieves the same advantage as the clip 401. It also attain additional advantages. First, since the clip 435 is made of polymer or copolymer containing an image intensifier, its position in an patient can be determined by means of X-ray photography. Second, as the clip 435 is absorbed into a body organ, so is the image intensifier, making it possible to determine how much the clip 435 has been absorbed into the organ merely by tracing the image intensifier in an X-ray photograph of the clipped organ.

FIG. 102 shows a clip 436 which is a forty-first embodiment of the present invention. This clip 426 has the same strength as the clip 435 but is smaller and thinner. Resin which can be absorbed into body tissues is has but a small mechanical strength. A clip or staple made of such resin must inevitably made large and thick to have a sufficient strength. To be adequately strong, the clip 435 is made of polymer or copolymer of dioxanone, lactide or glycolide, which contains powders of one or two ceramics absorbable into body tissues, selected from the group consisting of tricalcium phosphate (TCP), hydroxyapatite (HAP), and tetracalcium phosphate—in total amount of 5 to 45% by weight.

Made of polymer or copolymer containing ceramic powders, the clip 436 can have sufficient strength though it is small and thin. Since the ceramic powder contained in the polymer or copolymer is also absorbable into body tissues, the clip 436 will be absorbed in its entirety into the body tissues to which it has been applied.

FIGS. 103A to 113 show the forty-second embodiment.

Figures 103A, 103B, 103C:
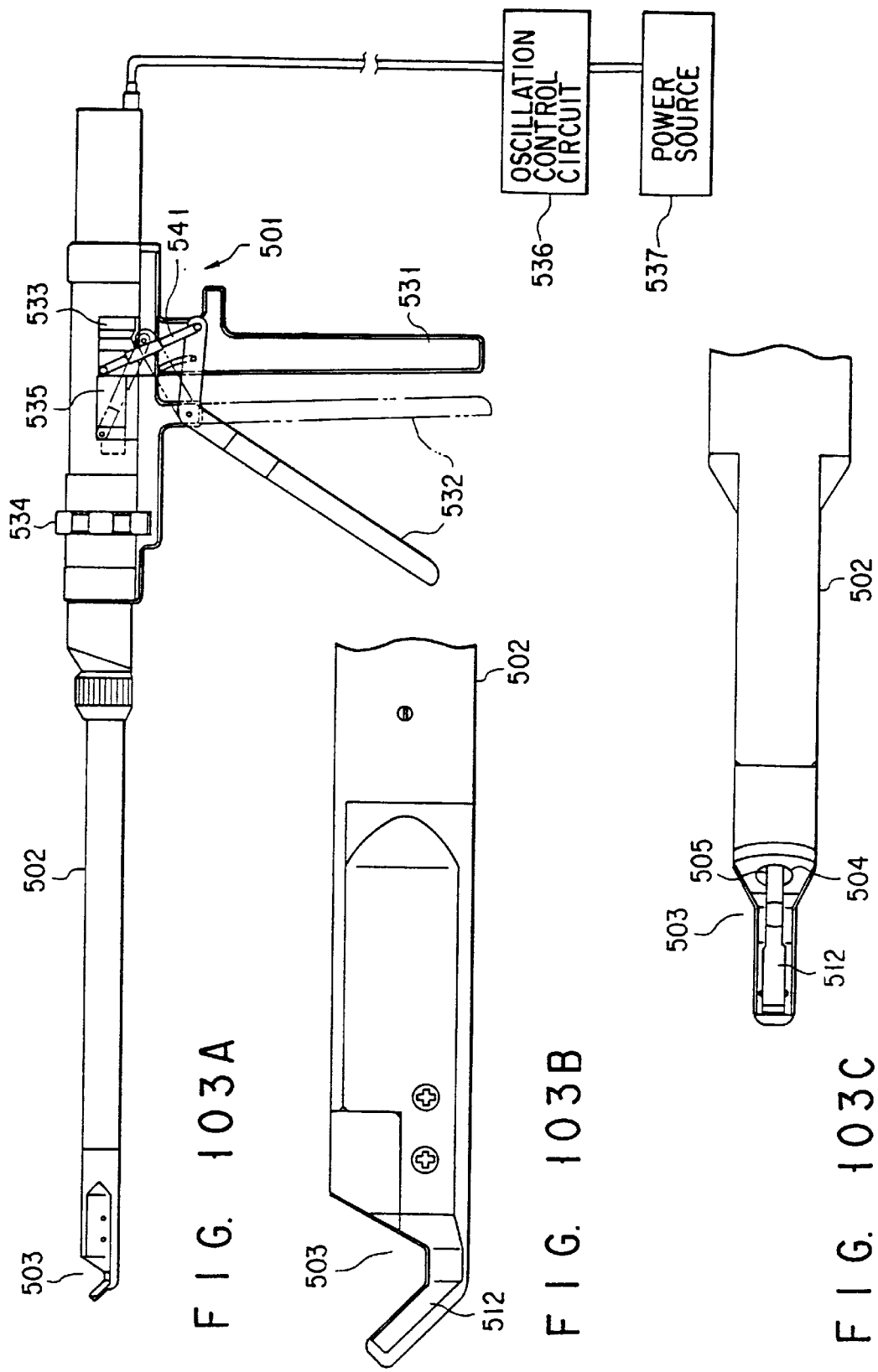
FIG. 103A is a side view showing the entire clip applicator according to a forty-second embodiment of the present invention.
FIG. 103B is a side view showing a distal end portion of the applicator according to the forty-second embodiment.
FIG. 103C is a plan view showing the distal end portion of the applicator according to the forty-second embodiment.

FIG. 103A shows the entire structure of a clip applicator. This applicator comprises a handle portion 501 as an operating portion, and an elongated (or insertion portion 502 connected to the handle portion 501, which is to be inserted into a body cavity. The elongated portion 502 has a circular shape whose diameter should preferably be 12 mm or less.

The distal end portion of the elongated portion 502 is, for example, open upward, and is provided with a distal end opening portion 503 which is substantially V-shaped, viewed from the side thereof (see FIG. 103B). This distal end opening portion 503 constitutes a means for holding the clip 511 as an object to be used.

The elongated portion 502 comprises a tubular member, and a channel 504 is formed along the lengthwise direction of the tubular member in the tubular member. The channel 504 is open in the distal end side, and communicates with the distal end opening portion 503. In the channel 504, a probe 505 as an oscillation transmission member of an ultrasonic oscillation means is provided in the channel 504, so as to be slidable in the lengthwise direction. The probe is inserted in a cylindrical probe cover 506, except for the distal end portion and the base portion of this probe 505. The base end of the probe 505 is connected to an ultrasonic oscillator. The probe 505 is made of a schematically cylindrical member made of metal such as stainless steel, duralmin, $Ti_6Al_{14}V$ or the like. A tip portion 507 of a conical shape is formed on the distal end of the probe 505. An O-ring 508 made of heat curing resin such as silicon or Teflon (which is a commercial name) is inserted between the distal end of the probe 505 and the probe cover 506. A guide member 509 is slidably provided between the probe cover 506 and the channel 504 of the elongated portion 502.

Further, as shown in FIGS. 104A to 106B, a clip container means for containing a plurality of clips 511 disposed in line is provided below the position where the probe 505 is provided, in the channel 504. This clip container means is formed of a clip holder groove 512. A plurality of clips 511 disposed in line are contained in the clip holder groove 512. Normally, the clips are contained, disposed in line in a cartridge 520. The clips 511 in the cartridge 520 are fed out through the clip holder groove 512, one after another from the first one at the distal end side. The passage portion in front of the clip holder groove 512 reaches the distal end opening portion 503, and is formed to be continuous to the distal end opening portion 503. The clip holder groove 512 functions as a guide passage for guiding the clips 511 to the distal end opening portion 503 from inside the cartridge 520.

As shown in FIG. 105, the clip holder groove 512 is provided with a push tool 513 for pushing the clips 511 to the distal end opening portion 503. The push tool 513 has a pair of push edges 514 positioned below the position of the probe 505 and arranged in the left and right sides thereof, above the clip holder groove 512. Each of these left and right paired push edges 514 is made of a stopper plate spring of metal plate material such as stainless or the like, and a clip 511 fed out onto and set in the clip holder groove 512 from the cartridge 520 is clamped between the pair of push edges 514. Notches 514a for stopping a projection 511d of the clip 511 are respectively formed in the distal ends of the push edges 514.

The structure of the clip 511 will now be explained with reference to FIGS. 110A and 110B. The clip 511 is shaped in a form like a prismatic rod and is made of organism adaptive resin such as organism absorptive resin, nylon, or the like. The shape of the clip 511 will be specifically explained as follows. The clip 511 has a hinge portion 511a including a thin portion, and the hinge portion 511a connects a pair of legs 511b. The notched amount of the upper side of the hinge portion 511a is smaller than that of the lower side thereof. Thus, the clip 511 is arranged to be easily bent on the upper side, i.e., on the side facing the probe 505. Therefore, as shown in FIG. 110B, the notch in the upper side of the clip 511 should preferably be U-shaped, while the notch in the lower side should preferably be substantially M-shaped with smoothness to be continuous to the lower surfaces of both distal end portions 511b. One side surface of the notch of the lower side extends at an angle of 45° or less, e.g., at 30° with respect to the upper surface of the clip 511, while the other side surface of this lower notch should preferably extend at 80° or more with respect to the upper surface of the clip 511. The projection 511d and the side surface extending at 80° should preferably be positioned in the distal end side. In this embodiment, the hinge portion 511a of the clip 511 is elongated in the lengthwise direction and is made of resin of which high polymer is oriented, in order that the bending resistance is improved. Projections 511d are respectively provided on the left and right sides close to the hinge portion 511a. These projections 511d are arranged to be engaged with the notch grooves 514a provided in the distal ends of the push edges 514. In addition, a concave portion 511x is provided in the upper surfaces of one of both leg 511b, while a convex portion 511y to be engaged into the concave portion 511x is provided in the upper surface of the other of both legs 511b. The concave portion 511x and convex portion 511y constitute a clip fixing means for fixing the legs 511b.

The clip holder groove 512 forms the distal end opening portion 503 and a slanting surface portion 512a starting from the distal end opening portion 503. A projection 516 which collides into the clip 511 is provided at the distal end of the slanting surface portion 512a. The slanting surface portion 512a changes the orientation of the clip 511 by its inclination, thus constituting a force conversion means. This force conversion means converts the feed force applied to the clip 511 into a closing force. That portion in the area of the distal end of the clip holder groove 512 which forms the slanting surface portion 512a is wider than the other portion of the clip holder groove 512 so that clips 511 can easily pass through. In this case, the angle of the slanting surface portion 512a should preferably be 30° to 60° with respect to the elongated portion 502.

A cartridge 520 is attached to a portion in a relatively rear side of the clip holder groove 512. A plurality of clips 511 are disposed in line in the longitudinal direction inside the cartridge 520, and these clips 511 are elastically energized from the back side through a plunger 521 by an elastic means such as a coil spring 522 or by another pressure means.

A first stopper plate spring 523 provided in an upper position of the clip holder groove 512 is provided at a position in front of the distal end of the cartridge 520, and a second stopper plate spring 524 is provided at a lower portion of the clip holder groove 512. The plate springs 523 and 524 temporarily stop a clip 511 fed out of the cartridge 520, thereby preventing the clip 511 from moving forward. The stopper springs 523 and 524 are provided with their base portions fixedly positioned. For example, the base portion of the stopper plate spring 523 is fixed to a cover member 520a of the cartridge 520. The base portion of the second stopper plate spring 524 is fixed to a member of the elongated portion 502. Naturally, the base portion of the first stopper plate spring 523 may otherwise be installed on a member of the elongated portion 502, and the base portion of the second stopper plate spring 524 may also otherwise be installed on a member of the cartridge 520.

The distal end portions of the stopper plate springs 523 and 524 are both bent toward the center of the clip holder groove 512 and used as stopper nail portions 523a and 524a, respectively, such that the stopper nail portions 523a and 524a are partially projected into the clip holder groove 512. In addition, the positions of the stopper nail portions 523a and 524a of the stopper plate springs 523 and 524 are shifted in the longitudinal direction relative to each other with an interval equivalent to one clip 511 interposed therebetween. The stopper nail portion of the first stopper plate spring 523 presses the distal end of a clip 511 fed out from the distal end of the cartridge 520, while the stopper nail portion 524a of the second stopper plate spring 524 presses another clip 511 to be fed out next, at the distal end of the cartridge 520.

As shown in FIG. 105, a flange portion 525 is provided at a middle portion of the member in the base portion of the push tool 513. When the push tool 513 is moved forward, the flange portion 525 is brought into contact with the second stopper plate spring 524 positioned in the upper side, thereby pushing upward the stopper plate spring 524 to be released from the clip holder groove 512.

Figure 107:
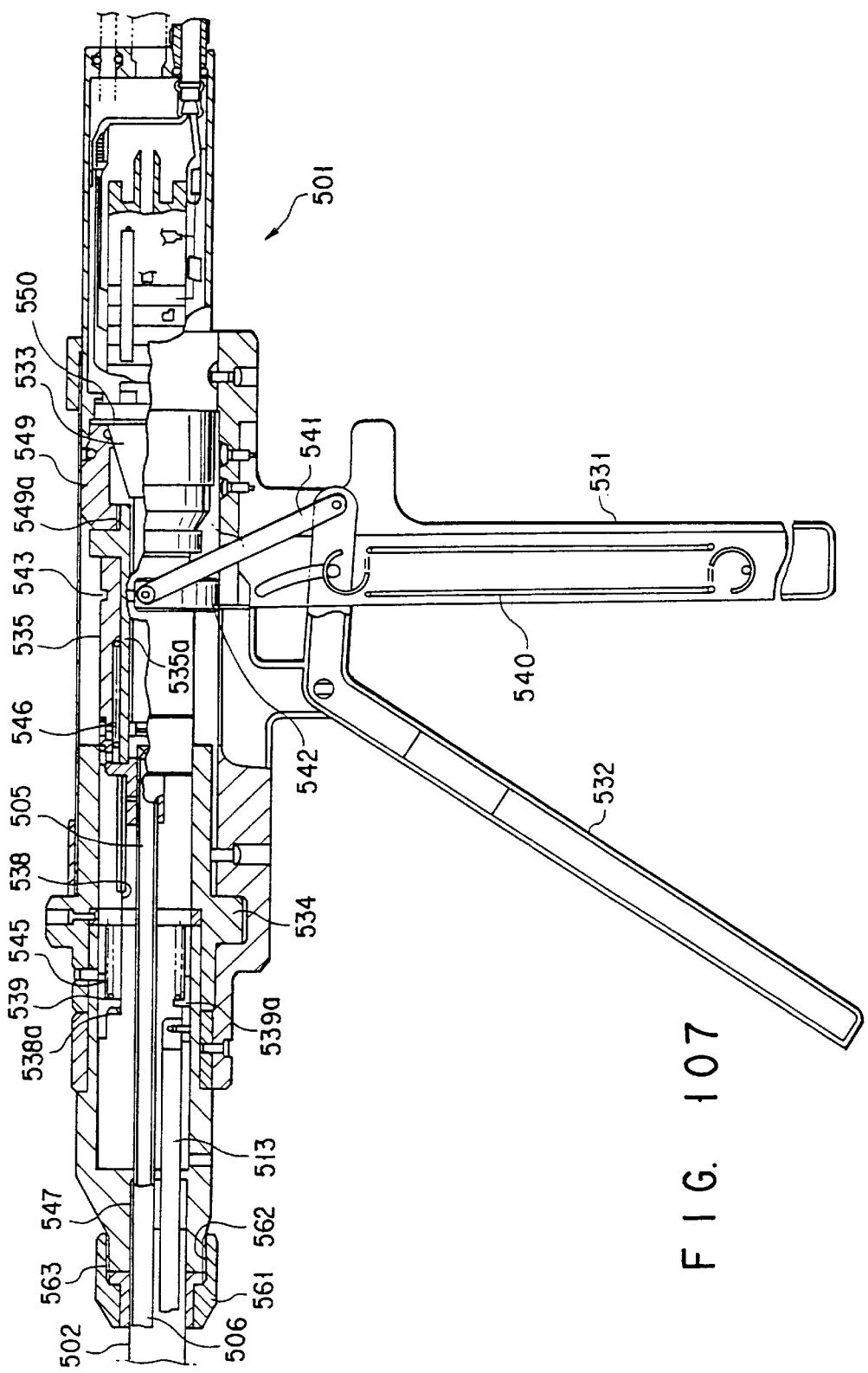
FIG. 107 is a longitudinal cross-sectional view showing a handle portion according to the forty-second embodiment.
Figure 108A:
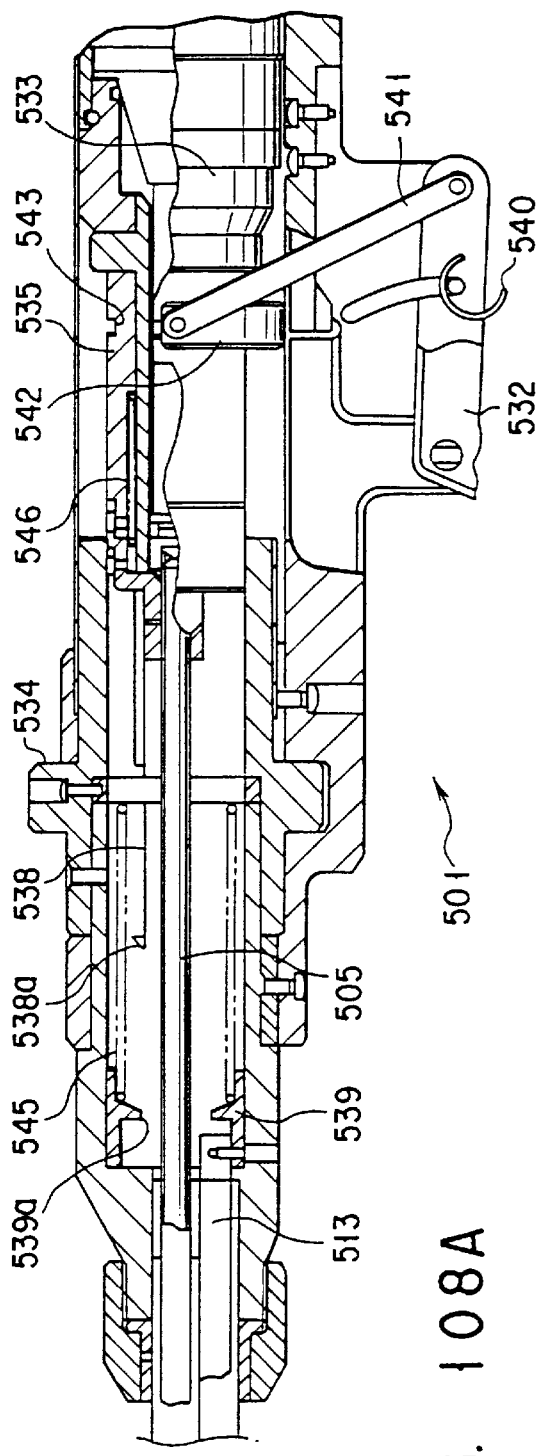
FIG. 108A is a longitudinal cross-sectional side view showing an initial state of the handle portion according to the forty-second embodiment.
Figure 108B:
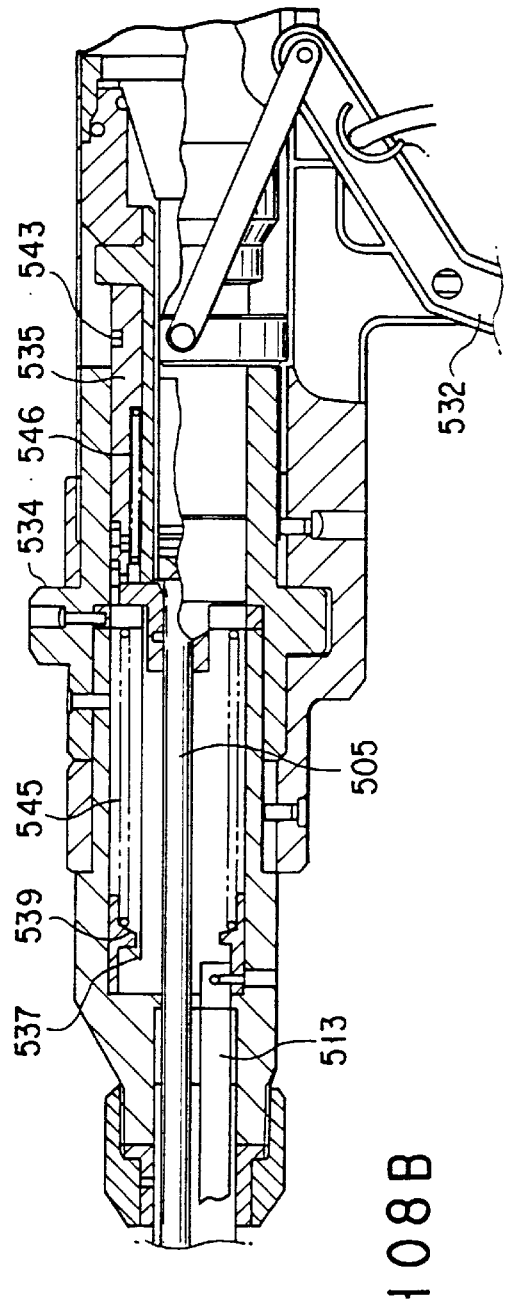
FIG. 108B is a longitudinal cross-sectional side view showing a clipping state of the handle portion according to the forty-second embodiment.

A means for operating the push tool 513 and the probe 505 is provided on the handle portion 501. AS shown in FIG. 107 and FIGS. 108A and 108B, the handle portion 501 is provided with a clamp portion 531, an operation lever 532 which can freely be opened and closed, a slidable ultrasonic oscillator 533, a rotation knob 534 for rotating the elongated portion 502, and a cylindrical member 535 for sliding the push tool 513 and the probe 505. The ultrasonic oscillator 533 is connected to an ultrasonic drive circuit 536 including an oscillation control circuit and a drive power source 537, as shown in FIG. 103A.

The operation lever 532 is pivoted on the base member of the handle portion 501, and is elastically energized in the opening direction by a coil spring 540. This operation lever 532 is connected to the drive member 535 through a linking mechanism which will be described later. The linking mechanism comprises a first link 541 as a plate-like member and a second link 542 having a semicircular cross-section. The second link 542 is covered on the outer circumference of the drive member 535. A projecting portion to be slidably engaged in a narrow portion 543 as an inner circumferential groove formed in the outer circumference of the drive member is provided in the inner circumferential portion of the second link 542. The drive member 535 and the second link 542 are in a relationship that the member 535 and the link 542 are rotatable, relative to each other, around the lengthwise axis of the drive member 535.

A plurality of latches 538 are attached to the front end of the drive member 535. The latches 538 can be released aside by the elasticity of themselves, and a stopper nail 538a having a slanting surface is formed on the distal end of each latch 538. The stopper nail 538a can be engaged with a flange 539a formed inside a transmission member 539 connected with the push member 513. The transmission member 539 is made of a ring-like member having an inner circumferential surface on which the flange 539a is formed. Thus, the drive member 535 is connected to the push member 513 through the transmission member 539, with the use of the latches 538.

An elastic member, e.g., a push spring 545 comprising a compression coil spring, is provided between the transmission member 539 and the handle portion 501, and the push spring 545 elastically energizes the transmission member 539 and the push member 513 toward the distal end side. In addition, a coil spring 546 is indirectly provided between the drive member 535 and the probe 505. The coil spring 546 elastically energizes the probe 505, using the drive member 535 as a base.

A hole allowing the probe cover 506 and the push tool 513 to slide is provided at the rear end portion of the elongated portion 502, and this hole is provided with a sealing means 547 made of elastic resin (e.g., silicon rubber) or other resin (e.g., form styrene). The flow of a gas from the elongated portion 502 side into the handle portion 501 is prevented by this sealing means 547 and the O-ring 508 around the probe 505. A gas does not leak even if the elongated portion 502 is inserted into a gas-expanded body cavity, and thus, the gas-expansion pressure does not decrease.

Figure 109:
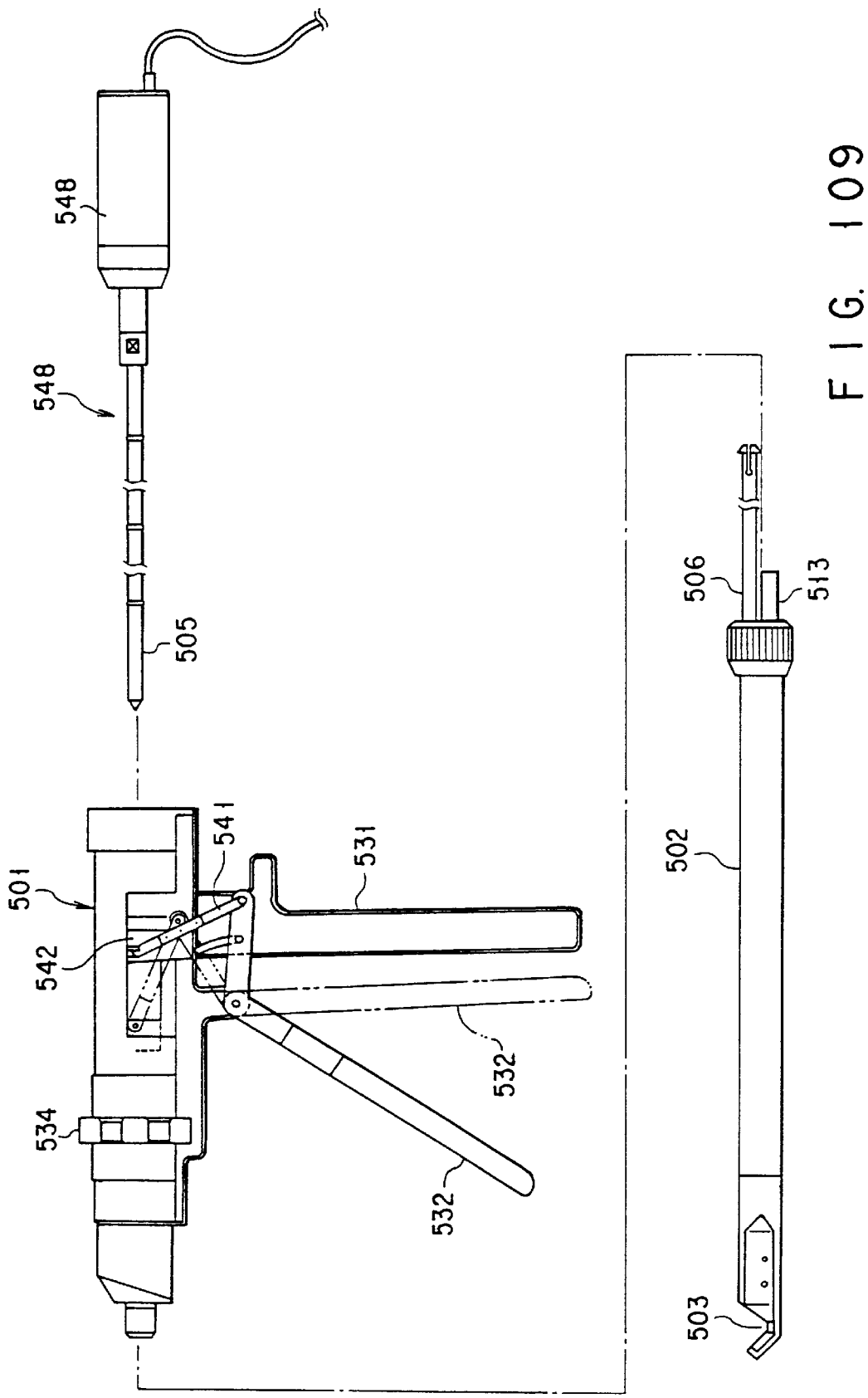
FIG. 109 is a side view showing exploded respective portions of the applicator according to the forty-second embodiment.

Further, as shown in FIG. 109, this embodiment comprises, as its units, a probe unit 548 including a probe 505 and an ultrasonic oscillator 533, a handle is portion 501 including a grip portion 531, an operation lever 532, and a drive member 535, as well as an elongated portion 502 including a push member 513, a cartridge 520, and a probe cover 506. Further, these units are connected by means of connection structures, such as screws, collet chucks, cam pins, and the like, so that the respective units are detachable from each other.

In this embodiment, the probe unit 548 and the handle portion 501 are attached to each other or detached from each other, in such a manner in which a screw portion 549a is provided in the inner circumference of the distal end of a probe housing 549 fixing the ultrasonic oscillator 533 and the probe 505, and the screw portion 549a is screwed on a rear end portion of the cylindrical member 535a integral with the drive member 535. In addition, the inside of the probe housing 549 is completely sealed by means of an O-ring or the like.

At the attachment portion between the handle portion 501 and the elongated portion 502, a detachable knob 561 is provided which is rotatable around the lengthwise axis of the elongated portion 502. To fix the handle portion 501 to the elongated portion 502, a screw portion 562 formed in the rear circumference of the detachable knob 561 is screwed over a screw portion 563 provided in the outer circumference of the distal end of the handle portion 501.

In addition, the push member 513 in the elongated portion 502 is fixed to a transmission member 539 by means of screws, and the probe cover 506 is fixed to the drive member 535 by means of screws. In place of screws, methods of using cam pins, friction fixing, and collet chucks (not shown) can be used to attach these components to the elongated portion 502.

Next, the operation of the clip applicator 513 constructed above will be explained. As shown in FIG. 113, the elongated portion 502 is inserted through a trocar 552 into an abdomen cavity 551 expanded by injecting thereinto carbon dioxide through a stick needle not shown. Thereafter, a tubular organ such as a blood vessel or the like to be clipped is arranged in the distal end opening portion 503 of the elongated portion 502 of the clip applicator, while observing the inside of the abdomen cavity 551 with the use of an endoscope 554 inserted into the abdomen cavity 551 through another trocar 553. (See FIG. 112A.)

When the lever 532 is operated so as to rotate in the direction toward the closing position indicated by a two-dot chain line in FIG. 103, the engagement between the transmission member 539 and the latch 538 is released by a cam means not shown, in the handle portion 501. Then, the transmission member 539 and the push member 513 slide toward the distal end side, due to elastic energization of the push spring 545 (see FIG. 108A).

In this state, the projection 511d of the clip 511 waiting in front of the cartridge 520 is engaged with the notch groove 514a at the distal end of the push edge 514. The clip 511 is pushed by the push member 513, and forcibly moves forward over the stopper plate spring 524 provided in a front position, along a clip holder groove 512, to a position immediately before the slanting surface portion 512a at the distal end thereof (see FIG. 111A).

When the clip 511 further moves forward to bring the front end of the clip 511 in contact with the slanting portion 512a, a force is applied which serves to rotate the clip 511 around the projection 511d as the rotation axis, and a reaction force from the clip holder groove 512 causes the front and rear legs 511b to bend in the upward direction, around the hinge portion 511a. Then, the rear leg 511b is further bent upward by the surface so as to be at an angle of 80°. When the distal end of the clip 511 thus reaches a collision surface of the projection 516, the clip 511 is V-shaped surrounding the distal end opening portion 503 (see FIGS. 111B, 111C, and 111D).

Figure 111A:
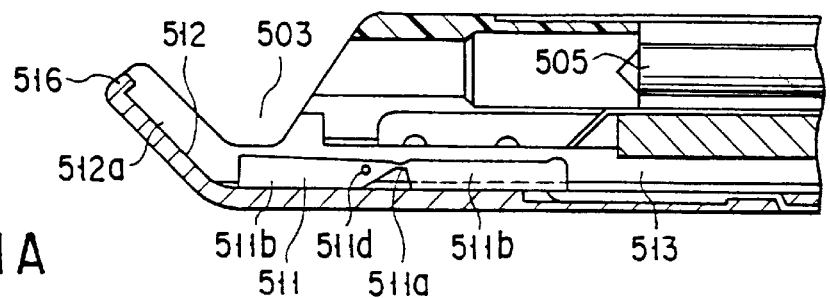
FIG. 111A to FIG. 111E are views explaining use procedures of the applicator according to the forty-second embodiment.
Figure 111B:
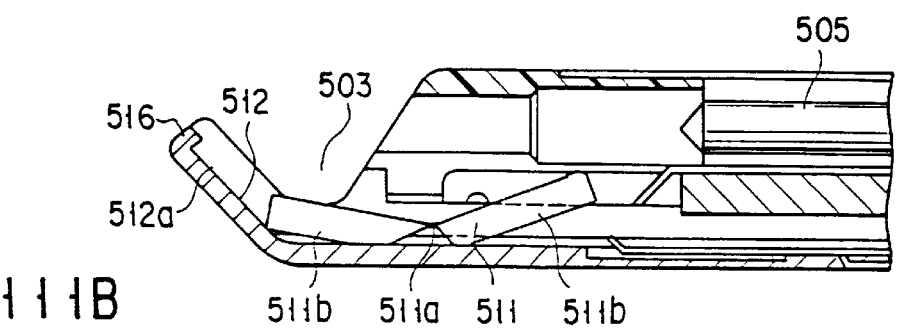
Figure 111C:
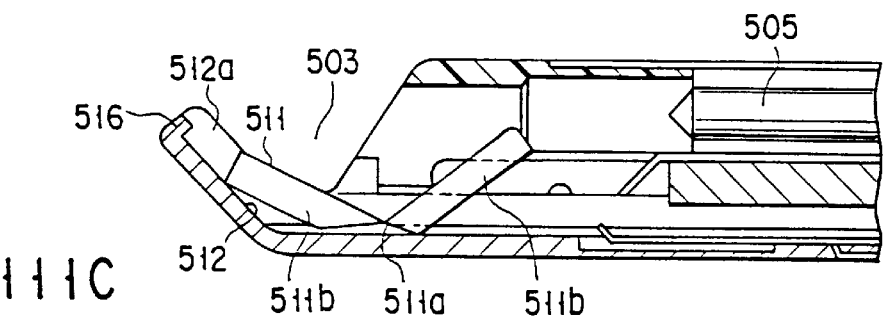
Figure 111D:
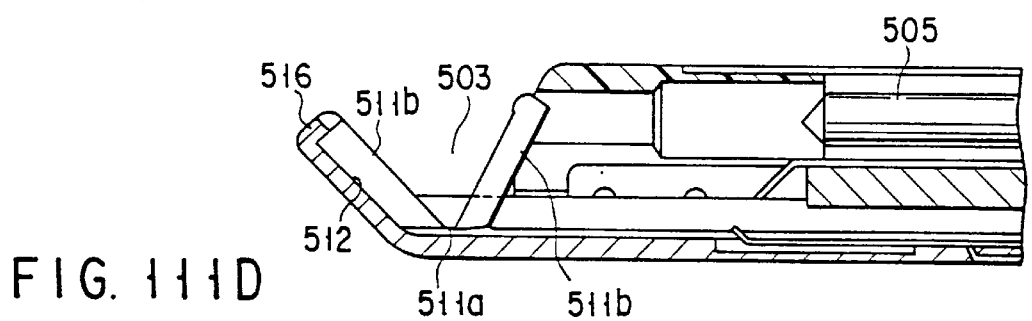
Figure 111E:
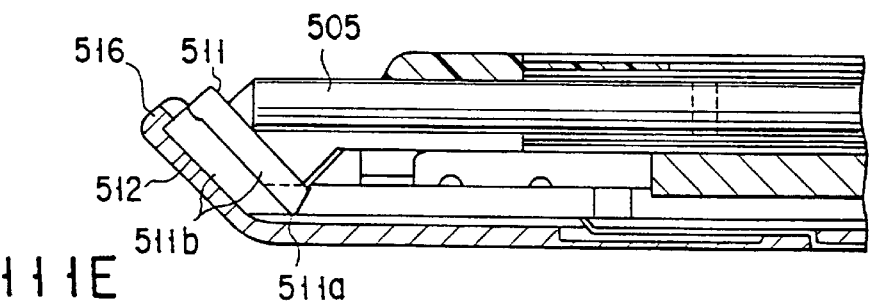

Thereafter, when the lever 532 is closed deeply, the probe 505 further moves to the distal end side, and collides with the end surface portion of the rear leg 511b of the clip 511, which is V-shaped (FIG. 111D) in the distal end opening portion 503 of the elongated portion 502, thereby pressing the clip 511 until the clip 511 is completely closed (see FIG. 111E). In this state, a coil spring 546 exists between the drive member 535 and the probe 505, and therefore, the elasticity of the coil spring 546 pushes the clip 511 with a constant force.

In the condition where the clip 511 is thus completely closed, the ultrasonic oscillator 533 in the handle portion 501 is driven, and the ultrasonic oscillation is transferred to the clip 511 through the probe 505. The legs 511b of both ends of the clip 511 which are thus in contact with each other are welded with each other by means of heating due to ultrasonic oscillation, and are fixed in a closed form, thus completing the clipping of the tubular organ interposed between two legs 511b.

When the operation lever 532 is completely closed, the latch 538 and the transmission member 539 are engaged with each other again in the handle portion (see FIG. 108B). When the force closing the lever 532 is then released, the lever 532 naturally comes back to an original stand-by state in which the lever is opened, since the lever 532 is energized in the direction in which the lever 532 is opened. The drive member 535 and the transmission member 539 to be engaged with a latch 538 move backward. Simultaneously, the push member 513 and the probe 505 move backward in the elongated portion 502, and recover to the initial state shown in FIG. 108A.

Next, operation of the continuous ejection mechanism of clips 511 will be explained. When the clip 511, held by the first stopper plate spring 523 at a front position, is moved to the distal end side by the push member 513, the second stopper spring 524 positioned immediately before the cartridge 520 is caused to move up by the flange portion 525 on the upper surface of the push member 513, and the clip 511 disposed at the front end in the cartridge 520 is pushed forward to the front of the cartridge 520 by an energizing force applied through the spring 522 provided in the rear end side, so as to be in contact with the first stopper spring in the front end side and to keep on moving until this clip 511 stops at a nail portion 523a of the first stopper spring 523 (see FIG. 104B).

When the push member 513 starts moving backward, the second stopper spring 523 in the rear side enters again between the first one of the line of clips in the cartridge 520 and the clip 511 which have been fed before in the cartridge 520, thereby preventing the movement of respective clips 511. Then, the push member 513 completely moves to the rear end side and is brought into an initial state in which the push member 513 is engaged with the projection 511d of the clip 511 before the cartridge 520.

The above operation is repeated to continuously feed out a plurality of clips 511, thereby achieving continuous use of the applicator, with the elongated portion 502 inserted in a body cavity. The continuous ejection mechanism for clips 511 is not limited to the kind described above, but may be a belt drive type.

In addition, after use, the probe unit 548, handle portion 501, and the elongated portion 502 are disassembled as shown in FIG. 109, and the probe unit 548 and the handle portion 501 are subjected to cleaning and sterilization, and then, to re-cycle use.

The clip applicator of this embodiment functions not only as the push member 513 for pushing the clip 511 but also as the member for closing the clip 511, and the structure can thus be simplified. In addition, the structure inside the distal end portion of the elongated portion 502 is simplified, so that the size of the distal end portion can be reduced. When a blood vessel 555 is inserted in the distal end opening portion 503 thereby to locate a clip 511 around the blood vessel 555, the clip moves around behind the blood vessel 555. Therefore, the blood vessel 555 as the target can easily be viewed, and treatments can be made with higher safety and with improved operation ability.

Further, since a latch structure at the distal end of the legs of the clip 511 is not required any more, it is possible to prevent clips 511 from hooking up blood vessels when a clip 511 clips a blood vessel, and therefore, even a thick blood vessel 555 can be easily clipped.

In addition, since ultrasonic welding is used to fix the legs of a clip 511 closed, strong and secure clipping is achieved.

Since clips 511 are disposed linearly in the cartridge 520, the diameter of the elongated portion 502 can be reduced.

Since the clips 511 are made of organism absorptive material, debris does not remain in the human body. Further, since a latch or a hook used for fixing clips closed is not provided at both end portions of any the clip 511, a blood vessel is easily held and both ends of the legs of the clip 511 are fixed to each other by means of ultrasonic welding, and the closed condition can be securely maintained, thereby attaining a rigid clipping force.

Since a clip 511 does not requires any latch or hook portions, the size of the clip 511 can be reduced. Further, since clips are contained and disposed linearly in the cartridge, it is possible to provide a structure in which a plurality of clips are arranged within the width of the elongated portion 502, together with probes 505 as oscillation transmission members. Therefore, clips 511 can be used continuously, one after another, with the elongated portion 502 inserted in a body cavity during operation using an endoscope. This results in reductions in the operation time.

Since the distal end surface of the elongated portion 502 is slanting and since the distal end opening portion 503 is V-shaped, a target portion is not hidden by the distal end of the elongated portion, thus securing an excellent view field and improving the operation ability, when a blood vessel is clipped within the distal end opening portion 503.

Sealing of the probe housing 549 enables cleaning, disinfection, and EOG (ethylene oxide gas) sterilization, and the simple structure of the handle portion 501 enables cleaning, sterilization, and recycle use thereof.

Figure 114:
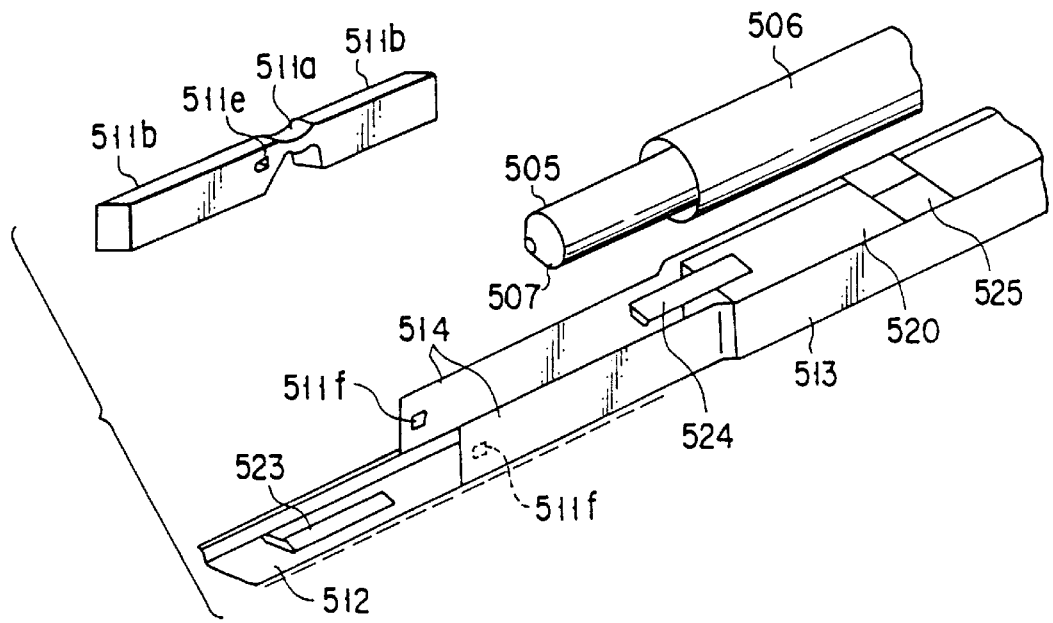

A modification of the above embodiment is shown in FIG. 114, wherein engagement holes 511e are provided in place of projections 511d on the side surfaces of the clip 511, while projections 511f to be engaged with the engagement holes 511e are provided at the distal ends of the push edges 514. In this case, excessive convex portions are removed from the shape of the clip 511, so that clips 511 slide more easily in the cartridge 520.

Further, the shape of the clip 511 is not limited to a linear one, but may be bent at an angle of 90°. In this case, clips can be more easily arranged at the distal end of the elongated portion 502.

Figure 115:
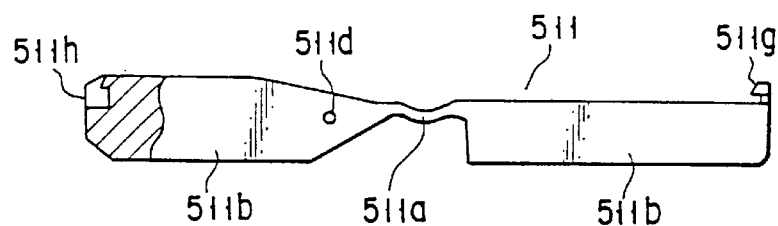
Figure 116B:
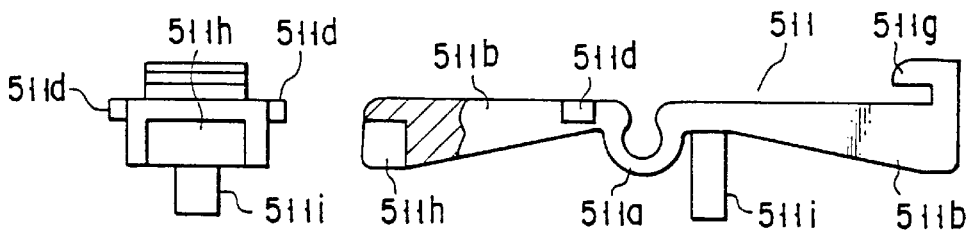
Figure 116A:
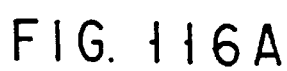
Figure 117:
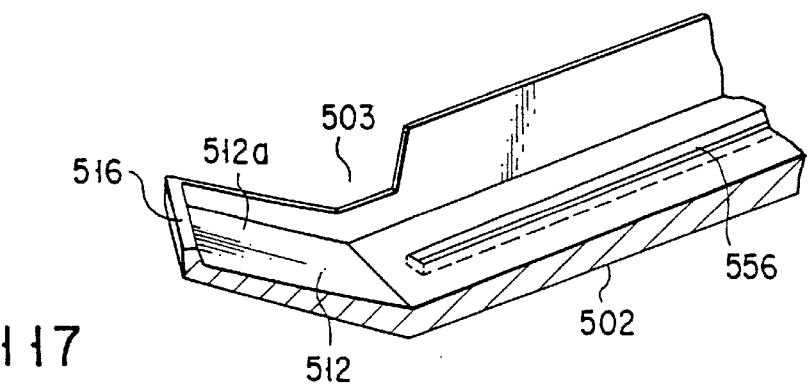
Figure 118A:
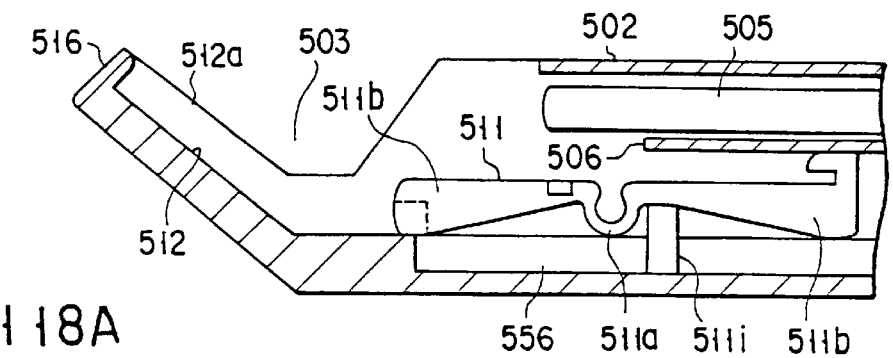
Figure 118B:
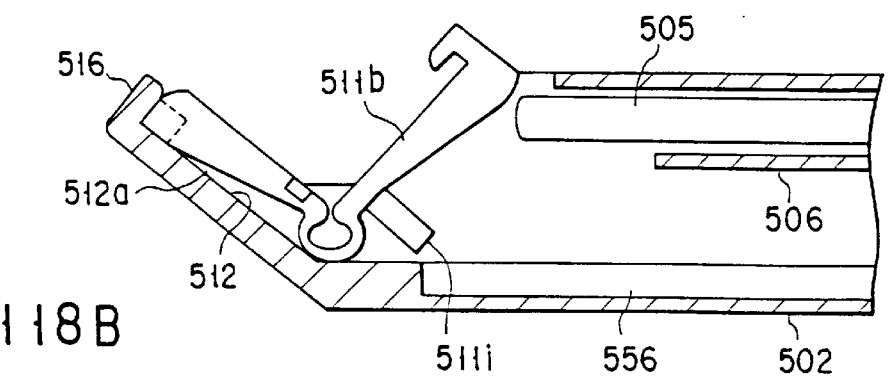

FIG. 115 shows a forty-third embodiment. In the clip 511 of this embodiment, a hook 511g is provided on the upper surface of one of legs 511b, while a receive portion 511h to be engaged with the hook 511g is provided on the upper surface of the other leg 511b. The receive portion 511h has a gap, and the hook 511g is prevented from being detached from the receive portion 511h after the hook 511g is once engaged with the receive portion 511h. The height of the legs 511b at both ends from their lower surfaces are substantially equal to each other.

Except for this point, the structure of this embodiment is substantially the same as that of the above forty-second embodiment excluding the ultrasonic oscillator 533 from the handle portion 501 thereof. The probe 505 is not especially limited to a columnar or cylindrical shape, but may have a plate-like shape. In addition, the material of the probe is not limited to titanium.

Thus, a clip 511 is moved to the slanting surface portion 512a at the distal end of the clip holder groove 512 by the push member 513 and is then made V-shaped. Thereafter, both ends of the legs 511b are pressed by the probe 505. In this state, the hook 511g and the receive portion 511h respectively provided on both ends of the clip 511 are engaged with each other, so that the clip is fixed closed. The other points of operation are similar to those of the forty-second embodiment as described above.

According to this embodiment, the handle portion 501 does not require an ultrasonic oscillator, thus simplifying the structure. In addition, the probe 505 can be made of a plate material and the probe cover can therefore be removed, and the diameter of the elongated portion 502 can be reduced much more. Since the height of the clip 511 from the lower surfaces of both end portions is substantially uniform, clips can be arranged in line. In addition, the same effects as achieved in the forty-second embodiment can be obtained.

FIGS. 116A to 118B show a forty-fourth embodiment. The clip 511 according to this embodiment is provided with an arm 511i extending from the lower surface of the leg 511b positioned in the rear side of the hinge portion 511a. The width of this arm 511i is smaller than that of the legs 511b. Further, in order to contain the arm 511i of the clip 511, a guide groove 556 for slidably engaging therein the arm 511i is provided in the center of the clip holder groove 512, such that the guide groove extends to be close to the distal end opening portion 503. Except for this point, this embodiment is similar to the forty-third embodiment.

When the distal end of the leg 511b of the clip 511 slides along the slanting surface and the arm 511i provided on the lower surface of the legs 511b, the arm 511i is pushed out from the distal end of the guide by the force which has made the clip 511 slide. Then, the leg 511b at the rear end side of the clip 511 rotates around the hinge portion 511a as the center of rotation, so that the clip 511 is V-shaped at the distal end opening portion 503. Thereafter, the probe 505 pushes the leg 511b in the rear side, so that the receive portion 511h is engaged with the hook 511g, thereby fixing the legs 511b of both ends closed.

According to this embodiment, since an arm portion 511i is provided for the clip 511, the rear leg 511b of the clip 511 can securely be made to stand up. Except for this point, the operation of this embodiment is similar to that of the forty-third embodiment.

Figure 119B:
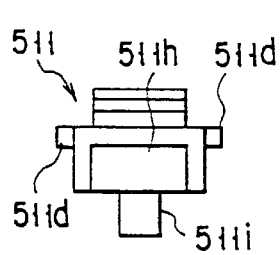
Figure 119A:
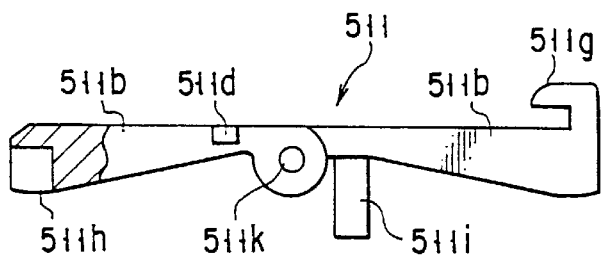
Figure 119C:
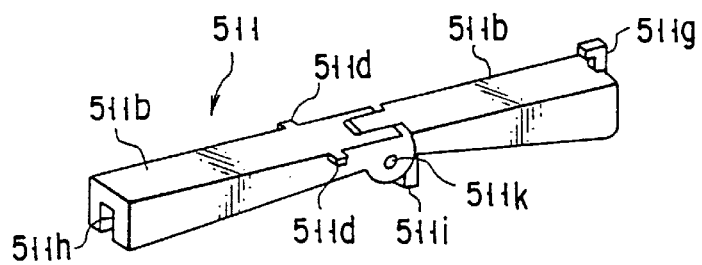

FIGS. 119A–119C show a modification of the clip 511 of the forty-fourth embodiment. This modification is an example in which a joint portion having a rotation shaft 511k is formed at the hinge portion 511a of the clip 511. Except for this point, this embodiment is similar to the forty-fourth embodiment.

According to this modification, since a rotation shaft 511k is provided, the force required for bending the clip 511 is advantageously reduced.

FIGS. 120 to 122 show an applicator according to the forty-fifth embodiment, wherein detailed explanation of the same components as used in the applicator of the forty-second embodiment will be omitted.

An opening portion 571 is provided at the distal end portion of the elongated portion 570 of the applicator. The opening portion 571 is constituted by respectively forming substantially U-shaped (or V-shaped) notch grooves in upper and lower wall portions of the sheath end portion of the elongated portion 570. The front side of the opening portion 571 is opened. The upper notch portion has the same shape as the lower notch portion, and these portions are symmetrical to each other. An organ 555 such as a blood vessel or the like can be transversely inserted from the front opened end of the opening portion 571 into the notch penetrating portion of this distal end opening portion 571. A clip 572 which clips the blood vessel 555 is provided at the opening is portion 571. The distal end portion forming this opening portion 571 has a side face in which a groove is formed. The upper and lower widths of the distal end portion are narrow, and the clip 572 of the opening portion 571 can be put inside the groove. A slanting surface 571a bent inwardly is formed on each of the left and right distal end edges of this opening portion 571.

In the elongated portion 570, a probe 573 having a quadrangular longitudinal cross-section is provided along the axial direction of the elongated portion 570, in a position behind the distal end opening portion 571, such that the probe 573 is slidable in the longitudinal direction of the elongated portion 570. The distal end of the probe 573 is formed in a convex shape, and the distal end of the probe 573 waits, facing the distal end opening portion 571, as shown in FIG. 120.

The lower portion of the elongated portion 570 projects generally in a convex shape, except for the distal end portion where the opening portion 571 is formed. In the elongated portion 570, a push member 574 made of a long plate-like member is provided along the axial direction of the elongated portion 570, in the projecting side of the probe 573, i.e., in the lower side thereof, such that the push member is slidable in the axial direction of the elongated portion 570. At a portion behind the opening portion 571, a guide groove 575, which makes the probe 573 and push member 574 slide, is formed to be continuous to the opening portion 571 described above. The opening portion 571 and the guide groove 575 are arranged linearly and coaxially.

A partition plate 576 is provided below the push member 574. A lower inner space partitioned by the partition plate 576 and projecting below the elongated portion 570 forms a clip container portion 577. The clip container portion 577 contains a plurality of clips 572 disposed in line, in a manner in which clips are directly contained therein or clips arranged in a cartridge of another member are contained therein. The distal end of the clip container portion 577 communicates with the guide groove in the front side of the prove 573 and in the rear side of the opening portion 571 through a clip feed passage 578.

The feed passage 578 has a slanting surface connected to the guide groove 575 from the clip container portion 577, and a clip 572 contained in the clip container portion 577 is fed into the guide groove 575, while guiding this clip by the slanting surface 578a.

The distal end portion is normally arranged so as to wait, positioned backward away from the portion where the clip feed passage 578 is connected with the slide guide groove 575. The distal end portion of the push member 574 has a forked shape, and a flange portion 574a to be pressed against the rear end of the clip 572 is formed, bent upward, at the distal end of the forked shape.

The clip 572 described above comprises a pair of legs 572a connected with each other through a hinge portion 572b, and is made of such a material as used for the clip according to the forty-second embodiment. In a natural state, the pair of legs of the clip 572 spread over due to elasticity of the hinge portion 572b. A concave portion 572c is formed in the rear end portion of the hinge portion 572b. Further, a plurality of clips 572 are contained and disposed in line in the clip container portion 577, with their hinge portions 572b oriented to the back side, and with the pair of legs 572a oriented to the front side. In addition, each of the clips is V-shaped in a natural state. Clips 572 disposed in line and contained in the clip container portion 577 are elastically pressed to the front side by an elasticity means such as a coil spring or the like, from the back side through a plunger or the like not shown, like in the forty-second embodiment described above.

The probe 573 and the push member 574 are driven to slide by the same means as used in the applicator according to the forty-second embodiment described above. Except for this point, the structure of this embodiment is similar to that of the forty-second embodiment.

Next, the operation of this applicator will be explained. In the clip container portion 577, since the clips 572 are pressed from the back side, the clip 572 at the distal end of the clips is pushed up along the slanting surface 578a of the feed passage 578, and is fed into the front slide guide groove 575 at the distal end of the probe 573.

Therefore, the elongated portion 570 is introduced, and an organ such as a blood vessel to be clipped is inserted in the notch portion of the distal end opening portion 571. The organ is thus caused to transversely pass through the distal end opening portion 571.

When the operation lever of the handle portion of the applicator is rotated toward the closed position, the push member 574 pushes the clip 572 at the top end of the clip toward the distal end opening portion 571. Further, when the operation lever is closed deeply, the probe 573 further slides toward the distal end opening portion 571, so that the clip 572 collides into the slanting surface 571a at the distal end edge of the distal end opening portion 571, and thereafter, the clip 572 is further kept pushed.

Therefore, the ends of both of the legs 572a are pushed inwardly along the slanting surface 571a, and the legs of the clip 572 are pushed to be closed. In addition, since the clip 572 is pushed with the left and right ends of a concave portion 572c of its the hinge portion 572b being engaged with the convex surface of the top end of the probe 573, the clip 572 is closed more securely. Thereafter, ultrasonic oscillation is transmitted to the probe 573, like in the forty-second embodiment as described above, and both of the legs 572a are welded to each other. Both legs are fixed in this closed form, thus completing the clipping of the legs.

When the operation lever of the handle portion is opened, the push member 574 is pulled back to a position behind the exit port of the feed passage 578, and the distal end of the probe 573 is pulled more backward to the initial state again. Then, the next clip 572 is pushed up onto the guide groove 575, and waits there until a next opportunity of use. Thus, a plurality of clips 572 can be continuously used, thereby leading to reductions in the operation time.

According to this embodiment, since an opening portion 571 is provided at the end surface of the top end of the elongated portion 570, a blood vessel can easily be clipped. In addition, clips 572 can be closed with a simple structure.

Note that in this embodiment, clips 572 can be contained in the cartridge with themselves being closed. In this case, the diameter of the elongated portion can advantageously be reduced.

Further, a convex and a concave shape may be provided in the inner surfaces of both legs 572a of the clip 572. In this case, both legs can advantageously be welded to each other, with ease.

Further, a clip made of resin is fixed in a closed form by ultrasonic oscillation welding, so that secure and strong clipping can be achieved. In addition, since a clip can be fixed in a closed form by ultrasonic welding, conventional hooks and latches need not be provided at end portions of a clip. The size of the clip can be reduced and the shape thereof can be simplified. Since clips are fed in the sliding direction of the oscillation transmission member, continuous closing and fixing of clips by means of ultrasonic oscillation welding can advantageously be achieved.

The material absorbable into body tissues, which is used in the present invention, many be one hitherto used or one having a low-thermal-deforming point. Even if the glass ceramic powder is absorbed into body tissues at so slow a rate as to remain unabsorbed into the tissues, it will not affect the body tissues at all.

FIGS. 123A to 129 show a forty-sixth embodiment. As shown in FIGS. 123A and 123B, a tissue-fixing medical device 601 has an elongated insertion section 602 arranged to be inserted into the body cavity and an operation section 603 which is operated at a position relatively adjacent to the operator The insertion section 602 has, at the leading end thereof, an applicator 604 and forceps 605. The operation section 603 is composed of a forceps operation section 606 and an applicator operation section 607.

As shown in FIGS. 124A, 124B and 125, a thread fixing member 610 made of thermoplastic resin is accommodated in the leading end portion of the insertion section 602. The applicator 604 for closing and fixing the thread fixing member 610 and forceps 605 for holding a suturing thread and suturing needle are disposed adjacent to the foregoing leading end portion. The forceps 605 consisting of two forceps jaws 608 and 609 are capable of opening/closing because the forceps jaw 608 is fixed and the forceps jaw 609 is permitted to be rotated.

An accommodation section 612 in the form of recess for accommodating the thread fixing member 610 and a thread fixing means, for example, an ultrasonic-wave transmission and pressing member 613 serving as a thread fixing means, are provided for the applicator 604. The accommodation section 612 accommodates the thread fixing member 610. The thread fixing member 610 has a structure such that a jaw 611a and a jaw 611b are closed. Note that the thread fixing means is not limited to the foregoing ultrasonic wave fixing means.

FIGS. 126 to 129 are diagrams showing the process of a suturing operation by using the tissue-fixing medical device 601. FIG. 126 is a diagram showing a leading end of the insertion section 602 of the tissue-fixing medical device 601 inserted, from outside, into the body cavity through a treatment opening (not shown) formed in the abdomen and a leading end 614a of a needle holder 614 inserted, from outside, into the body cavity through another treatment opening (not shown) formed in the abdomen.

Initially, the leading end of a thread and needle 616, which has been held at the leading end 614a of the needle holder 614 on the outside of the body, is allowed to penetrate an end of an incised portion 615 of the organization so as to be discharged from the surface of another end of the incised portion 615. The leading end of the thread and needle 616 projecting over the surface is, as shown in FIG. 127, held and pulled by the forceps jaws 608 and 609 of the forceps 605 by operating the forceps operation section 606.

Then, the thread and needle 616 are shifted to the leading end 614a of the needle holder 614 to continuously suturing the required portion of the organization When the suturing operation is completed, the thread and needle 616 are held by the leading end 614a of the needle holder 614, as shown in FIG. 128. While applying a tension to the thread portion of the thread and needle 616, the thread portion of the thread and needle 616 is disposed between jaws 611a and 611b of the thread fixing member 610 accommodated in the applicator 604.

Then, the applicator operation section 607 is operated, and then the ultrasonic-wave transmission and pressing member 613 is moved forwards so that the jaws 611a and 611b of the thread fixing member 610 are closed. When ultrasonic vibrations are transmitted to the ultrasonic-wave transmission and pressing member 613, the ultrasonic vibrations are transmitted to the jaw 611a so that the jaws 611a and 611b are welded, as shown in FIG. 129. At this time, also the thread portion of the thread and needle 616 is welded. As a result, since the jaws 611a and 611b cannot be opened again, the thread fixing operation is completed.

Since this embodiment has the above-mentioned structure such that the applicator 604 having the ultrasonic-wave transmission and pressing member 613, serving as the thread fixing means, and the forceps 605 are disposed so as to be simultaneously inserted into the body cavity, the necessity to remove the forceps 605 to the outside of the body and to insert the applicator 604 for fixing the thread into the body cavity when the suturing operation is completed can be eliminated to complete the thread fixing operation with one tissue-fixing medical device 601. Therefore, time required to complete the suturing operation can be shortened. Since time required to complete the operation including the suturing operation can be shortened, the load, which must be borne by a patient, can be reduced. Moreover, the operator is able to easily operate the tissue-fixing medical device 601 so that the suturing operation is easily be completed. Since the ultrasonic welding method is employed to fix the thread, the sutured portion can be strengthened. As a result, the thread fixing operation can be performed reliably.

Although this embodiment has the structure such that the sheath for the applicator 604 and that for the forceps 605 are formed completely integrally, a modification as shown in FIG. 130A may be employed in which a sheath 604a for the applicator 604 and a sheath 605a for the forceps 605 may be disposed adjacently while being allowed to run parallel to each other. Thus, the sheath 604a and the sheath 605a are connected to each other by connecting members 680.

Also the accommodation section 612 in the form of the recess for accommodating the thread fixing member 610 of the applicator 604 may be structured as is employed in a modification shown in FIG. 130B such that a separation preventive groove 612a, arranged to be engaged to the jaw 611a of the thread fixing member 610 to prevent separation of the thread fixing member 610, is formed at the end portion of the opening portion of the accommodation section 612. In this case, the thread fixing member 610 can reliably be accommodated.

FIG. 131 shows a forty-seventh embodiment having the same structure as that of the forty-sixth embodiment except the applicator 604. An applicator 622 according to this embodiment has a cartridge 623 which accommodates a plurality of thread fixing members 610 disposed in the same direction. Moreover, the cartridge 623 includes a supply means 625, such as a slide bar having a hooking claw, for supplying the thread fixing member 610 to the accommodation section 624. An ultrasonic transmission and pressing member 626 for closing and fixing the thread fixing member 610 is disposed on the surface on which the cartridge 623 is disposed.

The operation of this embodiment will now be described. Similarly to the forty-sixth embodiment, the thread portion of the thread and needle 616 is disposed on the inside of the thread fixing member 610 when the suturing operation is completed. Then, the thread fixing member 610 is pushed by the ultrasonic transmission and pressing member 626. In the foregoing state, ultrasonic waves are transmitted so that the jaws 611a and 611b of the thread fixing member 610 are welded and thus the thread is fixed. Then, the thread fixing member 610 is discharged after the thread fixing operation has been completed, then the thread fixing member 610 accommodated in the cartridge 623 is introduced into the accommodation section 624 by the supply means 625. Thus, the thread fixing operation can be performed successively.

As a result of this embodiment, a successive suturing operation using a plurality of threads and needles 616 can be performed such that insertion of the needle holder 614 holding the thread and needle 616 enables a next suturing operation to be performed. Since a necessity of loading the thread fixing member 610 into the applicator 604 on the outside of the body can be eliminated to suture the required portion of the organization, time required to complete the suturing operation can be shortened. Since time required to complete the operation including the suturing operation can be shortened, the load, which must be borne by a patient, can be reduced. Moreover, the operator is able to easily operate the tissue-fixing medical device 601 so that the suturing operation is easily be completed. Since the ultrasonic welding method is employed to fix the thread, the sutured portion can be strengthened. As a result, the thread fixing operation can be performed reliably.

FIGS. 132 and 133 are diagrams showing a forty-eighth embodiment having the same structure as that of the forty-sixth embodiment except the applicator 604. An applicator 629 according to this embodiment is permitted to move in the longitudinal direction along an axis running parallel to the major axis of the insertion section 602 to a farther position (see FIG. 133) over the forceps 605 from a position (see FIG. 132) in the insertion section 602 disposed more adjacent to the operator than the forceps 605. Moreover, the forceps 605 cannot move in the longitudinal direction in this embodiment.

The operation of this embodiment will now be described. Since the applicator 629 can be accommodated in the insertion section 602 when the suturing operation is performed, the suturing operation is not interrupted by the applicator 629. Since the applicator 629 is able to move more forward than the forceps 605 when the thread is fixed, the thread can be fixed without interference with the forceps 605.

Since this embodiment enables the suturing operation and the thread fixing operation to smoothly be performed, time required to complete the suturing operation can be shortened. Since time required to complete the operation including the suturing operation can be shortened, the load, which must be borne by a patient, can be reduced. Moreover, the operator is able to easily operate the tissue-fixing medical device 601 so that the suturing operation is easily be completed.

FIGS. 134 and 135 are diagrams showing a modification of this embodiment. Forceps 630 according to this embodiment are able to, in a direction running parallel to the major axis of the insertion section 602, move longitudinally from a farther position (see FIG. 134) than the applicator 604 to a position (see FIG. 135) in the insertion section 602 disposed more adjacent to the operator than the applicator 604. Moreover, the applicator 604 cannot move longitudinally. Since the suturing operation is, in this embodiment, performed after the forceps 630 have been moved forwards, the forceps 630 do not interfere with the applicator 604 during the suturing operation. Since the forceps 630 can be moved rearwards when the thread is fixed, the thread fixing operation can be performed without the interference with the forceps 630. Thus, effects similar to those obtainable from the forty-eighth embodiment can be obtained.

FIGS. 136 to 138B are diagrams showing a forty-ninth embodiment. Reference numeral 631 represents a medical suturing device according to this embodiment. The medical fixing device 631 has an operation section body 631a provided with an ultrasonic oscillation section 633 to which an ultrasonic transmission and pressing member 632 is attached. A handle 634 is attached to the ultrasonic oscillation section 633. A sheath 635 and a sheath 636 each of which is provided to serve as an outer pipe for the ultrasonic transmission and pressing member 632 are slidably attached to the handle 634 in the axial direction of the sheath 636 by the spring force of a spring 637. Moreover, the handle 634 is permitted to move along a slide groove 639 formed in the case 638.

The case 638 disposed at an end of the insertion section side of the slide groove 639 is provided with a latch 640 structured to be engaged to an engagement section 634a of the handle 634. A spring 641, structured to be abutted against the sheath 636, is disposed in the insertion section side of the case 638.

Moreover, forceps 643 are disposed at the leading end of an insertion section 642 of the medical fixing device 631. In addition, an applicator 644 disposed at the leading end of the sheath 635 is provided for the leading end of the insertion section 642. The applicator 644 has an accommodation section 645 on which a thread fixing member 610, structured similarly to that according to the forty-sixth embodiment, is mounted.

The operation of this embodiment will now be described. When the handle 634 is moved forwards along the slide groove 639, the ultrasonic oscillation section 633, the ultrasonic transmission and pressing member 632, the sheath 635, the sheath 636 and the spring 637 move forwards, as shown in FIG. 137. Thus, the applicator 644 at the leading end of the insertion section 642 is moved forwards.

When the handle 634 is furthermore moved forwards, the spring 637 is contracted. Thus, the ultrasonic oscillation section 633 and the ultrasonic transmission and pressing member 632 are moved forwards with respect to the sheath 635 and the sheath 636. At this time, the leading end of the ultrasonic transmission and pressing member 632 presses the thread fixing member 610 so that the thread fixing member 610 is brought to a state where it is closed, as shown in FIG. 138A. At this time, the spring 637 is contracted by a degree corresponding to the distance for which the thread fixing member 610 has been moved so as to be closed.

Further movement of the handle 634 in the forward direction causes the sheath 636 to be brought into contact with the spring 641. Thus, the spring 641 is contracted so that the engagement section 634a is engaged to the latch 640. Since compressive force has been applied to the thread fixing member 610 at this time as shown in FIG. 138B, the amount of contraction realized attributable to the contraction of the spring 641 can be absorbed because the spring 637 is contracted. When ultrasonic waves are emitted from the ultrasonic oscillation section 633, the suturing thread (not shown) accommodated in the thread fixing member 610 and the jaws 611a and 611b of the thread fixing member 610 are welded to one another. That is, the ultrasonic transmission and pressing member 632 keeps contact with the thread fixing member 610 by engagement between the engagement section 634a and the latch 640, until the jaws 611a and 611b are welded to one another by ultrasonic waves. When the latch 640 has been released after the welding operation has been completed, the thread fixing member 610 is separated from the accommodation section 645. Thus, the thread fixing operation is completed and the suturing operation is ended.

Since this embodiment has the structure such that the accommodated applicator 644 is moved more forwards than the forceps 643 when the thread fixing operation is performed, the thread fixing operation can be performed without interference with the forceps 643. Since the compressive force is given from the spring to the thread fixing member 610, engagement to the latch 640 causes predetermined compressive force to be given. Thus, ultrasonic waves can efficiently be transmitted to the thread fixing member 610. As a result, the thread fixing strength can be enlarged and, therefore, the thread can be fixed more reliably.

Since the foregoing operation can be performed by only the handle 634, the apparatus can easily be operated. Since the thread fixing operation can be completed in a short time, loads, which must be borne by the patient and the operator, can be reduced. A structure as shown in FIGS. 138A and 138B may be employed in which the forceps 643 and the operation section body 631a are not disposed on one straight line but the ultrasonic oscillation section 633, the ultrasonic transmission and pressing member 632 and the applicator 644, including the thread fixing member 610, are disposed on the same straight line. In this case, ultrasonic waves can furthermore efficiently be transmitted. Thus, the thread can be fixed more reliably.

The applicator 622 having the cartridge 623 for accommodating a plurality of thread fixing members 610 according to the forty-seventh embodiment may be employed in place of the applicator 644. In this case, the apparatus can be operated easily and the thread fixing operation can be completed in a short time so that the loads for the patient and the operator can be reduced.

FIGS. 139 and 140 are diagrams showing a fiftieth embodiment in which the structure of the medical fixing device 631 has basically the same structure as that according to the forty-ninth embodiment. Therefore, the same reference numerals are given to the same elements, and the same elements are omitted from description. The medical fixing device 631 according to this embodiment has a forceps unit section 646, a thread-fixing applicator unit section 647 and a shell section 648. The forceps unit section 646 is detachably attached to the shell section 648 by a fixing screw 649 provided for the base portion of the forceps unit section 646 and serving as an assembling member.

Therefore, when the fixing screw 649 is loosened or fastened, the forceps unit section 646, the thread-fixing applicator unit section 647 and the shell section 648 can be decomposed or assembled, as shown in FIG. 140. Thus, the forceps unit section 646 and the thread-fixing applicator unit section 647 can solely and independently be used.

As a result of the structure according to this embodiment, each of the forceps unit section 646 and the thread-fixing applicator unit section 647 can be used solely without a necessity of individually purchasing the same, if necessary. Since the forceps unit section 646 and the thread-fixing applicator unit section 647 may be combined with each other to perform a required operation, the medical expenses of a hospital or the like can be reduced. Since the foregoing elements can be decomposed when they are washed, the washing operation can be performed easily and satisfactorily FIGS. 141A to 141D are diagrams showing a fifty-first embodiment of the present invention and are front views of the medical fixing device 631. When the fixing screw 649 serving as the assembling means according to the fiftieth embodiment is loosened, the handle 634 can be rotated to the leftward position 650b or a rightward position 650c relative to the axis of the ultrasonic transmission and pressing member 632. Moreover, the thread-fixing applicator unit section 647 can be rotated independently from the handle 634 to be moved to an inclined position 650d.

According to this embodiment, the handle 634 can be rotated to permit the operator to use the required hand to operate the apparatus regardless of the size of the hand of the operator. Thus, the apparatus according to this embodiment can easily be operated. Since the thread-fixing applicator unit section 647 can be rotated, an optimum angle, at which the suturing thread can easily be fixed, can be selected.

FIG. 142A is a diagram showing the operation section 603 of the tissue-fixing medical device 601 according to a fifty-second embodiment. First and second handles 651 and 652 are rotatively engaged to the operation section 603. A first link 653 rotatively attached to the first handle 651 and a second link 654 rotatively attached to the second handle 652 are mutually rotatively attached.

An end of a leaf spring 655 is secured to an end portion of the second handle 652, while another end of the same is slidably, elastically and forcibly brought into contact with the inner surface of the first handle 651. Moreover, a handle lock 656 is detachably disposed in the rotational attachment portions of the first and second handles 651 and 652. Thus, the first and second handles 651 and 652 can be locked.

Therefore, when the first and second handles 651 and 652 are squeezed, the jaws of the forceps 605 are closed. When the squeezing force is reduced, the first and second handles 651 and 652 are opened by the spring force of the leaf spring 655 so that the jaws of the forceps 605 are opened. After the operation of the first and second handles 651 and 652 has been completed and then the handle lock 656 has been brought to a space between the first handle 651 and the second handle 652, the first and second handles 651 and 652 and the jaws of the forceps 605 cannot be opened.

As a result of the structure according to this embodiment, introduction of the handle lock 656 into the space between the first handle 651 and the second handle 652 after the operation of the operation section 603 has been completed causes the first and second handles 651 and 652 not to be opened. Also the jaws of the of the forceps 605 cannot be opened. Therefore, the thread fixing operation is not interrupted and thus the thread fixing operation can efficiently be performed.

FIG. 142B is a diagram showing a fifty-third embodiment and illustrating a connection and attaching portion between the forceps 605 and a second link 654 and forceps 657 having different forceps structure from that of the forceps 605. A forceps attaching section 659 is disposed in the base portion of a drive shaft 658 of the forceps 605. The forceps attaching section 659 is structured to be detachable with respect to a forceps receiver 660 provided for the second link 654.

The drive shaft 658 for connecting the forceps attaching section 659 and the leading end of the forceps 605 to be held to each other is made of a super-elastic material. Thus, the forceps 605 can be inserted/removed through a curved section 662 of a sheath 661, as shown in FIG. 142A. Therefore, also the forceps 657 having the leading end holding portion, the shape of which is different from that of the forceps 605, are provided with a drive shaft 658 made of the super-elastic material. Thus, the forceps 657 can be inserted into the sheath 661 so as to be attached to the forceps receiver 660.

Therefore, the forceps 605 can be removed from the leading end of the insertion section thereof after the forceps attaching section 659 has been removed from the forceps receiver 660. Moreover, the forceps 657 having a leading end having a different shape can be inserted into the sheath 661 from the leading end of the insertion section thereof, and then it can be further inserted toward the operation section from the curved section 662 of the sheath 661 so as to be attached to the forceps receiver 660.

Thus, this embodiment enables the operation for opening/closing the forceps 605 and 657 to be performed smoothly even if the sheath 661 has a curved shape. Since the forceps 605 or 657 may arbitrarily be selected to be mounted, a required operation can easily be performed. Since the forceps 605 or the forceps 657 can be removed from the sheath 661, the forceps can easily be washed with a satisfactory result.

FIGS. 143A to 147B are diagrams showing a fifty-fourth embodiment. As shown in FIGS. 143A to 143C, the surgical operation fixing apparatus according to this embodiment is composed of an operation section 701 and an elongation section 702 connected to the operation section 701.

As shown in FIGS. 144A to 147B, the elongation section 702 is composed of a sheath 703, a clip holder 704, a holder opening/closing means 705, a plurality of fixing clips 706, a clip cartridge 707 serving as a clip accommodating portion, a clip supply means 708, a pusher (bar) 709 and an ultrasonic probe (for example, plate shape) 710.

It is preferable that the diameter of the sheath 703 be not larger than 12 mm. The sheath 703 has a circular cross sectional shape. The sheath 703 has, in the inner central portion thereof, the ultrasonic probe 710 which is disposed detachably. The clip cartridge 707 is disposed on either side (on the upper side in the case shown in FIG. 144A) with respect to the ultrasonic probe 710. On another side of the same (on the lower side in the case shown in FIG. 144A), there is disposed the holder opening/closing means 705.

A partition member 711 made of metal or synthetic resin is disposed in the sheath 703 in order to divide the inner portion into a portion for disposing the clip cartridge 707 and a portion for disposing the holder opening/closing means 705. The leading end of the partition member 711 is allowed to slightly project over the opening formed at the leading end of the sheath 703. A support-point pin 712 is secured between a side wall at the leading end of the sheath 703 disposed in front of the holder opening/closing means 705 and the partition member 711, the support-point pin 712 being disposed perpendicular to the axial direction of the sheath 703. An intermediate portion between an upper holder 704a and a lower holder 704b forming the clip holder 704 is rotatively received by the support-point pin 712.

The upper holder 704a and the lower holder 704b are bent sidewards (upwards in the case shown in FIG. 144A) from positions adjacent to the supported portions. The leading ends of the upper holder 704a and the lower holder 704b are located in front of the leading end of the ultrasonic probe 710. A U-shape opening spring 713 is disposed to hold the support-point pin 712, the opening spring 713 being disposed adjacent to the support portions of the upper holder 704a and the lower holder 704b. Two leg portions 713a of the opening spring 713 are bent perpendicularly so as to be secured to the inside portion adjacent to the support portions of the upper and lower holders 704a and 704b so that the upper and lower holders 704a and 704b are urged in a direction in which they are opened. Moreover, a U-groove 714 for holding the fixing clips 706 and guiding the movement of the same is formed in each of the opposite surfaces of the upper and lower holders 704a and 704b. A stopper 715 in the form of a projection for the clips 706 is formed at the leading end of the U-groove 714, that is, at the leading end of each of the upper and lower holders 704a and 704b.

A pin 716 is allowed to project over the base portion of each of the upper and lower holders 704a and 704b. An end of a link 717 is rotatively connected to each of the pins 716. Another end of each of the links 717 is connected to a connection pin 719 of one slider 719 serving as the holder opening/closing means 705. Thus, a link mechanism 720 is formed. When the slider 719 is operated to move forwards, the base portions of the upper and lower holders 704a and 704b are expanded so that the upper and lower holders 704a and 704b are rotated relative to the support-point pin 712. As a result, the leading ends of the upper and lower holders 704a and 704b are closed against the spring force of the opening spring 713.

The slider 718 is supported in a slider guide groove 721 formed in the partition member 711 in such a manner that the slider 719 is able to move forwards and rearwards. The pusher 709 is arranged to abut against the rear end of the slider 719 through a pusher spring 722 accommodated in the slider guide groove 721. The pusher 709 is supported by the pusher guide groove 723 formed in the partition member 711 in such a manner that the pusher 709 is able to move forwards and rearwards. When the pusher 709 is moved forwards, forward pressure is applied to the slider 718 through the pusher spring 722.

As shown in FIG. 146, the slider guide groove 721 has a width slightly smaller than that of the pusher guide groove 723. A stepped section 724 is formed at the rear end of the slider guide groove 721. The stepped section 724 is formed to restrict the stroke of the pusher 709 in the forward direction. That is, the elastic force of the pusher spring 722 causes the upper and lower holders 704a and 704b to be closed with predetermined force.

A connection member 725 projecting upwards is secured to a position adjacent to the base portion of the pusher 709. Moreover, the base portion of the pusher 709 is, as shown in FIG. 144A, connected to a pipe bar connection section 728 formed in the leading end of the pusher pipe 727. The pipe bar connection section 728 is formed into an annular shape secured to the leading end of the pusher pipe 727, the pipe bar connection section 728 having an insertion hole 729, through which the ultrasonic probe 710 is inserted. Moreover, the pipe bar connection section 728 has a tapered section 730 for guiding insertion of the ultrasonic probe 710, the tapered section 730 being formed on the surface opposite to the operation section 701. A cut portion 731 is formed in the inner surface of the insertion hole 729 of the pipe bar connection section 728, the cut portion 731 being engaged and connected to an engaging section 732 formed in the base portion of the pusher 709.

The fixing clips 706, the clip cartridge 707 and the clip supply means 708 will now be described. The fixing clip 706 is made of resin manufactured by blending polyactic acid and polyglycolic acid and permitted to be absorbed by the organization or thermoplastic resin, such as nylon, which is adaptable to the organization. The fixing clips 706 having V-shape has two leg portions 706a, two leg portions 706a, 706 being connected to each other by a hinge 706b.

A plurality of fixing clips 706 are accommodated in the clip cartridge 707 to form a line facing the leading end of the sheath 703 in such a manner that the two leg portions 706a are overlapped. The clip cartridge 707 has side rails 733 each having a shallow U-shape cross sectional shape, the side rails 733 being opened toward the side portion (upper portion in the case shown in FIG. 144A) of the sheath 703. The bottom surface of the side rail 733 is received and secured by a wide U-groove 734 formed in the partition member 711. The bottom portion of the wide U-groove 734 of the partition member 711 has a narrow U-groove 735 into which the leading end of the ultrasonic probe 710 is inserted.

A movable plate 736, capable of moving forwards and rearwards, is accommodated in the inner bottom portion of the side rails 733. A fixed plate 737 serving as a cover for closing the opening of the side rails 733 is disposed to be opposite to the movable plate 736. The fixed plate 737 is held and secured to the side rails 733 by a holding member 738. The fixing clips 706 is accommodated between the movable plate 736 and the fixed plate 737.

A plurality of tag shape blades 736a outwards, diagonally and forwards project over the movable plate 736 to correspond to the intervals of the fixing clips 706 accommodated in the clip cartridge 707. That is, the blades 736a are integrally formed to project over the movable plate 736 by cutting and raising the movable plate 736 to have elasticity so as to be brought into contact with the rear portion of the hinge 706b of the fixing clips 706. Also tag shape blades 737a outwards, diagonally and forwards project over the fixed plate 737 to correspond to the intervals of the fixing clips 706 accommodated in the clip cartridge 707. That is, also the blades 737a are integrally formed to project over the fixed plate 737 by cutting and raising the fixed plate 737 to have elasticity so as to be brought into contact with the rear portion of the hinge 706b of the fixing clips 706.

The side rails 733 forming the clip cartridge 707 project over the sheath 703 to be located in the side portion of the clip holder 704 in such a manner that the leading end of the ultrasonic probe 710 is disposed between the side rails 733. An opening 739 having a width permitting the fixing clips 706 to pass through is formed in the side rail 733 in the portion projecting over the leading end of the sheath 703. Moreover, a mounting spring 740 which is a leaf spring having a base portion secured to the fixed plate 737 is disposed in a portion opposite to the opening 739 so that the clip 706 supplied from the leading end of the clip cartridge 707 is loaded into the clip holder 704 through the opening 739.

As shown in FIG. 145, the base portion of the movable plate 736 extends rearwards. An elongated section 741 has an elongated hole 742 formed in the longitudinal direction. The leading end of the connection member 725 bent to bypass the insertion section of the ultrasonic probe 710 is inserted into the elongated hole 742. The elongated hole 742 is designed to have a length capable of absorbing the difference between the stroke for the fixing clips 706 to be moved to the clip holder 704 attributable to the forward movement of the ultrasonic probe 710 and the stroke for the fixing clips 706 in the clip cartridge 707 to be supplied.

A clip supply means 708 is formed which forwards supplies the fixing clip 706 in the clip cartridge 707 when the movable plate 736 is pushed forwards attributable to the forward sliding movement of the pusher 709. That is, when the fixing clip 706 is closed by the clip holder 704, the frontmost clip 706 in the clip cartridge 707 can be supplied forwards. Since the movable plate 736 has been moved forwards at this time, the opening 739 is closed by the leading end of the movable plate 736. Therefore, the supplied clip 706 is held while being pressed against the movable plate 736 by the loading spring 740 so that another fixing clip 706 is not mounted on the clip holder 704.

The operation section 701 and the ultrasonic probe 710 will now be described. The operation section 701 is composed of a handle 743, a lever 744, an ultrasonic oscillator 745, an oscillator holder 746, a movement body 747 serving as an oscillator moving means, an elongated section connection means 748 and a pusher moving means 749.

The handle 743 projects sidewards with respect to the axial direction of the elongation section 702 so as to be held by the hand of the operator. An intermediate portion of the lever 744 is rotatively supported by the handle 743 by a rotative support shaft 744a. Moreover, the movement body 747 is supported by the handle 743 in such a manner that the movement body 747 is able to move longitudinally. Pins 750 project over the side surfaces of the movement body 747. An engaging hole 751 formed in the end portion of the lever 744 is engaged to the pin 750 so that the movement body 747 is moved longitudinally when the lever 744 is operated.

The oscillator holder 746 is disposed at the rear end of the ultrasonic oscillator 745. The oscillator holder 746 and the movement body 747 are connected to each other by a spring 752 so that movement of the movement body 747 is transmitted to the oscillator holder 746 through the spring 752. Moreover, a projection member 753 projecting forwards over the handle 743 is provided for the movement body 747. A pressing member 754 upwardly projecting for pressing the base portion of the pusher pipe 727 is integrally formed with the leading end of the projection member 753. That is, the structure is designed in such a manner that the spring 752 makes the force given to the ultrasonic probe 710 and the pusher pipe 727 at the time of the forward movement to be constant in order to protect the fixing clips 706 from being applied with excessively large force.

An elongated section receiving member 755 for forming the elongated section connection means 748 is disposed in the leading end of the handle 743. A knob 756 arranged to be rotated integrally with the sheath 703 is provided for the elongated section receiving member 755. The rotation of the knob 756 permits the direction of the clip holder 704 with respect to the handle 743 to be determined arbitrarily. A flange 703a is provided for the base portion of the sheath 703. A flange fixed plate 757 in the form of a pair of holding plates provided for the elongated section receiving member 755 is rotatively secured to the flange 703a.

Also a flange 727a is provided for the base portion of the pusher pipe 727 inserted into the sheath 703. The base portion of the pusher pipe 727 projects rearwards over the base portion of the sheath 703. A restoration spring 758 is interposed between the flanges 703a and 727a so that a pusher moving means is formed.

The ultrasonic oscillator 745 has a vibration transmission member 759 projecting forwards. The ultrasonic probe 710 is connected to the leading end of the vibration transmission member 759 through a screw connection section 760. The ultrasonic probe 710 is made of metal, such as stainless steel, duralumin or Ti6Al.4V and has a base portion formed into a cylindrical shape. A portion of the ultrasonic probe 710 from an intermediate engaging hole 751 to the leading end is formed into a flat shape. The leading end of the ultrasonic probe 710 has a recess 752 which is able to fit the shape of the base portion of the fixing clips 706.

The operation of the surgical operation fixing apparatus having the above-mentioned structure will now be described.

In an initial stage, the upper and lower holders 704a and 704b of the clip holder 704 are opened by the urging force of the opening spring 713, as shown in FIG. 145. The leading end of the clip 706 supplied from the clip cartridge 707 is engaged to the U-groove 714 in a state where the two leg portions 706a of the fixing clips 706 are opened.

When the handle 743 of the operation section 701 is held and the lever 744 is pulled in the above-mentioned state, the movement body 747 is moved forwards through the pin 750 engaged to the engaging hole 751. The movement of the movement body 747 is transmitted to the oscillator holder 746 through the spring 752. Therefore, the ultrasonic oscillator 745 is moved forwards so that the ultrasonic probe 710 connected to the ultrasonic oscillator 745 through the vibration transmission member 759 is moved forwards in the sheath 703 and therefore the fixing clip 706 is pushed forwards by the recess 752 formed in the leading end of the ultrasonic probe 710. As a result, the clip 706 is moved along the U-groove 714 of each of the upper and lower holders 704a and 704b so that the leading end of the leg portion 706a is brought into contact with the stopper 715 and thus the clip 706 is stopped.

At this time, the pressing member 754 presses the pusher pipe 727 through the projection member 753 attributable to the forward movement of the movement body 747. As a result, the pusher pipe 727 is moved forwards so that also the pusher 709 connected to the pusher pipe 727 is moved forwards. However, since the leading end of the pusher 709 is not in contact with the pusher spring 722 at this time, the link mechanism 720 is not operated so that the upper and lower holders 704a and 704b remain the opened state.

In the above-mentioned state, the surgical instrument is moved forwards toward tubular tissue X required to be fixed so that the tubular tissue X is interposed between the leg portions 706a of the fixing clips 706 held by the clip holder 704, as shown in FIG. 146.

When the lever 744 is further rotated, the pusher pipe 727 is moved forwards so that also the pusher 709 connected to the pusher pipe 727 is moved forwards. As a result, the leading end of the pusher 709 is brought into contact with the pusher spring 722. Thus, the slider 719 is moved forwards through the pusher spring 722. Therefore, the base portion of the upper and lower holders 704a and 704b is expanded by the link mechanism 720 so that the upper and lower holders 704a and 704b are rotated against the urging force of the opening spring 713 in such a manner that the support-point pin 712 serves as the support point. Thus, the leading ends of the upper and lower holders 704a and 704b are closed so that the tubular tissue X is held between the upper and lower holders 704a and 704b. When the pusher 709 is moved further forwards, the leading end of the pusher 709 is brought into contact with the stepped section 724 so that the forward stroke of the pusher 709 is restricted. Therefore, the elasticity of the pusher spring 722 closes the upper and lower holders 704a and 704b with predetermined force. Thus, even if the lever 744 is pulled strongly, the clip 706 can be protected from excessively large force being applied.

If the ultrasonic oscillator 745 in the operation section 701 is operated in the above-mentioned state, ultrasonic vibrations are transmitted to the clip 706 through the ultrasonic probe 710. As a result, the portion of the fixing clips 706 in which the leading ends of the leg portions 706a are in contact with each other is welded by the ultrasonic waves so that the clip 706 is brought to a closed state and, therefore, the tubular tissue X held by the fixing clips 706 is fixed.

When the clip holder 704 is closed due to the forward movement of the pusher 709, the connection member 725 disposed at an intermediate position of the pusher 709 is brought into contact with the leading end of the elongated hole 742 formed in the movable plate 736 of the clip cartridge 707. Therefore, the movable plate 736 is moved forwards so that the blade 736a provided for the movable plate 736 forwards presses the rear end of the fixing clips 706 in the clip cartridge 707. As a result, the frontmost clip 706 is moved to the frontmost position in the clip cartridge 707 so as to be supplied to the position of the opening 739 formed in the side rail 733. Since the opening 739 has been closed by the leading end of the movable plate 736, the fixing clip 706 remains the state where it is pressed against the movable plate 736 by the loading spring 740.

When the tubular tissue X has been fixed and then the force for pulling the lever 744 has been reduced, the restoration force of the spring 752 rearwards moves the ultrasonic oscillator 745. Also the ultrasonic probe 710 is moved rearwards so that the leading end of the ultrasonic probe 710 is separated from the fixing clip 706 with which the fixing operation has been completed. Also the restoration spring 758 is elongated due to the urging force, the pusher pipe 727 is moved rearwards. Thus, also the pusher 709 connected to the pusher pipe 727 is moved rearwards. As a result, also the pusher spring 722 is elongated and also the slider 719 is moved rearwards. Thus, the link mechanism 720 opens the upper and lower holders 704a and 704b of the clip holder 704.

As a result of the above-mentioned operation, the connection member 725 disposed at an intermediate position of the pusher 709 is brought into contact with the rear end of the elongated hole 742 formed in the movable plate 736 of the clip cartridge 707. Therefore, the movable plate 736 is moved rearwards, thus causing the opening 739 to be opened. Thus, the clip 706 supplied to the frontmost position in the clip cartridge 707 is loaded into the clip holder 704 through the opening 739 due to the spring force of the loading spring 740. Although force acts in a direction in which the blade 736a rearwards moves the clip 706 in the clip cartridge 707 when the movable plate 736 is moved rearwards, the reward movement of the clip 706 can be prevented because the base portion of the clip 706 is brought into contact with the blade 737a provided for the fixed plate 737.

Then, the surgical instrument is returned to the initial state so that fixing of the tubular tissue X is successively continued until the plural clips 706 accommodated in the clip cartridge 707 are used.

According to this embodiment, the following effects can be obtained.

That is, the ultrasonic probe 710 supplies the clip 706 to the clip holder 704, and the clip holder 704 is closed by the operation of the operation section 701. Then, the clip 706 is welded by the ultrasonic probe 710. Thus, the tubular tissue X, such as the blood vessel, can reliably be fixed. A simple operation for forwards moving the ultrasonic probe 710 by the operation section 701 enables a sequence of operations including loading of the fixing clip 706 into the clip holder 704, forward movement of the clip 706 in the clip cartridge 707, closing of the clip holder 704 and welding of the clip 706 to be performed successively When the ultrasonic probe 710 is moved rearwards, a next clip 706 can be supplied from the clip cartridge 707. Thus, the operation can easily be performed and time required to complete the operation can be shortened.

Since the clip 706 is made of the material which can be absorbed by the organization, any foreign matter does not retain in the body. Since any latch and hook for fixing the closed shape do not exist at the two ends of the clip 706, the blood vessel can easily be held. Since the two ends of the leg portion 706a of the clip 706 can be fixed by the ultrasonic waves, a reliably closed state can be realized and strong fixing force can be obtained.

Since the clip does not require any latch or a hook, the size of the clip can be reduced. Since the clips are accommodated in the clip cartridge 707 in a straight line, the diameter of the elongation section 702 can be reduced. Thus, the fixing operation can easily be performed even in a narrow and deep portion which is required to be fixed. The clips 706 can successively be used in an operation with an endoscope while inserting the elongation section 702 into the body cavity. Therefore, time required to complete the operation can be shortened.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A surgical instrument for fixing organic tissue with a suturing thread, comprising:
    an applicator for holding a thread fixing member, said applicator including thread fixing means for fixing the thread fixing member to the suturing thread, and operation means for operating the thread fixing means to suture the organic tissue with the suturing thread; and
    forceps arranged to be inserted into a body cavity together with the thread fixing means, said forceps including holding means for holding, when closed, one of the suturing thread and a suturing needle, and forceps-operating means for opening and closing the holding means.

2. A surgical instrument according to claim 1, further comprising:
    first coupling means for coupling the thread fixing means and the operation means with each other and for positioning the thread fixing means and the operation means at a far-end position and a near-end position, respectively;
    second coupling means for coupling the holding means and the forceps-operating means with each other and for positioning the holding means and the forceps-operating means at the far-end position and the near-end position, respectively; and
    an insertion section incorporating the first and second coupling means and adapted to be inserted into the body cavity.

3. A surgical instrument according to claim 1, further comprising:
    at least one connecting member for connecting the applicator and the forceps such that the applicator and the forceps extend in parallel to each other.

4. A surgical instrument according to claim 1, wherein at least one of the applicator and the forceps is movable in an axial direction.

5. A surgical instrument according to claim 1, wherein the thread fixing means welds the thread fixing member with ultrasonic waves to fix the thread fixing member to the suturing thread.

6. A surgical instrument according to claim 5, wherein the thread fixing means is fixed in a state where the thread fixing means is pressed against the thread fixing member until the thread fixing member is completely welded and fixed to the suturing thread with the ultrasonic waves.

7. A surgical instrument according to claim 1, wherein the outer diameter of the insertion section is 10 mm to 12 mm.

8. A surgical instrument according to claim 1, wherein the applicator and the forceps are connected such that decomposition is permitted.

9. A surgical instrument according to claim 1, wherein said operation means comprises means for moving the thread fixing means and the forceps relative to each other and for closing the thread fixing member to thereby connect the thread fixing member to the suturing thread.

10. A surgical instrument according to claim 1, wherein the applicator is able to rotate around an axis running parallel to a lengthwise directional axis of the forceps.

11. A surgical instrument according to claim 1, wherein the thread fixing member comprises a surgical clip having a first clamping portion, a second clamping portion, and a means for connecting the first clamping portion and the second clamping portion together, said surgical clip being made of a thermoplastic resin which is softened when heated.

12. A surgical instrument according to claim 1, wherein the applicator comprises a clip applicator including:
    a clip holder portion;
    clip container means for containing a plurality of surgical clips each having a first clamping portion, a second clamping portion, and a means for connecting the first clamping portion and the second clamping portion together;

clip supply means for feeding one of said surgical clips from the clip container means to the clip holder portion;

means for operating the clip supply means;

closing means for closing said first and second clamping portions of said one of said surgical clips provided to the clip holder portion;

ultrasonic oscillation means for inducing heat in said one of said surgical clips and for softening at least a part of said one of said surgical clips which is formed of a thermoplastic resin; and means for deforming said softened thermoplastic resin of said one of said surgical clips and for clamping said first and second clamping portions of said one of said surgical clips together.

13. A surgical instrument for fixing tubular tissue with a fixing clip, comprising:

an elongation section which is inserted into the body;

an operation section disposed in a portion of an insertion section adjacent to an operator;

a clip cartridge provided for the elongation section to accommodate a plurality of fixing clips;

a clip holder disposed at the leading end of the elongation section to hold and close the fixing clip; and an ultrasonic probe disposed in the elongation section to weld the fixing clip held by the clip holder with ultrasonic waves, wherein the ultrasonic probe is operated when the operation section has been operated so that the leading end of the ultrasonic probe is brought into contact with the fixing clip to push out the fixing clip so as to supply the fixing clip to the clip holder.

14. A surgical instrument according to claim 13, wherein the fixing clip is welded by the ultrasonic probe after the fixing clip has been closed by the clip holder.

15. A surgical instrument according to claim 13, wherein the leading end of the ultrasonic probe, which is brought into contact with the fixing clip, is formed in such a manner that the leading end of the ultrasonic probe is engaged to the rear end of the fixing clip.

16. A surgical instrument according to claim 13, wherein the clip cartridge has a fixed plate having a plurality of blades arranged to be brought into contact with the fixing clips and a movable plate which is capable of moving forwards/rearwards in the lengthwise direction of the clip cartridge and which has a plurality of blades arranged to be brought into contact with the fixing clips, and forward/rearward movement of the movable plate with respect to the fixed plate causes the fixing clip to be moved from the clip cartridge toward the clip holder.

17. A surgical instrument according to claim 16, wherein the movable plate is moved forwards/rearwards attributable to the operation of the operation section in a region between a forward position at which the fixing clip positioned at the frontmost position in the clip cartridge is set into a region in which the fixing clip is able to come in contact with the leading end of the ultrasonic probe and a rearward position at which the fixing clip positioned at the frontmost position in the clip cartridge is retracted from the region.

18. A surgical instrument according to claim 16, wherein the clip holder has an opening/closing section for holding and closing the fixing clip, the elongation section has a holder opening/closing means arranged to be operated by the operation section to open/close the opening/closing section and the movable plate has means for absorbing the difference between a stroke for supplying the fixing clip to the clip holder and a stroke for the clip cartridge.

19. A surgical instrument according to claim 13, wherein the fixing clip comprises a surgical clip having a first clamping portion, a second clamping portion, and a means for connecting the first clamping portion and the second clamping portion together, said surgical clip being made of a thermoplastic resin which is softened when heated.

20. A surgical instrument for fixing tubular tissue with a fixing clip, comprising:

an elongation section which is insertable into a body cavity;

an operation section disposed in a portion of an insertion section adjacent to an operator;

a clip cartridge provided for the elongation section to accommodate a plurality of fixing clips;

a clip holder disposed at a leading end of the elongation section to hold and close the fixing clip;

supply means for supplying the fixing clip from the clip cartridge to the clip holder; and means for maintaining constant a force of the clip holder for closing the fixing clip.

21. A surgical instrument according to claim 20, further comprising:

an ultrasonic probe disposed in the elongation section to weld the fixing clip held by the clip holder with ultrasonic waves.

22. A surgical instrument according to claim 21, wherein the ultrasonic probe presses the fixing clip with predetermined force.

23. A surgical instrument according to claim 20, wherein the clip holder has, at the leading end thereof, a stopper for restraining forward movement of the fixing clip.

24. A surgical instrument according to claim 20, wherein the clip holder has an opening/closing section for holding and closing the fixing clip, the opening/closing section being opened/closed by a link mechanism.

25. A surgical instrument according to claim 20, wherein the fixing clip comprises a surgical clip having a first clamping portion, a second clamping portion, and a means for connecting the first clamping portion and the second clamping portion together, said surgical clip being made of a thermoplastic resin which is softened when heated.

26. A surgical instrument for fixing tubular tissue with a fixing clip, comprising:

an elongation section which is inserted into the body;

an operation section disposed in a portion of an insertion section adjacent to an operator;

a clip cartridge provided for the elongation section to accommodate a plurality of fixing clips;

a clip holder disposed at the leading end of the elongation section to hold and close the fixing clip;

an ultrasonic probe disposed in the central portion of the elongation section to weld the fixing clip held by the clip holder with ultrasonic waves;

supply means disposed on either side of the ultrasonic probe to supply the fixing clip from the clip cartridge to the clip holder;

holder opening/closing means disposed on another side of the ultrasonic probe to open/close the opening/closing section of the clip holder; and a handle disposed in the operation section to operate the holder opening/closing means.

27. A surgical instrument according to claim 26, wherein the holder opening/closing means has a pipe section adjacent to an operator and a bar section adjacent to the leading end, and the pipe section and the bar section are connected to each other at an intermediate position of the elongation section.

28. A surgical instrument according to claim 26, wherein the ultrasonic probe is in the form of a plate-like shape.

29. A surgical instrument according to claim 26, wherein the elongation section is rotatable.

30. A surgical instrument according to claim 26, wherein the fixing clip comprises a surgical clip having a first clamping portion, a second clamping portion, and a means for connecting the first clamping portion and the second clamping portion together, said surgical clip being made of a thermoplastic resin which is softened when heated.

* * * * *